US009534224B2

(12) United States Patent
Collins et al.

(10) Patent No.: US 9,534,224 B2
(45) Date of Patent: Jan. 3, 2017

(54) CIS/TRANS RIBOREGULATORS

(75) Inventors: James J. Collins, Newton, MA (US);
Farren J. Isaacs, Brookline, MA (US);
Charles R. Cantor, Del Mar, CA (US);
Daniel J. Dwyer, Brookline, MA (US)

(73) Assignee: Trustees of Boston University, Boston, MA (US)

( * ) Notice: Subject to any disclaimer, the term of this patent is extended or adjusted under 35 U.S.C. 154(b) by 2084 days.

(21) Appl. No.: 10/535,128

(22) PCT Filed: Nov. 14, 2003

(86) PCT No.: PCT/US03/36506
§ 371 (c)(1),
(2), (4) Date: Apr. 4, 2006

(87) PCT Pub. No.: WO2004/046321
PCT Pub. Date: Jun. 3, 2004

(65) Prior Publication Data
US 2007/0136827 A1   Jun. 14, 2007

Related U.S. Application Data

(60) Provisional application No. 60/426,891, filed on Nov. 15, 2002.

(51) Int. Cl.
*C12N 15/67* (2006.01)
*C12N 15/11* (2006.01)
*C12Q 1/68* (2006.01)

(52) U.S. Cl.
CPC .............. *C12N 15/67* (2013.01); *C12N 15/11* (2013.01); *C12Q 1/6897* (2013.01); *C12N 2310/53* (2013.01)

(58) Field of Classification Search
None
See application file for complete search history.

(56) References Cited

U.S. PATENT DOCUMENTS

| 5,272,065 | A | * | 12/1993 | Inouye et al. | 435/91.1 |
| 5,514,546 | A | | 5/1996 | Kool | 435/6 |
| 5,977,089 | A | | 11/1999 | Arimilli et al. | 514/81 |
| 6,005,087 | A | | 12/1999 | Cook et al. | 536/23.1 |
| 6,031,086 | A | | 2/2000 | Switzer | 536/23.1 |
| 6,127,533 | A | | 10/2000 | Cook et al. | 536/23.1 |
| 6,225,460 | B1 | | 5/2001 | Bischofberger et al. | 536/26.1 |
| 6,323,003 | B1 | | 11/2001 | Black et al. | |
| 6,399,754 | B1 | | 6/2002 | Cook | 536/23.1 |
| 6,403,779 | B1 | | 6/2002 | Kawasaki et al. | 536/23.1 |
| 7,052,903 | B2 | | 5/2006 | Black et al. | |
| 7,439,059 | B2 | | 10/2008 | Black et al. | |

FOREIGN PATENT DOCUMENTS

| WO | WO98-58944 | 12/1998 |
| WO | WO 99/10487 | 3/1999 |

OTHER PUBLICATIONS

Argaman and Altuvia in "fhlA Repression by OxyS RNA: Kissing Complex Formation at Two Sites Results in a Stable Antisense-Target RNA Complex" (J. Mol. Biol. 2000:vol. 300, pp. 1101-1112).*
Altuvia et al in "The *Escherichia coli* OxyS regulatory RNA represses fhlA translation by blocking ribosome binding" (EMBO: 1998 vol. 17, No. 20, pp. 6069-6075).*
International Search Report for PCT/US2003/036506.
International Preliminary Examination Report for PCT/US2003/036506.
Akerley, B. J., et al., "Systematic Identification of Essential Genes by in Vitro Mariner Mutagenesis.", *Proc. Natl. Acad. Sci. U.S.A.* 95: 8927-8932, 1998.
Al-Qahtani, A. and Mensa-Wilmot, K., "A 5' Untranslated Region Which Directs Accurate and Robust Translation by Prokaryotic and Mammalian Ribosomes.", *Nucleic Acids Res.*, 24(6): 1173-1174, 1996.
Altuvia, S. and Wagner, E. G. H., "Switching on and Off With RNA.", *Proc. Natl. Acad. Sci. U.S.A.* 97(18): 9824-9826, 2000.
Andersen, J. B., et al., "New Unstable Variants of Green Fluorescent Protein for Studies of Transient Gene Expression in Bacteria.", *Appl. Environ. Microbiol.* 64: 2240-2246, 1998.
Arigoni, F., et al., "A Genome-Based Approach for the Identification of Essential Bacterial Genes.", *Nat. Biotechnol.* 16: 851-856, 1998.
Banerji, et al., "A Lymphocyte-Specific Cellular Enhancer Is Located Downstream of the Joining Region in Immunoglobulin Heavy Chain Genes.", *Cell* 33: 729-740, 1983.

(Continued)

*Primary Examiner* — Catherine S Hibbert
(74) *Attorney, Agent, or Firm* — Nixon Peabody LLP

(57) ABSTRACT

The present invention provides nucleic acid molecules, DNA constructs, plasmids, and methods for post-transcriptional regulation of gene expression using RNA molecules to both repress and activate translation of an open reading frame. Repression of gene expression is achieved through the presence of a regulatory nucleic acid element (the cis-repressive RNA or crRNA) within the 5' untranslated region (5' UTR) of an mRNA molecule. The nucleic acid element forms a hairpin (stem/loop) structure through complementary base pairing. The hairpin blocks access to the mRNA transcript by the ribosome, thereby preventing translation. In particular, in embodiments of the invention designed to operate in prokaryotic cells, the stem of the hairpin secondary structure sequesters the ribosome binding site (RBS). In embodiments of the invention designed to operate in eukaryotic cells, the stem of the hairpin is positioned upstream of the start codon, anywhere within the 5' UTR of an mRNA. A small RNA (trans-activating RNA, or taRNA), expressed in trans, interacts with the crRNA and alters the hairpin structure. This alteration allows the ribosome to gain access to the region of the transcript upstream of the start codon, thereby activating transcription from its previously repressed state.

43 Claims, 12 Drawing Sheets

(56) References Cited

OTHER PUBLICATIONS

Barrick, D., et al., "Quantitative Analysis of Ribosome Binding Sites in E. coli.", Nuc. Acids. Res. 22(7): 1287-1295, 1994.
Bartel, D. P. and Szostak, J. W., "Isolation of New Ribozymes From a Large Pool of Random Sequences.",Science 261: 1411-1418, 1993.
Bedford, E., et al., "The Thioredoxin Binding Domain of Bacteriophage T7 DNA Polymerase Confers Processivity on Escherichia coli DNA Polymerase I.", Proc. Natl. Acad. Sci. USA, 94: 479-84, 1997.
Blau, H. and Rossi, F.M.V., "Tet B or Not Tet B: Advances in Tetracycline-Inducible Gene Expression.", Proc. Natl. Acad. Sci., 96: 797-799, 1999.
Boyd, D., et al., "Towards Single-Copy Gene Expression Systems Making Gene Cloning Physiologically Relevant: Lambda InCh, A Simple Escherichia coli Plasmid-Chromosome Shuttle System.", J. Bacteriol., 182: 842-847, 2000.
Brautigan, C.A. and Steitz, T.A., "Structural and Functional Insights Provided by Crystal Structures of DNA Polymerases and Their Substrate Complexes.", Curr. Opin. Struct. Biol., 8: 54-63, 1998.
Breaker, R. R., "In Vitro Selection of Catalytic Polynucleotides.", Chem. Rev. 97: 371-390, 1997.
Byrne, et al., "Multiplex Gene Regulation: A Two-Tiered Approach to Transgene Regulation in Transgenic Mice.", Proc. Natl. Acad. Sci. USA 86: 5473-5477, 1989.
Calame, et al., "Transcriptional Controlling Elements in the Immunoglobulin and T Cell Receptor Loci.", Adv. Immunol. 43: 235-275, 1988.
Camper, S.A., et al., "Postnatal Repression of the α-Fetoprotein Gene Is Enhancer Independent.", Genes Dev. 3: 537-546, 1989.
Capecchi, M.R., "Altering the Genome by Homologous Recombination.", Science 244: 1288-1292, 1989.
Chen, H., et al., "Determination of the Optimal Aligned Spacing Between the Shine-Dalgarno Sequence and the Translation Initiation Codon of Escherichia coli mRNAs.", Nucleic Acids Res., 22: 4953-4957, 1994.
Cheung, A. L., et al., "Insertional Inactivation of a Chromosomal Locus That Modulates Expression of Potential Virulence Determination in Staphylococcus aureus.", J. Bacteriol. 177: 3220-3226, 1995.
Cormack, B. P., et al., "FACS-Optimized Mutants of the Green Fluorescent Protein (GFP).", Gene 173: 33-38, 1996.
Court, D., "RNA Processing and Degradation by RNase III.", Control of Messenger RNA Stability, 71-116, 1993.
Davies, D., et al., "Three-Dimensional Structure of the Tn5 Synaptic Complex Transportation Intermediate.", Science, 289: 77-85, 2000.
Ding, C. and Cantor, C. R., "A High-Throughput Gene Expression Analysis Technique Using Competitive PCR and Matrix-Assisted Laser Desorption Ionization Time-of-Flight MS.", Proc. Natl. Acad. Sci. U.S.A. 100: 3059-3064, 2003.
Doudna, J. A. and Cech, T. R., "The Chemical Repertoire of Natural Ribozymes.", Nature 418: 222-228, 2002.
Eddy, S. R., "Non-Coding RNA Genes and the Modern RNA World.", Nat. Rev. Genet. 2: 919-929, 2001.
Ellington, A. D. and Szostak, J. W., "In Vitro Selection of RNA Molecules That Bind Specific Ligands.", Nature 346: 818-822, 1990.
Emory SA, et al., "A 5'-Terminal Stem-Loop Structure Can Stabilize mRNA in Escherichia coli.", Genes Dev. 6: 135-148, 1992.
Engdahl, H. M., et al., "Introduction of an RNA Stability Element At the 5'-End of an Antisense RNA Cassette Increases the Inhibition of Target RNA Translation.", Antisense Nucleic Acid Drug Development 11: 29-40, 2001.
Franch, T., et al., "Antisense RNA Regulation in Prokaryotes: Rapid RNA/RNA Interaction Facilitated by a General U-Turn Loop Structure.", J. Mol. Biol. 294: 1115-1125, 1999.
Guerrier-Takada, C., et al., "The RNA Moiety of Ribonulease P Is the Catalytic Subunit of the Enzyme.", Cell 35: 849-857, 1983.

Guet, C. C., et al., "Combinational Synthesis of Genetic Networks. ", Science 296: 1466-1470, 2002.
Hasty, J., et al., "Engineered Gene Circuits.", Nature 420: 224-230, 2002.
Hellen, C.U.T. and Sarnow, P., "Internal Ribosome Entry Sites in Eukaryotic mRNA Molecules.", Genes Dev., 15(13): 1593-1612, 2001.
Hensel, M., et al., "Simultaneous Identification of Bacterial Virulence Genes by Negative Selection.", Science 269: 400-403, 1995.
Hermann, T. and Patel, D., "Adaptive Recognition by Nucleic Acid Aptamers.", Science, 287: 820-825, 2000.
Hjalt, T. A. H. and Wagner, E. G. H., "Bulged-Out Nucleotides Protect an Antisense RNA From RNase III Cleavage.", Nucleic Acids Res. 23(4): 571-579, 1995.
Hutvagner, G. and Zamore, PD., "RNAi: Nature Abhors a Double-Strand.", Curr. Op. Genet. Dev. 12: 225-232, 2002.
Jestin, J.L., et al., "A Method for the Selection of Catalytic Activity Using Phage Display and Proximity Coupling.", Angew. Chem. Int. Ed. 38: 1124-1127, 1999.
Ji, Y., et al., "Identification of Critical Staphylococcal Genes Using Conditional Phenotypes Generated by Antisense RNA.", Science 293: 2266-2269, 2001.
Johansson, J., et al., "An RNA Thermosensor Controls Expression of Virulence Genes in Listeria Monocytogenes.", Cell 110: 551-561, 2002.
Joyce, G. F., "Amplification, Mutation and Selection of Catalytic RNA.", Gene 82: 83-87, 1989.
Joyce, G. F., "The Antiquity of RNA-Based Evolution.", Nature 418: 214-221, 2002.
Kaern M, et al., "The Engineering of Gene Regulatory Networks.", Annu Rev Biomed Eng. 5: 179-206, 2003.
Kessel, et al., "Murine Developmental Control Genes.", Science 249: 374-379, 1990.
Kozak, M., "The Scanning Model for Translation: An Update.", J. Cell Biol. 108: 229-241, 1989.
Kozak, M., "At Least Six Nucleotides Preceding the AUG Initiator Codon Enhance Translation in Mammalian Cells.", J. Mol. Biol. 196: 947-950, 1987.
Kozak, M., "Features in the 5' Non-Coding Sequences of Rabbit α and β-Globin mRNAs That Affect Translational Efficiency.", J. Mol. Biol., 235: 95-110, 1994.
Kruger, K., et al., "Self-Splicing RNA: Autoexcision and Autocyclization of the Ribosomal RNA Intervening Sequence of Tetrahymena.", Cell 31: 147-157, 1982.
Landweber, L, "Experimental RNA Evolution.", Trends in Ecology and Evolution, 14(9): 353-358, 1999.
Lease, R. A. and Belfort, M., "A Trans-Acting RNA as a Control Switch in Escherichia coli: DsrA Modulates Function by Forming Alternative Structures.", Proc. Natl. Acad. Sci. U.S.A. 97: 9919-9924, 2000.
Lee, R. C., et al., "The C. Elegans Heterochronic Gene Lin-4 Encodes Small RNAs With Antisense Complementarity to Lin-14.", Cell 75: 843-854, 1993.
Lewandoski, M., "Conditional Control of Gene Expression in the Mouse.", Nat Rev Genet., 2(10): 743-55, 2001.
Li, Y. et al., "Crystal Structures of Open and Closed Forms of Binary and Ternary Complexes of the Large Fragment of Thermus aquaticus DNA Polymerase I: Structural Basis for Nucleotide Incorporation.", EMBO J., 17: 7514-7525, 1998.
Li, Y., et al., "Structure-Based Design of Taq DNA Polymerases With Improved Properties of Dideoxynucleotide Incorporation.", Proc. Natl. Acad. Sci. USA, 96: 9491-9496, 1999.
Lutz, R. and Bujard, H., "Independent and Tight Regulation of Transcriptional Units in Escherichia coli via the LacR/O, the TetR/O and AraC/I1-I2 Regulatory Elements.", Nucleic Acids Res. 25: 1203-1210, 1997.
Mandal, M., et al., "Riboswitches Control Fundamental Biochemical Pathways in Bacillus subtilis and Other Bacteria.", Cell 113: 577-586, 2003.
Martinez-Salas, E., "Internal Ribosome Entry Site Biology and Its Use in Expression Vectors.", Current Opinion in Biotechnology. 10: 458-464, 1999.

(56) References Cited

OTHER PUBLICATIONS

Mathews, D.H., et al., "Expanded Sequence Dependence of Thermodynamic Parameters Improves Prediction of RNA Secondary Structure.", *J. Mol. Biol.* 288: 911-940, 1999.

Mironov, A., et al., "Sensing Small Molecules by Nascent RNA: A Mechanism to Control Transcription in Bacteria.", *Cell* 111: 747-756, 2002.

Morfeldt, E.. et al., "Activation of Alpha-Toxin Translation in *Staphylococcus aureus* by the Trans-Encoded Antisense RNA, RNAIII.", *EMBO J* 14(18): 4569-4577, 1995.

Morita, M. T., et al., "Translational Induction of Heat Shock Transcription Factor σ32: Evidence for a Built-In RNA Thermosensor.", *Genes Dev.* 13: 655-665, 1999.

Nahvi, A., et al., "Genetic Control by a Metabolite Binding mRNA.", *Chem. Biol.* 9: 1043-1049, 2002.

Nyanguile, O., et al., "A Nonnatural Transcriptional Coactivator.", *Proc. Natl. Acad. Sci. USA* 94(25): 13402-13406, 1997.

Oberholzer, T., et al., "Polymerase Chain Reaction in Liposomes.", *Chem. Biol.*, 2: 677-82, 1995.

Pestova, T.V., et al., "Molecular Mechanisms of Translation Initiation in Eukaryotes.", *Proc. Natl. Acad. Sci.* 98(13): 7029-7036, 2001.

Pyle, A.M., et al., "Direct Measurements of Oligonucleotide Substrate Binding to Wild-Type and Mutant Ribozymes From *Tetrahymena.*", *Proc. Natl. Acad. Sci. USA.*, 87: 8187-8191, 1990.

Queen, et al., "Immunoglobulin Gene Transcription Is Activated by Downstream Sequence Elements.", *Cell* 33: 741-748, 1983.

Ringquist, S., et al., "Translation Initiation in *Escherichia coli*: Sequences Within the Ribosome-Binding Site.", *Molec. Microbiol.*, 6(9): 1219-1229, 1992.

Rudd, K.E. and Schneider, T.D., "C. Compilation of *E. coli* Ribosome Binding Sites.", *A Short Course in Bacterial Genetics: A Laboratory Manual and Handbook for Escherichia coli and related bacteria.*, 17.19-17.45.

Sanger, et. al., "DNA Sequencing With Chain-Terminating Inhibitors.", *Proc. Natl. Acad. Sci. U.S.A.* 74: 5463-5467, 1977.

Stojanovic, M. N. and Stefanovic, D., "A Deoxyribozyme-Based Molecular Automation.", *Nat. Biotechnol.* 21: 1069-1074, 2003.

Stougaard, P., et al., "RNAs Involved in Copy-Number Control and Incompatibility of Plasmid R1.", *Proc. Natl. Acad. Sci. USA* 78: 6008-6012, 1981.

Sudarson, N., et al., "Metabolic-Binding RNA Domains Are Present in the Genes of Eukaryotes.", *RNA*, 9: 644-647, 2003.

Suzuki, M., et al., "Random Mutagenesis of *Thermus aquaticus* DNA Polymerase I: Concordance of Immutable Sites in Vivo With the Crystal Structure.", *Proc. Natl. Acad. Sci. USA*, 93: 9670-9675, 1996.

Tabor, JJ and Ellington, AD., "Playing to Win At DNA Computation. An Automaton Built With DNA Enzymes Plays Tic-Tac-Toe Against Human Players.", *Nat. Biotechnol.*, 21(9): 1013-1015, 2003.

Tuerk, C. and Gold, L., "Systematic Evolution of Ligands by Exponential Enrichment: RNA Ligands to Bacteriophage T4 DNA Polymerase.", *Science* 249: 505-510, 1990.

Vartanian, J.-P., et al., "Hypermutagenic PCR Involving All Four Transitions and a Sizeable Proportion of Transversions.", *Nuc. Acids Res.*, 24(14): 2627-2631, 1996.

Wagner, E. G. H. and Flardh, K., "Antisense RNAs Everywhere?", *Trends in Genetics* 18: 223-226, 2002.

Wagner, E. G. H. and Simons, R. W., "Antisense RNA Control in Bacteria, Phages, and Plasmids.", *Annu. Rev. Microbiol.* 48: 713-742, 1994.

Werstuck, G. and Green, M., "Controlling Gene Expression in Living Cells Through Small Molecule-RNA Interactions.", *Science*, 282: 296-298, 1998.

Wild, J., et al., "Conditionally Amplifiable BACs: Switching From Single-Copy to High Copy Vectors and Genomic Clones.", *Genome Res.*, 12: 1434-1444, 2002.

Wilson, D. S. and Szostak, J. W., "In Vitro Selection of Functional Nucleic Acids.", *Annu. Rev. Biochem.* 68: 611-647, 1999.

Winfree, E., et al., "Design and Self-Assembly of Two-Dimensional DNA Crystals.", *Nature* 394: 539-544, 1998.

Winkler, W., et al., "Thiamine Derivatives Bind Messenger RNAs Directly to Regulate Bacterial Gene Expression.", *Nature* 419: 952-956, 2002.

Winkler, W., et al., "An mRNA Structure That Controls Gene Expression by Binding FMN.", *Proc. Natl. Acad. Sci. U.S.A.* 99: 15908-15913, 2002.

Winoto, et al., "A Novel, Inducible and T Cell-Specific Enhancer Located At the 3' End of the T Cell Receptor α Locus.", *EMBO J.* 8: 729-733, 1989.

Zaccolo, M., et al., "The Effect of High-Frequency Random Mutagenesis on in Vitro Protein Evolution: A Study on TEM-1 β-Lactamase.", *J. Mol. Biol.*, 285: 775-783, 1999.

Zuker, M., "Mfold Web Server for Nucleic Acid Folding and Hybridization Prediction.", *Nucleic Acids Res.* 31: 3406-3415, 2003.

Black, C.A., "Switching on Gene Therapy: Using Gene Profiles to Design Drugs," *PharmaGenomics*, 2003, 48-53.

\* cited by examiner

SEQUENCE LISTING

```
<160> NUMBER OF SEQ ID NOS: 58

<210> SEQ ID NO 1
<211> LENGTH: 10
<212> TYPE: RNA
<213> ORGANISM: Artificial Sequence
<220> FEATURE:
<223> OTHER INFORMATION: Kozak consensus sequence
<220> FEATURE:
<221> NAME/KEY: misc_feature
<222> LOCATION: (4)..(4)
<223> OTHER INFORMATION: r=g or a

<400> SEQUENCE: 1 gccrccaugc                                                          10
```

```
<210> SEQ ID NO 2
<211> LENGTH: 18
<212> TYPE: DNA
<213> ORGANISM: Artificial Sequence
<220> FEATURE:
<223> OTHER INFORMATION: RBS-spacer-start codon sequence

<400> SEQUENCE: 2
aggagggttt ttaccaug                                                 18

<210> SEQ ID NO 3
<211> LENGTH: 19
<212> TYPE: DNA
<213> ORGANISM: Artificial Sequence
<220> FEATURE:
<223> OTHER INFORMATION: Corresponding DNA sequence of Cis-respressive
      RNA sequence (C)

<400> SEQUENCE: 3
ggacgcactg accgaattc                                                19

<210> SEQ ID NO 4
<211> LENGTH: 20
<212> TYPE: DNA
<213> ORGANISM: Artificial Sequence
<220> FEATURE:
<223> OTHER INFORMATION: Corresponding DNA sequence of Cis-respressive
      RNA sequence (crRL)

<400> SEQUENCE: 4
ctacctttct cctctttaat                                               20

<210> SEQ ID NO 5
<211> LENGTH: 18
<212> TYPE: DNA
<213> ORGANISM: Artificial Sequence
<220> FEATURE:
<223> OTHER INFORMATION: Corresponding DNA sequence of Cis-respressive
      RNA sequence (crRB)

<400> SEQUENCE: 5
ttctctagtc ctcccttat                                                18

<210> SEQ ID NO 6
<211> LENGTH: 19
<212> TYPE: DNA
<213> ORGANISM: Artificial Sequence
<220> FEATURE:
<223> OTHER INFORMATION: Corresponding DNA sequence of Cis-respressive
      RNA sequence (crR7)

<400> SEQUENCE: 6
ctacctttct cctctagga                                                19

<210> SEQ ID NO 7
<211> LENGTH: 19
<212> TYPE: DNA
<213> ORGANISM: Artificial Sequence
<220> FEATURE:
<223> OTHER INFORMATION: Corresponding DNA sequence of Cis-respressive
      RNA sequence (crR10)

<400> SEQUENCE: 7
ctacctatct gctcttgaa                                                19
```

```
<210> SEQ ID NO 8
<211> LENGTH: 19
<212> TYPE: DNA
<213> ORGANISM: Artificial Sequence
<220> FEATURE:
<223> OTHER INFORMATION: Corresponding DNA sequence of Cis-respressive
      RNA sequence (crR12)

<400> SEQUENCE: 8
ctaccattca cctcttgga                                                19

<210> SEQ ID NO 9
<211> LENGTH: 16
<212> TYPE: DNA
<213> ORGANISM: Artificial Sequence
<220> FEATURE:
<223> OTHER INFORMATION: Corresponding DNA sequence of Cis-respressive
      RNA sequence (crR22)

<400> SEQUENCE: 9
ctaccattca cctgga                                                   16

<210> SEQ ID NO 10
<211> LENGTH: 15
<212> TYPE: DNA
<213> ORGANISM: Artificial Sequence
<220> FEATURE:
<223> OTHER INFORMATION: Corresponding DNA sequence of Cis-respressive
      RNA sequence (RBS)

<400> SEQUENCE: 10
attaaagagg agaaa                                                    15

<210> SEQ ID NO 11
<211> LENGTH: 43
<212> TYPE: DNA
<213> ORGANISM: Artificial Sequence
<220> FEATURE:
<223> OTHER INFORMATION: Corresponding DNA sequence of Cis-respressive
      RNA construct (C)

<400> SEQUENCE: 11
ggacgcactg accgaattca ttaaagagga gaaaggtacc atg                     43

<210> SEQ ID NO 12
<211> LENGTH: 51
<212> TYPE: DNA
<213> ORGANISM: Artificial Sequence
<220> FEATURE:
<223> OTHER INFORMATION: Corresponding DNA sequence of Cis-respressive
      RNA construct (crRL)

<400> SEQUENCE: 12
ctacctttct cctctttaat tttgggtatt aaagaggaga aaggtaccat g             51

<210> SEQ ID NO 13
<211> LENGTH: 47
<212> TYPE: DNA
<213> ORGANISM: Artificial Sequence
<220> FEATURE:
<223> OTHER INFORMATION: Corresponding DNA sequence of Cis-respressive
      RNA construct (crRB)

<400> SEQUENCE: 13
ctctagtcct ccttattttg ggtattaaag aggagaaagg taccatg                 47

<210> SEQ ID NO 14
```

```
<211> LENGTH: 50
<212> TYPE: DNA
<213> ORGANISM: Artificial Sequence
<220> FEATURE:
<223> OTHER INFORMATION: Corresponding DNA sequence of Cis-respressive
      RNA construct (crR7)

<400> SEQUENCE: 14
ctacctttct cctctaggat ttgggtatta aagaggagaa aggtaccatg            50

<210> SEQ ID NO 15
<211> LENGTH: 50
<212> TYPE: DNA
<213> ORGANISM: Artificial Sequence
<220> FEATURE:
<223> OTHER INFORMATION: Corresponding DNA sequence of Cis-respressive
      RNA construct (crR10)

<400> SEQUENCE: 15
ctacctatct gctcttgaat ttgggtatta aagaggagaa aggtaccatg            50

<210> SEQ ID NO 16
<211> LENGTH: 50
<212> TYPE: DNA
<213> ORGANISM: Artificial Sequence
<220> FEATURE:
<223> OTHER INFORMATION: Corresponding DNA sequence of Cis-respressive
      RNA construct (crR12)

<400> SEQUENCE: 16
ctaccattca cctcttggat ttgggtatta aagaggagaa aggtaccatg            50

<210> SEQ ID NO 17
<211> LENGTH: 50
<212> TYPE: DNA
<213> ORGANISM: Artificial Sequence
<220> FEATURE:
<223> OTHER INFORMATION: Corresponding DNA sequence of Cis-respressive
      RNA construct (crR22)

<400> SEQUENCE: 17
ctaccattca cctcttggat ttgggtatta aagaggagaa aggtaccatg            50

<210> SEQ ID NO 18
<211> LENGTH: 71
<212> TYPE: DNA
<213> ORGANISM: Artificial Sequence
<220> FEATURE:
<223> OTHER INFORMATION: Corresponding DNA sequence of Trans-activating
      RNA construct (taRL)

<400> SEQUENCE: 18
acacccaaat taaagaggag aaaggtagtg gtggttaatg aaaattaact tactactacc   60
tttttcttag a                                                       71

<210> SEQ ID NO 19
<211> LENGTH: 62
<212> TYPE: DNA
<213> ORGANISM: Artificial Sequence
<220> FEATURE:
<223> OTHER INFORMATION: Corresponding DNA sequence of Trans-activating
      RNA construct (taRB)

<400> SEQUENCE: 19
acgccccaat aaggaggata gagtggtggt taatgaaaat taacttacta cttagttttta  60 ga                                                                 62
```

<210> SEQ ID NO 20
<211> LENGTH: 69
<212> TYPE: DNA
<213> ORGANISM: Artificial Sequence
<220> FEATURE:
<223> OTHER INFORMATION: Corresponding DNA sequence of Trans-activating
      RNA construct (taR7)

<400> SEQUENCE: 20
acacccaaat cctagggaga atggtagtgg tggttaatga aaattaactt actactactt    60
tttcataga                                                            69

<210> SEQ ID NO 21
<211> LENGTH: 67
<212> TYPE: DNA
<213> ORGANISM: Artificial Sequence
<220> FEATURE:
<223> OTHER INFORMATION: Corresponding DNA sequence of Trans-activating
      RNA construct (taR10)

<400> SEQUENCE: 21
acacccaaat tatgagcaga ttggtagtgg tggttaatga aaattaactt actactactt    60
tcttaga                                                              67

<210> SEQ ID NO 22
<211> LENGTH: 71
<212> TYPE: DNA
<213> ORGANISM: Artificial Sequence
<220> FEATURE:
<223> OTHER INFORMATION: Corresponding DNA sequence of Trans-activating
      RNA construct (taR12)

<400> SEQUENCE: 22
acccaaatcc aggaggtgat tggtagtggt ggttaatgaa aattaactta ctactaccat    60
atatctctag a                                                         71

<210> SEQ ID NO 23
<211> LENGTH: 71
<212> TYPE: DNA
<213> ORGANISM: Artificial Sequence
<220> FEATURE:
<223> OTHER INFORMATION: Corresponding DNA sequence of Trans-activating
      RNA construct (taR12A)

<400> SEQUENCE: 23
acccaaatcc aggaggtgaa tggtagtggt ggttaatgaa aattaactta ctactaccat    60
atatctctag a                                                         71

<210> SEQ ID NO 24
<211> LENGTH: 71
<212> TYPE: DNA
<213> ORGANISM: Artificial Sequence
<220> FEATURE:
<223> OTHER INFORMATION: Corresponding DNA sequence of Trans-activating
      RNA construct (taR12B)

<400> SEQUENCE: 24
acccaaatcc aagaggtgat tggtagtggt ggttaatgaa aattaactta ctactaccat    60
atatctctag a                                                         71

<210> SEQ ID NO 25
<211> LENGTH: 76

```
<212> TYPE: DNA
<213> ORGANISM: Artificial Sequence
<220> FEATURE:
<223> OTHER INFORMATION: Corresponding DNA sequence of Trans-activating
      RNA construct (taR12C)

<400> SEQUENCE: 25
acccaaatcc aaagaggtga atggtaagtg ggtggttaat gaaaattaac ttactactac    60
catatattct ctaaga                                                    76

<210> SEQ ID NO 26
<211> LENGTH: 71
<212> TYPE: DNA
<213> ORGANISM: Artificial Sequence
<220> FEATURE:
<223> OTHER INFORMATION: Corresponding DNA sequence of Trans-activating
      RNA construct (taRU112)

<400> SEQUENCE: 26
acccaaatcc aggaggtgat tggtagtggt ggttaatgaa aattaactta ctaaaatcgg    60
acatctctag a                                                         71

<210> SEQ ID NO 27
<211> LENGTH: 75
<212> TYPE: DNA
<213> ORGANISM: Artificial Sequence
<220> FEATURE:
<223> OTHER INFORMATION: Corresponding DNA sequence of Trans-activating
      RNA construct (taRU212)

<400> SEQUENCE: 27
acccaaatcc aggaggtgat tggtagtggt ggttaatgaa aattaacttt actacttacg    60
cgtcatatct ctaga                                                     75

<210> SEQ ID NO 28
<211> LENGTH: 71
<212> TYPE: DNA
<213> ORGANISM: Artificial Sequence
<220> FEATURE:
<223> OTHER INFORMATION: Corresponding DNA sequence of Trans-activating
      RNA construct (taRU312)

<400> SEQUENCE: 28
acccaaatcc aggaggtgat tggtagtggt ggttaatgaa aattaactta ctacgatcag    60
tgatctctag a                                                         71

<210> SEQ ID NO 29
<211> LENGTH: 69
<212> TYPE: DNA
<213> ORGANISM: Artificial Sequence
<220> FEATURE:
<223> OTHER INFORMATION: Corresponding DNA sequence of Trans-activating
      RNA construct (taR22)

<400> SEQUENCE: 29
acccaaatcc aggtgtatgg tagtggtggt taatgaaaat taacttacta ccattcacct    60
cgatctaga                                                            69

<210> SEQ ID NO 30
<211> LENGTH: 35
<212> TYPE: RNA
<213> ORGANISM: Artificial Sequence
<220> FEATURE:
<223> OTHER INFORMATION: Sequence of Trans-activating RNA construct
```

```
                (5'-st)

<400> SEQUENCE: 30
ggguccgcua ugagguaaag ugucauagcg ggccc                           35

<210> SEQ ID NO 31
<211> LENGTH: 19
<212> TYPE: DNA
<213> ORGANISM: Artificial Sequence
<220> FEATURE:
<223> OTHER INFORMATION: Cy5-labeled reverse transcription primer

<400> SEQUENCE: 31
cttcaccctc tccactgac                                             19

<210> SEQ ID NO 32
<211> LENGTH: 30
<212> TYPE: DNA
<213> ORGANISM: Artificial Sequence
<220> FEATURE:
<223> OTHER INFORMATION: PCR primer 1 (Assay 16SrRNA)

<400> SEQUENCE: 32
acgttggatg ggagactgcc agtgataaac                                 30

<210> SEQ ID NO 33
<211> LENGTH: 29
<212> TYPE: DNA
<213> ORGANISM: Artificial Sequence
<220> FEATURE:
<223> OTHER INFORMATION: PCR primer 2 (Assay 16SrRNA)

<400> SEQUENCE: 33
acgttggatg tgtagccctg gtcgtaagg                                  29

<210> SEQ ID NO 34
<211> LENGTH: 21
<212> TYPE: DNA
<213> ORGANISM: Artificial Sequence
<220> FEATURE:
<223> OTHER INFORMATION: Extension primer (Assay 16SrRNA)

<400> SEQUENCE: 34
gaggaaggtg ggggatgacg t                                          21

<210> SEQ ID NO 35
<211> LENGTH: 74
<212> TYPE: DNA
<213> ORGANISM: Artificial Sequence
<220> FEATURE:
<223> OTHER INFORMATION: Competitor Sequence (Assay 16SrRNA)

<400> SEQUENCE: 35
tgtagccctg gtcgtaaggg ccatgatgac ttcacgtcat ccccaccttc ctccagttat 60
cactggcagt ctcc                                                  74

<210> SEQ ID NO 36
<211> LENGTH: 30
<212> TYPE: DNA
<213> ORGANISM: Artificial Sequence
<220> FEATURE:
<223> OTHER INFORMATION: PCR primer 1 (Assay crRNA)

<400> SEQUENCE: 36
acgttggatg ggagagggtg aaggtgatgc                                 30
```

<210> SEQ ID NO 37
<211> LENGTH: 30
<212> TYPE: DNA
<213> ORGANISM: Artificial Sequence
<220> FEATURE:
<223> OTHER INFORMATION: PCR primer 2 (Assay crRNA)

<400> SEQUENCE: 37
acgttggaag aggtagtttt ccagtagtgc        30

<210> SEQ ID NO 38
<211> LENGTH: 20
<212> TYPE: DNA
<213> ORGANISM: Artificial Sequence
<220> FEATURE:
<223> OTHER INFORMATION: Extension primer (Assay crRNA)

<400> SEQUENCE: 38
catacggaaa acttaccctt        20

<210> SEQ ID NO 39
<211> LENGTH: 75
<212> TYPE: DNA
<213> ORGANISM: Artificial Sequence
<220> FEATURE:
<223> OTHER INFORMATION: Competitor sequence (Assay crRNA)

<400> SEQUENCE: 39
tgtagccctg gtcgtaaggg ccatgatgac ttcacgtcat ccccaccttc ctccagttta        60
tcactggcag tctcc        75

<210> SEQ ID NO 40
<211> LENGTH: 30
<212> TYPE: DNA
<213> ORGANISM: Artificial Sequence
<220> FEATURE:
<223> OTHER INFORMATION: PCR primer 1 (Assay taRNA)

<400> SEQUENCE: 40
acgttggatg tttctccata gtcgacaccc        30

<210> SEQ ID NO 41
<211> LENGTH: 30
<212> TYPE: DNA
<213> ORGANISM: Artificial Sequence
<220> FEATURE:
<223> OTHER INFORMATION: PCR primer 2 (Assay taRNA)

<400> SEQUENCE: 41
acgttggatg ctgccgccag gcatctagag        30

<210> SEQ ID NO 42
<211> LENGTH: 21
<212> TYPE: DNA
<213> ORGANISM: Artificial Sequence
<220> FEATURE:
<223> OTHER INFORMATION: Extension Primer (Assay taRNA)

<400> SEQUENCE: 42
gaaaattaac ttactactac c        21

<210> SEQ ID NO 43
<211> LENGTH: 19
<212> TYPE: DNA

```
<213> ORGANISM: Artificial Sequence
<220> FEATURE:
<223> OTHER INFORMATION: Competitor Sequence (Assay taRNA)

<400> SEQUENCE: 43
taatacgact cactatagg                                               19

<210> SEQ ID NO 44
<211> LENGTH: 48
<212> TYPE: DNA
<213> ORGANISM: Artificial Sequence
<220> FEATURE:
<223> OTHER INFORMATION: PCR primer for crR7, 10, 12 (forward)

<400> SEQUENCE: 44
attactcgag taatacgact cactataggt cagcaggacg cactgacc               48

<210> SEQ ID NO 45
<211> LENGTH: 47
<212> TYPE: DNA
<213> ORGANISM: Artificial Sequence
<220> FEATURE:
<223> OTHER INFORMATION: PCR primer for taR7 (forward)

<400> SEQUENCE: 45
attactcgag taatacgact cactatagga cccaaatcct agcggag                47

<210> SEQ ID NO 46
<211> LENGTH: 51
<212> TYPE: DNA
<213> ORGANISM: Artificial Sequence
<220> FEATURE:
<223> OTHER INFORMATION: PCR primer for taR10 (forward)

<400> SEQUENCE: 46
attactcgag taatacgact cactatagga cccaaattca tgagcagatt g           51

<210> SEQ ID NO 47
<211> LENGTH: 47
<212> TYPE: DNA
<213> ORGANISM: Artificial Sequence
<220> FEATURE:
<223> OTHER INFORMATION: PCR primer for taR12 (forward)

<400> SEQUENCE: 47
attactcgag taatacgact cactatagga cccaaatcca ggaggtg                47

<210> SEQ ID NO 48
<211> LENGTH: 30
<212> TYPE: DNA
<213> ORGANISM: Artificial Sequence
<220> FEATURE:
<223> OTHER INFORMATION: PCR primer for crR7, 10, 12 (reverse)

<400> SEQUENCE: 48
gtccaagctt ttatttgtat agttcatcca                                   30

<210> SEQ ID NO 49
<211> LENGTH: 15
<212> TYPE: DNA
<213> ORGANISM: Artificial Sequence
<220> FEATURE:
<223> OTHER INFORMATION: PCR primer for taR10 (reverse)

<400> SEQUENCE: 49
accaccgcgc tactg                                                   15
```

<210> SEQ ID NO 50
<211> LENGTH: 55
<212> TYPE: RNA
<213> ORGANISM: Artificial Sequence
<220> FEATURE:
<223> OTHER INFORMATION: RNA sequence of crRL

<400> SEQUENCE: 50
gaauucuacc uuucuccucu uuaauuuggg uauuaaagag gagaaaggua ccaug    55

<210> SEQ ID NO 51
<211> LENGTH: 55
<212> TYPE: RNA
<213> ORGANISM: Artificial Sequence
<220> FEATURE:
<223> OTHER INFORMATION: RNA sequence of crR7

<400> SEQUENCE: 51
gaauucuacc uuucuccucu aggauuuggg uauuaaagag gagaaaggua ccaug    55

<210> SEQ ID NO 52
<211> LENGTH: 55
<212> TYPE: RNA
<213> ORGANISM: Artificial Sequence
<220> FEATURE:
<223> OTHER INFORMATION: RNA sequence of crR10

<400> SEQUENCE: 52
gaauucuacc uaucugcucu ugaauuuggg uauuaaagag gagaaaggua ccaug    55

<210> SEQ ID NO 53
<211> LENGTH: 52
<212> TYPE: RNA
<213> ORGANISM: Artificial Sequence
<220> FEATURE:
<223> OTHER INFORMATION: RNA sequence of crRB

<400> SEQUENCE: 53
gaauucucua guccuccuua uuuuggguau uaaagaggag aaagguacca ug    52

<210> SEQ ID NO 54
<211> LENGTH: 50
<212> TYPE: RNA
<213> ORGANISM: Artificial Sequence
<220> FEATURE:
<223> OTHER INFORMATION: RNA sequence of C

<400> SEQUENCE: 54
aucagcagga cgcacugacc gaauucauua aagaggagaa agguaccaug    50

<210> SEQ ID NO 55
<211> LENGTH: 71
<212> TYPE: RNA
<213> ORGANISM: Artificial Sequence
<220> FEATURE:
<223> OTHER INFORMATION: RNA sequence of taR12

<400> SEQUENCE: 55
acccaaaucc aggaggugau ugguaguggu gguuaaugaa aauuaacuua cuacuaccau    60
auaucucuag a    71

<210> SEQ ID NO 56
<211> LENGTH: 55
<212> TYPE: RNA

```
<213> ORGANISM: Artificial Sequence
<220> FEATURE:
<223> OTHER INFORMATION: RNA sequence of crR12

<400> SEQUENCE: 56
gaauucuacc auucaccucu uggauuuggg uauuaaagag gagaaaggua ccaug         55

<210> SEQ ID NO 57
<211> LENGTH: 55
<212> TYPE: RNA
<213> ORGANISM: Artificial Sequence
<220> FEATURE:
<223> OTHER INFORMATION: RNA sequence of taR12

<400> SEQUENCE: 57
gaauucuacc auucaccucu uggauuuggg uauuaaagag gagaaaggua ccaug         55

<210> SEQ ID NO 58
<211> LENGTH: 71
<212> TYPE: RNA
<213> ORGANISM: Artificial Sequence
<220> FEATURE:
<223> OTHER INFORMATION: RNA sequence of crR12

<400> SEQUENCE: 58
acccaaaucc aggaggugau ugguaguggu gguuaaugaa aauuaacuua cuacuaccau    60
auaucucuag a                                                        71
```

CIS/TRANS RIBOREGULATORS

RELATED APPLICATION INFORMATION

The present application claims priority to and the benefit under 35 U.S.C. 365 and 371 of International Application No.: PCT/US2003/036506 (published PCT application No. WO 2004/046321), filed Nov. 14, 2003, which claims priority to and the benefit of U.S. Provisional Application Ser. No. 60/426,891 filed Nov. 15, 2002. The entire contents of both of these applications are incorporated herein by reference.

GOVERNMENT SUPPORT

This invention was made with Government Support under Grant Number F30602-01-2-0579 awarded by the Air Force Research Laboratory and Grant Number EIA-0130331 awarded by the National Science Foundation. The Government has certain rights in the invention.

BACKGROUND OF THE INVENTION

Virtually all forms of life exhibit the ability to control gene expression, e.g., in response to environmental conditions or as part of the developmental process, and a myriad of different mechanisms for controlling gene expression exist in nature. These mechanisms permit cells to express particular subsets of genes and allow them to adjust the level of particular gene products as required. For example, bacteria and eukaryotic cells are often able to adjust the expression of enzymes in synthetic or metabolic pathways depending on the availability of substrates or end products. Similarly, many cells are able to induce synthesis of protective molecules such as heat shock proteins in response to environmental stress. Inherited or acquired defects in mechanisms for control of gene expression are believed to play a significant role in human diseases (e.g., cancer), and targeted disruption of important regulatory molecules in mice frequently results in severe phenotypic defects.

A number of approaches have been developed in order to artificially control levels of gene expression, many of which are modeled on naturally occurring regulatory systems. In general, gene expression can be controlled at the level of RNA transcription or post-transcriptionally, e.g., by controlling the processing or degradation of mRNA molecules, or by controlling their translation. For example, modulating the activity of transcription factors (e.g., by administration of small molecule activators or inhibitors) is being pursued as a method of controlling mRNA levels (see, e.g., Nyanguile O, Uesugi M, Austin D J, Verdine G L. *Proc Natl Acad Sci USA.* 1997, 94(25):13402-6. A nonnatural transcriptional coactivator.). Antisense strategies for gene silencing, in which an antisense RNA or DNA binds to a target RNA and results in inactivation, are also being actively pursued for applications ranging from functional genomics to therapeutics (Giles R V, "Antisense oligonucleotide technology: from EST to therapeutics" *Curr Opin Mol Ther.* 2000, 2(3):238-52). Nucleic acid enzymes such as ribozymes, i.e., RNA molecules that exhibit the ability to cleave other RNA molecules in a sequence-specific manner, offer another method for regulating gene expression (Sioud M., "Nucleic acid enzymes as a novel generation of anti-gene agents", *Curr Mol Med.* 2001, 1(5):575-88). More recently, the discovery of RNA interference (RNAi), in which the presence of double-stranded RNA leads to degradation of a target RNA transcript, has provided another approach to the control of gene expression (Hutvagner, G. and Zamore, P D., "RNAi: nature abhors a double-strand", *Curr. Op. Genet. Dev.*, 12:225-232, 2002).

Although the approaches described above have proven extremely valuable, they have a variety of features that limit their usefulness. For example, methods that involve alterations in RNA transcription may have slower response times than methods that are based on post-transcriptional regulation. Techniques involving modulation of transcription factors are generally limited to well-characterized transcription factors. Antisense, ribozyme, and RNAi-based approaches typically require sequence-specific design. It is evident that a need exists in the art for additional systems and methods for the control of gene expression. In particular, there exists a need for modular systems that function with a wide variety of genes and that can be integrated into biological networks. Furthermore, there exists a need in the art for systems that would afford the ability to artificially control gene expression within cells in response to external stimuli.

SUMMARY OF THE INVENTION

The present invention addresses these needs, among others, by providing systems and methods for the post-transcriptional control of gene expression in prokaryotic or eukaryotic cells. The invention provides an artificial RNA-based system that enables precise control through highly specific RNA-RNA interactions. According to the invention effective repression is achieved by engineering an RNA molecule (or template for the RNA molecule), so that the engineered RNA forms a secondary structure that prevents the ribosome from gaining access to the RNA at an appropriate location to begin translation. Repression of gene expression is achieved through the presence of a regulatory nucleic acid element (the cis-repressive RNA or crRNA) within the 5' untranslated region (5' UTR) of an mRNA molecule. The nucleic acid element forms a hairpin (stem/loop) structure through complementary base pairing. The hairpin blocks access to the mRNA transcript by the ribosome, thereby preventing translation. A small RNA (trans-activating RNA, or taRNA), expressed in trans, interacts with the crRNA and alters the hairpin structure. This alteration allows the ribosome to gain access to the region of the transcript upstream of the start codon, thereby activating transcription from its previously repressed state.

In one aspect, the invention provides an engineered nucleic acid molecule comprising: (i) a first stem-forming portion; (ii) a second stem-forming portion, wherein the two stem-forming portions are complementary or substantially complementary, and (iii) a non-stem-forming portion that forms a loop connecting the 3' end of the first stem-forming portion and the 5' end of the second stem-forming portion, wherein the engineered nucleic acid molecule forms a stem-loop structure that represses translation when positioned upstream of an open reading frame (ORF). When present as RNA, the nucleic acid molecule is referred to as a cis-repressive RNA (crRNA). The invention further provides DNA constructs and plasmids that comprise templates for transcription of a crRNA as well as cells comprising crRNA elements, DNA constructs, and plasmids.

In another aspect, the invention provides an engineered nucleic acid molecule comprising: (i) a first stem-forming portion; (ii) a second stem-forming portion; and (iii) a non-stem-forming portion, wherein the non-stem-forming portion connects the 3' end of the first stem-forming portion and the 5' end of the second stem-forming portion to form a loop, and wherein a portion of the nucleic acid molecule is complementary or substantially complementary, to a portion of a cognate cis-repressive nucleic acid molecule. When present as RNA, the nucleic acid molecule is referred to as a trans-activating RNA (taRNA). The taRNA interacts with a cognate crRNA to derepress translation that is repressed by the crRNA. The invention further provides DNA constructs and plasmids that comprise templates for transcription of a taRNA as well as cells comprising taRNA elements, DNA constructs, and plasmids.

In addition, the invention provides a system for control of gene expression comprising: (i) a first nucleic acid molecule comprising a cis-repressive sequence element upstream of an open reading frame (ORF), wherein the first nucleic acid molecule forms a stem-loop structure that represses translation of the ORF; and (ii) a second nucleic acid molecule comprising first and second stem-forming portions and a non-stem-forming portion, wherein the non-stem-forming portion connects the 3' end of the first stem-forming portion and the 5' end of the second stem-forming portion to form a loop, and wherein a portion of the second nucleic acid molecule is complementary or substantially complementary to a portion of the first nucleic acid molecule and interacts with the first nucleic acid molecule to derepress translation of the ORF.

In another aspect, the invention provides a method of regulating translation of an open reading frame comprising: (i) introducing an engineered template for transcription of an mRNA into a cell and allowing mRNA transcription to occur resulting in a transcribed mRNA, wherein the template is engineered so that the transcribed mRNA comprises first and second nucleic acid elements that form a stem-loop structure that represses translation of the mRNA; and (ii) providing an engineered nucleic acid molecule that interacts with the mRNA so as to derepress translation of the mRNA to the cell.

In certain embodiments of the invention the engineered template comprises: (i) a first stem-forming portion; (ii) a second stem-forming portion, wherein the two stem-forming portions are complementary or substantially complementary, and (iii) a non-stem-forming portion that forms a loop connecting the 3' end of the first stem-forming portion and the 5' end of the second stem-forming portion, wherein the engineered nucleic acid molecule forms a stem-loop structure that represses translation when positioned upstream of an open reading frame (ORF). In certain embodiments of the invention the engineered nucleic acid molecule comprises: (i) a first stem-forming portion; (ii) a second stem-forming portion; and (iii) a non-stem-forming portion, wherein the non-stem-forming portion connects the 3' end of the first stem-forming portion and the 5' end of the second stem-forming portion to form a loop, and wherein a portion of the nucleic acid molecule is complementary or substantially complementary, to a portion of the transcribed mRNA.

In another aspect, the invention provides a method of selecting a cognate pair of nucleic acid molecules for regulating translation comprising steps of: (i) providing one or more starting nucleic acid sequences; (ii) randomizing the sequence or sequences to generate one or more pools of randomized nucleic acid sequences; and (iii) employing in vitro selection to identify a candidate cognate nucleic acid pair comprising a repressive element that represses translation when positioned upstream of an ORF and an activating element that derepresses translation that is repressed by the candidate repressive element.

This application refers to various patents and publications. The contents of all of these are incorporated by reference. In addition, the following publications are incorporated herein by reference: *Current Protocols in Molecular Biology*, *Current Protocols in Immunology*, *Current Protocols in Protein Science*, and *Current Protocols in Cell Biology*, all John Wiley & Sons, N.Y., edition as of July 2002; Sambrook, Russell, and Sambrook, *Molecular Cloning: A Laboratory Manual*, $3^{rd}$ ed., Cold Spring Harbor Laboratory Press, Cold Spring Harbor, 2001.

BRIEF DESCRIPTION OF THE DRAWING

FIG. 9A shows flow cytometry (expression) results for pZE21G (control).

FIG. 9B shows flow cytometry (expression) results for pZE21βG (control), where β-cis sequence is inserted directly upstream of ribosome binding site (RBS) sequence. This results in a high expression state.

FIG. 9C shows flow cytometry (expression) results for the structure with one cis-repressive element (pZE21α10LG), resulting in a low expression state.

FIG. 9D shows flow cytometry (expression) results for a structure in which the mRNA transcript contains both α and β elements (pZE21βα10LG), exhibiting an intermediate expression state.

DETAILED DESCRIPTION OF CERTAIN PREFERRED EMBODIMENTS OF THE INVENTION

I. Definitions

Figure 1A:
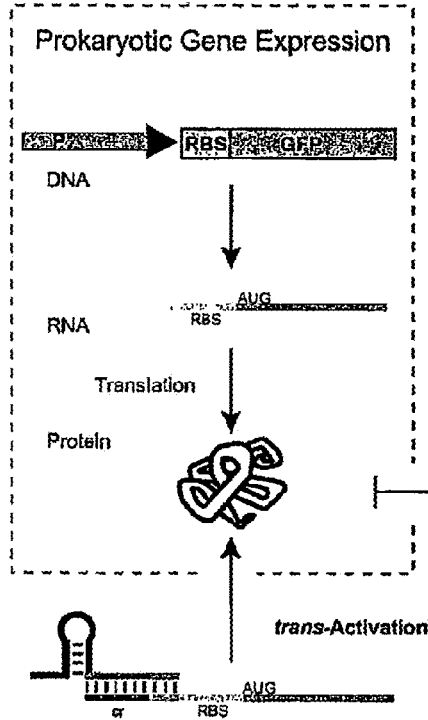
FIG. 1A illustrates the artificial riboregulator system used to control post-transcriptional regulation. Basic steps of native prokaryotic gene expression are illustrated in the box. A promoter, P, drives the expression of a gene (GFP). After transcription, mRNA is present with a ribosome binding site (RBS) available for docking by a ribosome. After ribosome binding, translation of a functional protein occurs.

The following definitions are of use in understanding the invention.

Approximately: As used herein, the terms approximately or about in reference to a number are generally taken to include numbers that fall within a range of 5% in either direction (greater than or less than) the number unless otherwise stated or otherwise evident from the context (except where such number would exceed 100% of a possible value). Where ranges are stated, the endpoints are included within the range unless otherwise stated or otherwise evident from the context.

Artificial, Engineered, Synthetic: A nucleic acid molecule is referred to herein as "artificial", "engineered", or "synthetic" if it has been created or modified by the hand of man (e.g., using recombinant DNA technology) or is derived from such a molecule (e.g., by transcription, translation, etc.) A nucleic acid molecule may be similar in sequence to a naturally occurring nucleic acid but typically contains at least one artificially created insertion, deletion, inversion, or substitution relative to the sequence found in its naturally occurring counterpart. A cell that contains an engineered nucleic acid is considered to be an engineered cell.

Complementarity: For purposes of the present invention, complementarity of two sequences is determined by dividing the total number of nucleotides that participate in complementary base pairs (GC, AU, AT) when the sequences are aligned to produce the maximum number of complementary base pairs, counting all nucleotides in the two sequences including those in bulges, mismatches, or inner loops by the total number of nucleotides contained in both sequences. For example, consider two sequences of 19 and 20 nucleotides in length in which alignment to produce the maximum number of complementary base pairs results in 16 base pairs, 1 inner loop of 2 nucleotides, 1 mismatch, and 1 bulge (in the sequence with 20 nucleotides). The percent complementarity of the two sequences is [(16+17)/39]100. It will be appreciated that complementarity may be determined with respect to the entire length of the two sequences or with respect to portions of the sequences.

Gene: For the purposes of the present invention, the term "gene" has its meaning as understood in the art. In general, a gene is taken to include gene regulatory sequences (e.g., promoters, enhancers, etc.) and/or intron sequences, in addition to coding sequences (open reading frames). It will further be appreciated that definitions of "gene" include references to nucleic acids that do not encode proteins but rather encode functional RNA molecules such as tRNAs. For the purpose of clarity we note that, as used in the present application, the term "gene" generally refers to a portion of a nucleic acid that encodes a protein; the term may optionally encompass regulatory sequences. This definition is not intended to exclude application of the term "gene" to non-protein coding expression units but rather to clarify that, in most cases, the term as used in this document refers to a protein coding nucleic acid.

Gene product or expression product: A "gene product" or "expression product" is, in general, an RNA transcribed from the gene or a polypeptide encoded by an RNA transcribed from the gene. Thus a regulatory element, environmental condition, stimulus, etc., that alters the level of transcription or the stability of an RNA transcribed from a gene or alters its ability to serve as a template for translation will be said to alter expression of the gene. Similarly, a regulatory element, environmental condition, stimulus, etc., that alters the level of translation or stability of a polypeptide translated from an RNA transcribed from the gene will be said to alter expression of the gene.

Hairpin: A "hairpin" or "stem/loop" structure as used herein refers to a single nucleic acid molecule or portion thereof that includes a duplex (double helical) region (the stem) formed when complementary regions within the molecule hybridize to each other via base pairing interactions and further includes a single-stranded loop at one end of the duplex. FIGS. 4A-4D show various stem-loop structures. In various embodiments of the invention the double-stranded portion may include one or more mismatches, bulges, or inner loops. For purposes of description herein, the length of a stem is measured from the first pair of complementary nucleotides to the last pair of complementary bases and includes mismatched nucleotides (e.g., pairs other than AT, AU, GC), nucleotides that form a bulge, or nucleotides that form an inner loop.

It is noted that although a hairpin is formed from a single nucleic acid molecule, the two portions of the molecule that form the duplex portion of the hairpin, i.e., the stem, will be referred to herein as "strands". Thus the stem may be referred to herein as the double-stranded portion of the hairpin. Nucleic acid molecules containing complementary regions that form a duplex are said to be "self-complementary" or to "self-hybridize". In general, the hairpin and intermolecular duplexes described herein form at and are stable under physiological conditions, e.g., conditions present within a cell (e.g., conditions such as pH, temperature, and salt concentration). Such conditions include a pH between 6.8 and 7.6, more preferably approximately 7.4. Typical temperatures are approximately 37° C., although it is noted that prokaryotes and certain eukaryotic cells such as fungal cells can grow at lower (or, in some cases, higher) temperatures.

As mentioned above, the stem may include one or more areas of non-complementarity, e.g., one or more mismatches, bulges, inner loops, or combinations of the foregoing. A mismatch occurs when the two strands include a single non-complementary nucleotide at corresponding positions that interrupt the continuity of the double-stranded portion (see FIG. 4B) A bulge occurs when one of the two strands includes one or more "extra" nucleotide(s) that do not base pair with nucleotide(s) on the other strand but are surrounded by regions of double-strandedness (see, e.g., FIG. 4C). An inner loop occurs when two or more consecutive mismatches exist in a stem, i.e., there are distinct complementary base pairs on either side of the inner loop (see, e.g., FIG. 4D). An inner loop is to be distinguished from a "main loop" in that in the case of an inner loop, the two strands of the loop connect distinct base pairs, whereas in the case of a main loop, the single strand of the loop connects the two nucleotides of a single base pair. Various combinations of these types of areas of non-complementarity can also exist (see, e.g., FIG. 4E).

Isolated: As used herein, "isolated" means 1) separated from at least some of the components with which it is usually associated in nature; 2) prepared or purified by a process that involves the hand of man; and/or 3) not occurring in nature. The nucleic acid molecules of the invention may be isolated nucleic acid molecules.

Nucleic acid molecule: "Nucleic acid molecule" or "polynucleotide" refers to a polymer of nucleotides joined by phosphodiester bonds. The term includes deoxyribonucleic acids (DNA) and ribonucleic acids (RNA), including messenger RNA (mRNA), transfer RNA (tRNA), etc. Typically, a nucleic acid molecule comprises at least three nucleotides. Nucleic acid molecules may be single stranded, double stranded, and also tripled stranded. A double stranded nucleic acid may comprise two separate strands of nucleic acid hybridized to each other through hydrogen bond-mediated base pairing interactions. A double stranded nucleic acid may also comprise two regions of a single nucleic acid molecule that hybridize to each other to form secondary structure, e.g, a stem in a stem-loop (hairpin) structure.

A nucleotide consists of a nucleoside, i.e., a nitrogenous base linked to a pentose sugar, and one or more phosphate groups which is usually esterified at the hydroxyl group attached to C-5 of the pentose sugar (indicated as 5') of the nucleoside. Such compounds are called nucleoside 5'-phosphates or 5'-nucleotides. In a molecule of DNA the pentose sugar is deoxyribose, whereas in a molecule of RNA the pentose sugar is ribose. The nitrogenous base can be a purine such as adenine or guanine, or a pyrimidine such as cytosine, thymine (in deoxyribonucleotides) or uracil (in ribonucleotides). Thus, the major nucleotides of DNA are deoxyadenosine 5'-triphosphate (dATP), deoxyguanosine 5'-triphosphate (dGTP), deoxycytidine 5'-triphosphate (dCTP), and deoxythymidine 5'-triphosphate (dTTP). The major nucleotides of RNA are adenosine 5'-triphosphate (ATP), guanosine 5'-triphosphate (GTP), cytidine 5'-triphosphate (CTP) and uridine 5'-triphosphate (UTP). In general, stable base pairing interactions occur between adenine and thymine (AT), adenine and uracil (AU), and guanine and cytosine (GC). Thus adenine and thymidine, adenine and uracil, and guanine and cytosine (and the corresponding nucleosides and nucleotides) are referred to as complementary.

In general, one terminus of a nucleic acid molecule has a 5'-hydroxyl group and the other terminus of the molecule has a 3'-hydroxyl group; thus the nucleotide chain has a polarity. By convention, the base sequence of a nucleic acid molecule is written in a 5' to 3' direction, which is also the direction in which RNA transcription occurs. Thus in general a DNA sequence presented herein will have the same sequence as an RNA transcribed using the DNA as a template, i.e., the sequence of the non-template DNA strand will be given.

In various embodiments of the invention a nucleic acid molecule may include nucleoside analogs (e.g., 2-aminoadenosine, 2-thiothymidine, inosine, pyrrolo-pyrimidine, 3-methyl adenosine, C5-propynylcytidine, C5-propynyluridine, C5-bromouridine, C5-fluorouridine, C5-iodouridine, C5-methylcytidine, 7-deazaadenosine, 7-deazaguanosine, 8-oxoadenosine, 8-oxoguanosine, O(6)-methylguanine, and 2-thiocytidine), chemically modified bases, biologically modified bases (e.g., methylated bases), intercalated bases, modified sugars (e.g., 2'-fluororibose, ribose, 2'-deoxyribose, arabinose, and hexose), or modified phosphate groups (e.g., phosphorothioates and 5'-N-phosphoramidite linkages).

A nucleic acid molecule or portion thereof may also be referred to as a "nucleic acid segment", a "nucleic acid element", or a "nucleic acid sequence".

Operably linked: As used herein, "operably linked" refers to a relationship between two nucleic acid sequences wherein the expression of one of the nucleic acid sequences is controlled by, regulated by, modulated by, etc., the other nucleic acid sequence. For example, the transcription of a nucleic acid sequence is directed by an operably linked promoter sequence; post-transcriptional processing of a nucleic acid is directed by an operably linked processing sequence; the translation of a nucleic acid sequence is directed by an operably linked translational regulatory sequence; the transport or localization of a nucleic acid or polypeptide is directed by an operably linked transport or localization sequence; and the post-translational processing of a polypeptide is directed by an operably linked processing sequence. Preferably a nucleic acid sequence that is operably linked to a second nucleic acid sequence is covalently linked, either directly or indirectly, to such a sequence, although any effective three-dimensional association is acceptable.

Purified: As used herein, "purified" means separated from many other compounds or entities. A compound or entity may be partially purified, substantially purified, or pure, where it is pure when it is removed from substantially all other compounds or entities, i.e., is preferably at least about 90%, more preferably at least about 91%, 92%, 93%, 94%, 95%, 96%, 97%, 98%, 99%, or greater than 99% pure.

Regulatory sequence or element: The term regulatory sequence is used herein to describe a region of nucleic acid sequence that directs, enhances, or inhibits the expression (e.g., transcription, translation, processing, etc.) of sequence(s) with which it is operatively linked. The term includes promoters, enhancers and other transcriptional control elements. The term additionally encompasses the cis and trans riboregulators of the invention. In some embodiments of the invention, regulatory sequences may direct constitutive expression of a nucleotide sequence; in other embodiments, regulatory sequences may direct tissue-specific and/or inducible or repressible expression.

Small molecule: As used herein, the term "small molecule" refers to organic compounds, whether naturally-occurring or artificially created (e.g., via chemical synthesis) that have relatively low molecular weight and that are not proteins, polypeptides, or nucleic acids. Typically, small molecules have a molecular weight of less than about 1500 g/mol. Also, small molecules typically have multiple carbon-carbon bonds.

Substantially complementary: Two sequences are considered "substantially complementary" herein if their complementarity is at least 50%.

Vector: In general, the term vector refers to a nucleic acid molecule capable of mediating entry of, e.g., transferring, transporting, etc., a second nucleic acid molecule into a cell. The transferred nucleic acid is generally linked to, e.g., inserted into, the vector nucleic acid molecule. A vector may include sequences that direct autonomous replication, or may include sequences sufficient to allow integration into host cell DNA. Useful vectors include, for example, plasmids (typically DNA molecules although RNA plasmids are also known), cosmids, and viral vectors.

II. Overview

Traditionally, most RNA molecules have been thought to be critical messengers of information from genes to the proteins they encode (1, 2). RNA also serves in other diverse roles within the cell, namely protein synthesis, RNA splicing and editing, rRNA modification, and more (1, 2). In addition, small RNAs (sRNA) can act as ribozymes (3-5), in which RNA catalyzes biochemical reactions, and as regulators that control the translation and degradation of messengers. These sRNAs, or noncoding RNAs (ncRNA), are involved in various structural, regulatory, and enzymatic capacities (6). Noncoding RNAs, which likely operate as key regulators in prokaryotic and eukaryotic cellular networks, were first identified in studies describing the plasmid-encoded antisense RNAs in bacteria (7, 8) and developmental mutants in *Caenorhabditis elegans* (9). It has recently been shown that RNA sequences can act as environmental sensors of vitamin cofactors and temperature, enabling them to directly regulate gene expression (10-16). In general, regulatory RNAs act by using base complementarity or sensing environmental cues to either repress or, more rarely, activate (17) translation. Such natural mechanisms, which target post-transcriptional regulation, provide a basis for the development of synthetic RNA regulators (riboregulators).

Its diverse structure, mode of action, and broad utility in nature contribute to the multifaceted abilities of RNA, particularly its role as a regulator of cell behavior. In vitro selection of nucleic acids has yielded novel molecules that exhibit desired catalytic, structural, and complementary base pairing properties (18-25). By exploiting these attributes, RNA can be used to direct complex interactions, such as the ability to control a target gene. Numerous strategies of RNA-mediated silencing of gene expression have been used in prokaryotes, involving gene knockout techniques, deletions, point mutations (26-29), and an antisense-based technology that identifies gene targets for antibiotic discovery (30). The present invention utilizes RNA's versatility to control post-transcriptional gene regulation through both repression and activation.

The present invention provides systems and methods for the post-transcriptional control of gene expression in prokaryotic or eukaryotic cells. The invention provides an artificial RNA-based system that enables precise control through highly specific RNA-RNA interactions. In contrast to existing engineered post-transcriptional schemes in bacteria, where repression is achieved through antisense RNA or trans-acting ribozymes (31, 32), according to the present invention effective repression is achieved by engineering an RNA molecule (or template for the RNA molecule), so that the engineered RNA forms a secondary structure that prevents the ribosome from gaining access to the RNA at an appropriate location to begin translation.

The invention employs RNA molecules both as gene silencers and activators. Repression of gene expression is achieved through the presence of a regulatory nucleic acid element (the cis-repressive RNA or crRNA) within the 5' untranslated region (5' UTR) of an mRNA molecule. The nucleic acid element forms a hairpin (stem-loop) structure through complementary base pairing. (See FIG. 4 for examples of various stem-loop structures). The hairpin blocks access to the mRNA transcript by the ribosome, thereby preventing translation. In particular, in embodiments of the invention designed to operate in prokaryotic cells, the stem of the hairpin secondary structure sequesters the ribosome binding site (RBS). In embodiments of the invention designed to operate in eukaryotic cells, the stem of the hairpin is positioned upstream of the start codon, anywhere within the 5' UTR of an mRNA.

According to the invention a small RNA (trans-activating RNA, or taRNA), expressed in trans, interacts with the crRNA and alters the hairpin structure. This alteration allows the ribosome to gain access to the region of the transcript upstream of the start codon, thereby activating transcription from its previously repressed state. Corresponding pairs of crRNA and taRNA elements (i.e., pairs in which the taRNA interacts with the crRNA to relieve repression of translation) are referred to as cognate pairs. In general, such cognate pairs include complementary or, preferably, substantially complementary portions at least 6 nucleotides in length, preferably between 6 and 50 nucleotides in length, e.g., between 12 and 40 nucleotides in length, between 20 and 30 nucleotides in length, inclusive. In order to facilitate understanding of the invention, the following section briefly describes certain aspects of the process of gene expression in prokaryotes and eukaryotes. The design and features of the cis-repressive and trans-activating nucleic acid molecules of the invention are then described in further detail.

III. Translation in Prokaryotes and Eukaryotes

FIG. 1A illustrates the basic steps of native prokaryotic gene expression (65). As shown in the figure, a promoter, P, drives the expression of a gene (the gene that encodes GFP is used for illustrative purposes). In prokaryotes, gene expression begins when RNA polymerase recognizes and binds to sequences (−35 and −10 consensus sequences) present in a promoter region of the bacterial DNA (or in an extrachromosomal element such as a DNA plasmid). Transcription begins at the start site, which is located a short distance downstream of (i.e., in the 3' direction from) the binding site and generally terminates when a stop (termination) signal is encountered. After transcription, mRNA is present with a ribosome binding site (RBS) available for docking by a ribosome in the 5' UTR. Naturally occurring ribosome binding sites typically comprise a sequence referred to as the Shine-Dalgarno sequence typically about six nucleotides long (although shorter and longer sequences exist), which can occur at several places in the same mRNA molecule. These sequences are generally located four to seven nucleotides upstream from a start codon, and they form base pairs with a specific region of the rRNA in a ribosome to signal the initiation of protein synthesis at this nearby start codon. The small (30S) ribosomal subunit recognizes the RBS and forms an initiation complex along with a tRNA having an anticodon (e.g., UAC) complementary to the start codon (e.g., AUG) and carrying an altered form of the amino acid methionine (N-formylmethionine, or f-Met) and protein initiation factors. The initiation process establishes the correct reading frame for synthesis of a functional protein. Activity of a RBS may be influenced by the length and nucleotide composition of the spacer which separates the RBS and the initiator (AUG) (62). Prokaryotic mRNAs may contain multiple ribosome binding sites, each upstream of a start codon, resulting in synthesis of a number of different polypeptides from a single mRNA (i.e., the mRNA is polycistronic).

Following binding of the small ribosomal subunit, initiation factors that were associated with the small ribosomal subunit depart, and a large (50S) ribosomal subunit attaches to form the 70S ribosome. Since the initiator tRNA molecule is bound to the ribosome, synthesis of a protein chain can commence with the binding of a second aminoacyl-tRNA molecule to the ribosome. As new peptide bonds are formed in the elongation phase of protein synthesis, the ribosome moves along the mRNA, making way for entry of the next ribosome upstream of the start codon. Elongation typically continues until the ribosome encounters a stop codon, at which point the ribosome releases the mRNA and disocciates.

Protein synthesis in eukaryotes occurs by a broadly similar process, with some significant differences. Eukaryotic mRNAs typically undergo a variety of modifications in the nucleus prior to exit into the cytoplasm. In particular, most eukaryotic mRNAs are modified by the addition of a "cap" structure composed of a 7-methylguanosine residue linked to a triphosphate at the 5' end. This 5' cap structure plays an important role in protein synthesis. Unlike the case in prokaryotes, where correct positioning of the small ribosomal subunit depends on binding to the RBS, in eukaryotic cells the small ribosomal subunit first binds at the 5' end of an mRNA chain in a process that involves recognition of the 5' cap. The small subunit then moves along the mRNA in a 3' direction, searching for an AUG codon. Typically the first AUG codon is selected, although a few nucleotides in addition to the AUG are also important for the selection process. Although the most efficiently used AUG triplets are embedded within a sequence (referred to as a Kozak consensus sequence) such as ACCAUGG or GCCG/ACC AUGC (SEQ ID NO:1) (the initiation codon is underlined) almost any AUG can be used (55-61).

In most cases, once a start codon near the 5' end of an mRNA has been selected, downstream AUGs will not serve as sites for the initiation of protein synthesis unless the mRNA contains an internal ribosome binding site (IRES). However, an IRES positioned 5' to an additional coding sequence directs the co-translation of multiple open reading frames (ORF) from a single polycistronic RNA message. Briefly, IRES are cis-acting elements that recruit the small ribosomal subunits to an internal initiator codon in the mRNA with the aid of cellular trans-acting factors (for a review, see 52). A polycistronic message having correctly positioned IRES sequences directs the co-translation of multiple ORFs in a polycistronic mRNA.

IV. Design of Cis-Repressive Sequence and Cis-Repressive RNA Elements

This section describes the design of cis-repressive sequences and RNA elements that contain them (cis-repressive RNA) and the construction of templates for their synthesis. For purposes of convenience in the description, references to nucleic acid elements such as start codons, ribosome binding site, 5' UTR, stem-loop, etc., may refer to either the RNA form or to the DNA form (i.e., to a DNA molecule that provides a template for transcription of the RNA). Similarly, when reference is made to modifying an RNA (e.g., by inserting an element such as a cis-repressive sequence) into the RNA, it is to be understood that the modification is generally accomplished by engineering the appropriate modification to a DNA molecule that provides a template for transcription of the RNA.

In both prokaryotic and eukaryotic systems, the ribosome must be able to gain access to the start codon. The major start codon is AUG, although the minor start codons GUG, AUC, and UUG are sometimes used, typically in prokaryotes (53, 65). In prokaryotes, the small ribosomal subunit must be able to bind to the RBS, while in eukaryotes the small ribosomal subunit must be able to progress in a 3' direction from the 5' end of the mRNA until it encounters the start codon or must be able to bind to the IRES. A variety of naturally occurring regulatory systems control translation by interfering with these processes (e.g., 14, 17, 31, 43). The inventors have recognized that mechanisms similar to those involved in naturally occurring regulatory processes, e.g., formation and disruption of RNA secondary structures, may be employed to afford control over gene expression. In particular, the inventors have designed nucleic acid elements that can be inserted into an RNA transcript (e.g., via insertion into a template for synthesis of the RNA transcript), so that the resulting RNA molecule assumes a hairpin (stem/loop) secondary structure that prevents access to the appropriate portion of the transcript by the small ribosomal subunit.

For purposes of illustration, a riboregulator system for use in prokaryotic cells will first be described. Differences for eukaryotic systems are described below. It will be assumed herein that the start codon is AUG, but it is to be understood that the invention can be modified to operate in an essentially identical manner with alternate start codons such as GUG, UUG, or AUC, simply by replacing AUG by GUG, UUG, or AUC (or, in DNA, replacing ATG by GTG, TTG, or ATC) and, in those embodiments of the invention in which the start codon forms part of the crRNA stem, by changing the sequences of complementary nucleic acids appropriately.

A. Cis-Repressive Sequence

Figure 1B:
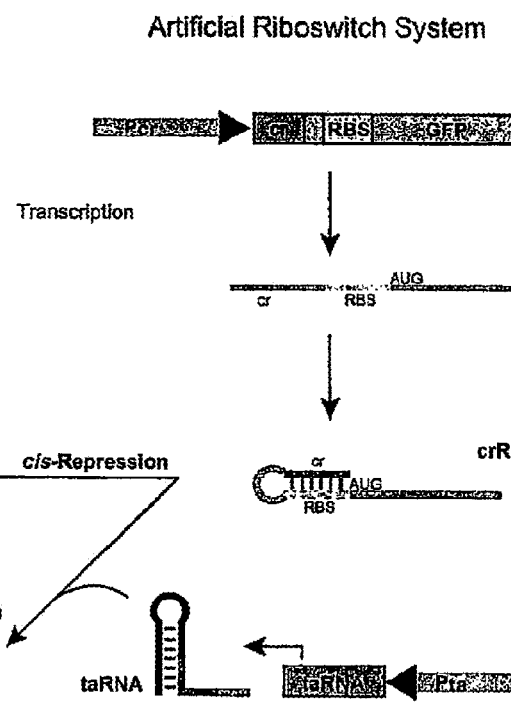
FIG. 1B schematically illustrates the functioning of the cis-repressive and trans-activating riboregulators in a prokaryotic system.

As shown in FIG. 1B, in the artificial riboregulator, a small sequence, referred to as the cis-repressive sequence (cr), complementary to the RBS, is cloned downstream of the promoter ($P_{cr}$) and upstream of the RBS. The cis-repressive sequence may, but need not, replace part or all of the endogenous sequence of a 5'UTR. Thus addition of the cis-repressive sequence may occur by insertion and/or substitution. Addition of the cis-repressive sequence therefore may, but need not, alter the length of the 5' UTR. In general, the cis-repressive sequence may be located at the 5' end of the UTR, or the 5' portion of the UTR upstream of the cis-repressive sequence can be of any length, e.g., at least 2 nucleotides, at least 4 nucleotides, at least 5 nucleotides, at least 10 nucleotides, at least 25 nucleotides, at least 50 nucleotides, etc. In addition, there may be one or more ORFs upstream of the cis-repressive sequence. Following transcription, a hairpin is formed within the 5'UTR of the mRNA, which blocks ribosome docking and translation (cis-repression), as shown in FIG. 1. An RNA molecule comprising a cis-repressive sequence and further comprising various additional elements discussed below is referred to as a cis-repressive RNA (crRNA).

According to an additional aspect of the invention described in more detail below, a second promoter, $P_{ta}$, expresses a small, non-coding RNA (trans-activating RNA, taRNA) that targets the crRNA with high specificity. The taRNA and crRNA undergo a linear-loop interaction that exposes the obstructed RBS and permits activation of expression by allowing translation to occur. FIGS. 2 and 3 show additional crRNA and taRNA structures that were constructed. A comparison of the repressive and activating abilities of these structures allowed the inventors to refine the basic structure of the crRNA and taRNA to optimize their activities.

Figures 3A, 3B, 3C, 3D, 3E, 3F, 3G:
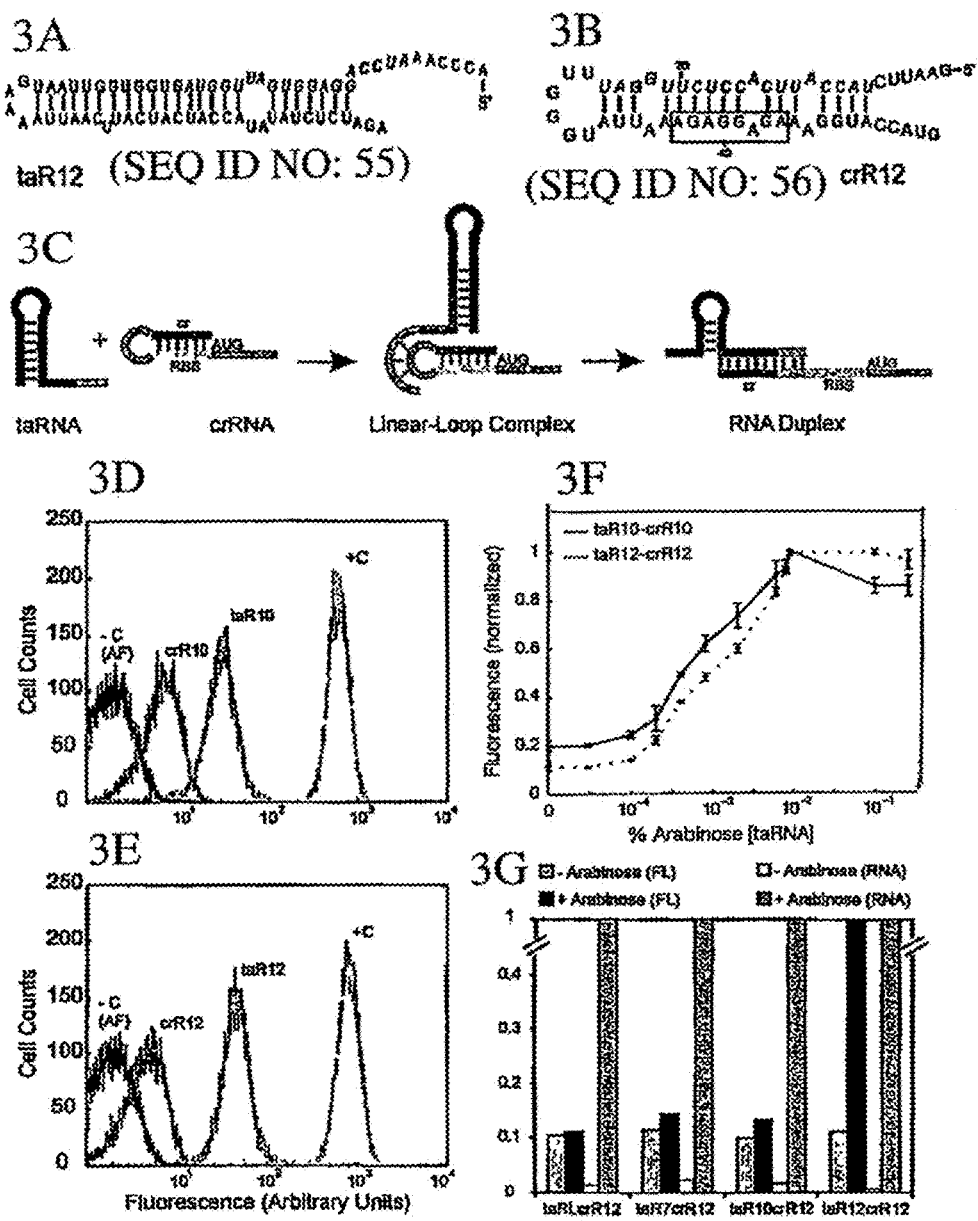
FIGS. 3A and 3B show M-fold predicted (35) structures of taR12 (FIG. 3A) and crR12 (FIG. 3B) variants using the same scheme as FIG. 2. As in FIG. 2A, the ribosome binding site (RBS) is boxed; YUNR recognition motif of loop in light grey; cis-repressive (cr) sequence in italics; start codon (AUG) in bold for crRNA.
FIG. 3C shows a schematic representation of the proposed mechanism for artificial riboswitch. The YUNR motif (medium grey) of taRNA targets its complementary sequence (medium grey) on crRNA. The linear-loop complex formed by taRNA-crRNA interaction, destabilizes the hairpin stem-loop which obstructs ribosomal recognition of RBS (light grey). The resulting RNA duplex exposes the RBS and allows translation to occur. (cis-repressive sequence in dark grey; start codon (AUG) noted).
FIG. 3D (trans-activation results) shows flow-cytometric results for taR10-crR10 riboregulator system. Autofluorescence measurement (–C) (cells lacking GFP) in black and GFP expression of control (+C) (cells without cis-sequence) in light grey. Intermediate grey curves depict cis-repressed cultures (labeled crR10, no arabinose) and cells containing high levels of taRNA (labeled taR10, 0.25% arabinose).
FIG. 3E (trans-activation results) shows flow-cytometric results for taR12-crR12 riboregulator system. Autofluorescence measurement (–C) (cells lacking GFP) in black and GFP expression of control (+C) (cells without cis-sequence) in light grey. Intermediate grey curves depict cis-repressed cultures (labeled crR12, no arabinose) and cells containing high levels of taRNA (labeled taR12, 0.25% arabinose).
FIG. 3F (trans-activation results) shows normalized dose-response curves of taR10-crR10 (solid line) and taR12-crR12 (dotted line) riboswitches at corresponding concentrations of arabinose.
FIG. 3G (trans-activation results) shows flow-cytometry (grey & black bars) and taRNA concentration (white & striated bars) results of four riboregulator variants (taRL-crR12, taR7-crR12, taR10-crR12, taR12-crR12) at low (grey and white, respectively) and high (black and striated, respectively) arabinose concentrations. All data presented is normalized to high GFP and RNA levels.

As shown in FIGS. 1 and 3C (left portion, labeled crRNA) the presence of an engineered cis-repressive sequence (cr) upstream of the start codon in an mRNA results in formation of a double-stranded stem-loop (hairpin) structure that prevents the ribosome from gaining access to the appropriate location on the mRNA from which to initiate translation from the downstream start codon. As described in Example 1, the presence of a cis-repressive sequence dramatically reduces translation relative to that which occurs when a sequence that does not form such a hairpin is positioned upstream of the start codon in an mRNA. Example 1 describes construction of crRNA elements comprising cis-repressive sequences and their insertion into a DNA construct under control of (i.e., in operable association with) an inducible promoter and upstream of an open reading frame that encodes a reporter molecule (green fluorescent protein). Measurement of the activity of the reporter (fluorescence) provides a measure of the translation of the mRNA.

Table 1 presents data showing that insertion of cis-repressive sequence present in crRNA structures crRL, crR7, crR10, and crR12 repressed translation by >96% at intermediate levels of transcription of the mRNA comprising the sequence and by >97% at high transcription levels. It is noted that this level of post-transcriptional repression exceeds that achieved heretofore using antisense RNA provided in trans. Thus in certain preferred embodiments of the invention translation is repressed by at least 70%, at least 80%, at least 90%, or at least 95%. (Note that in Table 1 the % complementarity was calculated by computing the total number of matches between the nucleotides in the cis-repressive sequence and the corresponding sequences (i.e., the total number of matches in the stem) divided by the total length of the stem.) In the calculations presented in Table 1, background autofluorescence was not subtracted from the values obtained in the repressed and non-repressed states. Subtracting this background results in a more accurate computation of the actual degree of repression. When background autofluorescence was subtracted, crRNA structures crRL, crR7, crR10, and crR12 repressed translation by >98% at intermediate or high levels of transcription of the mRNA comprising the sequence.

TABLE 1

Percent (%) Sequence Complementarity of Cis Element to the RBS. Predicted $\Delta G_{MFOLD}$ (35, 46) obtained from the MFOLD server. Concentrations of mRNA obtained from competitive PCR coupled with MALDI-TOF mass spectrometry are internally normalized to 16S rRNA levels within each sample. FL1 values represent measured GFP expression levels (arbitrary units) obtained by flow cytometry. RNA and FL1 normalized values represent each sample normalized to the control (crRNA/C), which lacks the cis sequence. Fold induction (+aTc/−aTc) depicts the change in RNA and FL1 levels between high and low transcription rates within each column.

|  |  | Control | crRL | crR7 | crR10 | crR12 |
|---|---|---|---|---|---|---|
| % RBS Sequence Complementarity |  | — | 100 | 89 | 84 | 84 |
| $\Delta G_{MFOLD}$ (kcal/mol) |  | −4.6, −4.8 | −27.6 | −23.7 | −16 | −15.6 |
| −AtC: | mRNA[1] | 0.364 ± .077 | 0.135 ± .014 | 0.154 ± .022 | 0.152 ± .022 | 0.144 ± .033 |
|  | RNA normalized | 1 | .37 | .42 | .42 | .40 |
|  | FL1 | 113.10 ± 15.8 | 2.55 ± .02 | 3.75 ± .19 | 3.41 ± .03 | 2.91 ± .05 |
|  | FL1 normalized | 1 | 0.022 | 0.033 | 0.030 | 0.026 |

TABLE 1-continued

Percent (%) Sequence Complementarity of Cis Element to the RBS. Predicted $\Delta G_{MFOLD}$ (35, 46) obtained from the MFOLD server. Concentrations of mRNA obtained from competitive PCR coupled with MALDI-TOF mass spectrometry are internally normalized to 16S rRNA levels within each sample. FL1 values represent measured GFP expression levels (arbitrary units) obtained by flow cytometry. RNA and FL1 normalized values represent each sample normalized to the control (crRNA/C), which lacks the cis sequence. Fold induction (+aTc/−aTc) depicts the change in RNA and FL1 levels between high and low transcription rates within each column.

|  |  | Control | crRL | crR7 | crR10 | crR12 |
|---|---|---|---|---|---|---|
| +aTc: | mRNA[1] | 1.53 ± .176 | 0.611 ± .113 | 0.629 ± .043 | 0.628 ± .096 | 0.540 ± .098 |
|  | RNA normalized | 1. | .40 | .40 | .41 | .35 |
|  | FL1 | 640.5 ± 25 | 4.06 ± .19 | 13.61 ± 1.12 | 10.05 ± .12 | 6.55 ± .14 |
|  | FL1 normalized | 1 | 0.006 | 0.021 | 0.016 | 0.010 |
| +aTc | RNA | 4.2 | 4.5 | 4.1 | 4.1 | 3.8 |
| −aTc | FL1 | 5.7 | 1.6 | 3.6 | 2.9 | 2.2 |

In certain preferred embodiments of the invention the hairpin stem formed by base pairing between the cis-repressive sequence and sequences between the 3' end of the cis-repressive sequence and the 5' end of the ORF is at least 4 nucleotides in length, e.g., between 4 and approximately 100 nucleotides in length. In certain embodiments of the invention the stem is between approximately 6 and 50 nucleotides in length. In certain embodiments of the invention the stem is between approximately 10 and 30 nucleotides in length, e.g., 15-25 nucleotides in length. In certain preferred particular embodiments of the invention the stem is 18-20 nucleotides, or 19 nucleotides in length. In general, shorter stems result in decreased repression of translation (leakiness), particularly when the stem includes one or more mismatches, bulges, or inner loops as is the case in certain preferred embodiments of the invention (see below). Thus in general increased repression may be achieved by using a longer stem length. However, in order to achieve efficient reversibility of the repression by a trans-activating RNA, it may be preferable to avoid extremely long stems. In addition, longer stems (in the absence of mismatches, bulges, or inner loops, may activate RNAse III (in prokaryotes) or the interferon response (in mammals) or similar responses in other eukaryotes such as plants, leading to undesired degradation of the transcript. Furthermore, for certain applications it may be desirable to utilize a cis-repressive sequence that offers less than the maximum obtainable degree of repression. For example, to determine gene dosage effects it may be preferable to achieve a "knock-down" rather than a "knock-out" of gene expression. It is noted that in certain embodiments of the invention the hairpin stem formed by base pairing between the cis-repressive sequence and sequences between the 3' end of the cis-repressive sequence and the 5' end of the ORF may also include a portion of the 5' end of the ORF. In other words, the sequence at the 5' end of the cis-repressive sequence, or the sequence upstream of the cis-repressive sequence may be complementary or substantially complementary to a portion of the downstream ORF.

In prokaryotes the hairpin stem preferably encompasses part or, more preferably all, of the ribosome binding site. Thus the sequence of the cis-repressive sequence is complementary, or, preferably, substantially complementary to the RBS sequence. In certain embodiments of the invention the cis-repressive sequence is at least 66% complementary to the RBS. In other embodiments of the invention the cis-repressive sequence is at least 75%, at least 80%, at least 85%, at least 90%, or at least 95% complementary to the RBS. In certain embodiments of the invention the cis-repressive sequence and the RBS display between 80% and 90% complementarity. While not wishing to be bound by any theory, it is likely that the presence of one or more mismatches, bulges, or inner loops in the duplex formed by the cis-repressive sequence and the RBS decreases the stability of the duplex, which increases the likelihood that the duplex region will undergo a conformational change in the presence of a cognate taRNA (see below) so that derepression of translation can occur.

In eukaryotes the hairpin may be located anywhere within the 5' UTR upstream of the start codon (or, in the case of an mRNA that includes an IRES, anywhere between the IRES and the start codon), or may include a small portion of the 5' region of the ORF. In eukaryotes the most 3' nucleotide in the hairpin stem is preferably located within 100 nucleotides of the start codon, more preferably within 50 nucleotides of the start codon, more preferably within 20 nucleotides of the start codon. In certain embodiments of the invention the hairpin stem encompasses part or all of a Kozak consensus sequence.

As mentioned above, in certain preferred embodiments of the invention the cis-repressive sequence is longer than the RBS or includes only part of the RBS, so that the hairpin stem involves one or more nucleotides between the 3' end of the cis-repressive sequence and the 5' end of the ORF in addition to, or instead of, the RBS. For example, the cis-repressive sequence may be 19 nucleotides in length, and the RBS may be 6-8 nucleotides in length, as shown in crRNA structures crRL, crR7, crR10, and crR12, shown in FIGS. 2A and 3, in which the cis-repressive sequences are in italics and the RBS sequences are boxed. In this case the hairpin stem includes additional sequences downstream of and upstream of the RBS. In certain embodiments of the invention the stem may encompass all or part of the start codon.

In general, the sequence of the cis-repressive sequence is complementary, or, preferably, substantially complementary to a portion of the sequence between the 3' end of the cis-repressive sequence and the 5' end of the ORF. In certain embodiments of the invention the cis-repressive sequence is at least 66% complementary to a portion of the sequence between the 3' end of the cis-repressive sequence and the 5' end of the ORF, equal in length to the cis-repressive sequence. In other embodiments of the invention the cis-repressive sequence is at least 75%, at least 80%, at least 85%, at least 90%, or at least 95% complementary to a portion of the sequence between the 3' end of the cis-repressive sequence and the 5' end of the ORF equal in length to the cis-repressive sequence. In certain embodiments of the invention the cis-repressive sequence and a portion of the sequence between the 3' end of the cis-repressive sequence and the 5' end of the ORF display between 80% and 90% complementarity. While not wishing to be bound by any theory, it is likely that the presence of one or more mismatches, bulges, or inner loops in the duplex formed by the cis-repressive sequence and the portion of sequence between the 3' end of the cis-repressive sequence and the 5' end of the ORF increases the likelihood that the duplex region will undergo a conformational change in the presence of a cognate taRNA (see below) so that derepression of translation can occur.

The degree of complementarity may also be considered in terms of the ratio of the number of nucleotides in complementary nucleotide pairs to the sum of the number of nucleotides that are present in mismatches, bulges, or inner loops. According to this approach, in certain embodiments of the invention a desirable ratio is between 4:1 and 8:1, or between 5:1 and 7:1, or approximately 6:1.

In addition to the absolute degree of complementarity between the cis-repressive sequence and the RBS and/or the absolute degree of complementarity between the cis-repressive sequence and a portion of the sequence between the 3' end of the cis-repressive sequence and the ORF, the nature and location of the non-complementary regions are significant. In general, the non-complementary portions of the stem may be mismatches, bulges, and/or inner loops. In preferred embodiments of the invention one or more mismatches, bulges, or inner loops exist within the stem formed by the cis-repressive sequence and a portion of the sequence between the 3' end of the cis-repressive sequence and the ORF. In certain embodiments of the invention 2, 3, 4, or 5 mismatches, bulges, or inner loops exist in this region. In general, it is preferred that a bulge comprises between 1 and 4 nucleotides, e.g., 1, 2, 3, or 4 nucleotides. In certain embodiments of the invention a bulge comprises 1 unpaired nucleotide. In general it is preferred that an inner loop comprises 5 or fewer nucleotides, e.g., 1, 2, 3, 4, or 5 nucleotides in each strand of the stem. In certain embodiments of the invention an inner loop comprises 2 nucleotides in each strand of the stem.

Figure 2A:
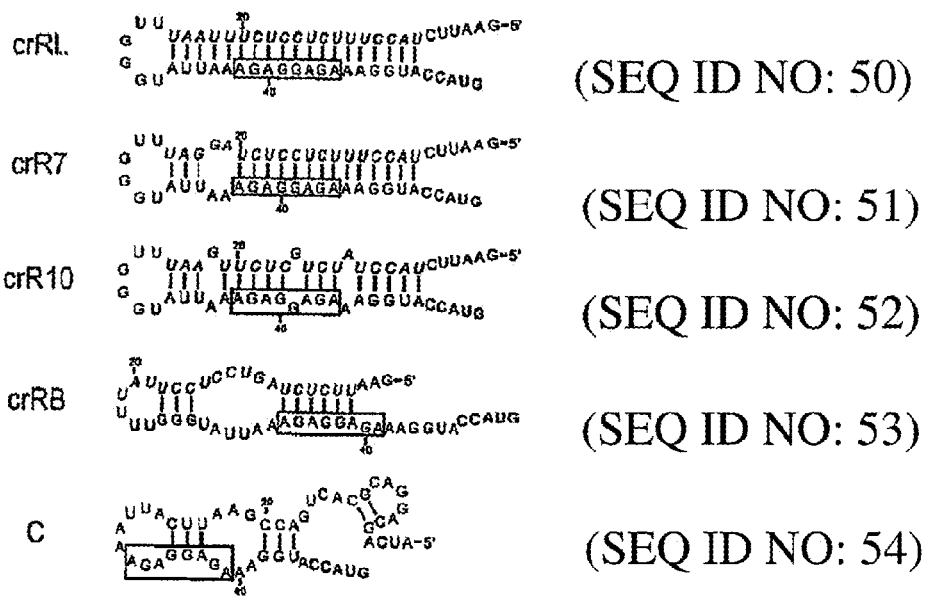
FIG. 2A illustrates M-fold (35) predicted secondary structures of four crRNA variants (in ascending gray scale) and of a control RNA with an arbitrary sequence in place of the cis-repressive sequence. crRL (lightest), crR7, crR10, crRB, and control (darkest). The ribosome binding sites (RBS) are boxed; YUNR recognition motif of loops in light grey; cis-repressive (cr) sequences in italics; start codons (AUG) in bold.

Preferably the areas of non-complementarity are dispersed at various locations within the loop. By "dispersed" is meant that at least one complementary base pair exists between any two areas of non-complementarity. In certain embodiments of the invention at least 2, at least 3, at least 4, at least 5, at least 6, at least 7, or at least 8 base pairs separate 2 or more areas of non-complementarity. It may also be desirable to have at least 2 or 3 nucleotide pairs between the areas of non-complementarity and the last base pair in the stem. For example, FIG. 2A and FIG. 3 illustrate certain preferred configurations for the areas of non-complementarity in the stems present in crR10 and crR12. Both stems contain 3 dispersed mismatches. The mismatches are separated from each other by at least 3 nucleotide pairs and the outer 2 mismatches are each positioned at least 3 nucleotide pairs away from the respective ends of the stem.

It will be evident to one of ordinary skill in the art that a variety of alternate configurations are possible without departing from the guidelines described above. In general, the key consideration is the desirability of introducing one or more areas of non-complementarity so as to confer partial instability on the stem-loop structure so that conformational change can occur in the presence of the cognate taRNA. In this regard it is noted that for purposes of the present invention all base pairings other than the cognate base pairings (AT, AU, GC) are considered mismatches. However, allowable pairings such as GU (wobble base pairs) will confer less instability than pairings such as UU, GG, etc. In general, the degree of partial instability is reflected in the change in free energy associated with folding, which can be calculated using a variety of computer programs known in the art. For example, the inventors calculated $\Delta G_{MFOLD}$ using the MFOLD program as described in Example 1.

The ability of any particular sequence to function as an effective repressor of translation may readily be tested by inserting it upstream of an RBS within a 5' UTR of a transcript of choice (e.g., one that encodes a reporter molecule) and measuring the resulting translation. Example 1 describes such measurements, in which various cis-repressive sequences were located within a larger RNA molecule (the crRNA) that can be conveniently inserted upstream of any ORF of choice.

In Example 1, GFP was used as a reporter. However, any of a wide variety of different reporters could be used, including fluorescent or chemiluminescent reporters (e.g., GFP variants, luciferase, e.g., luciferase derived from the firefly (*Photinus pyralis*) or the sea pansy (*Renilla reniformis*) and mutants thereof), enzymatic reporters (e.g., β-galactosidase, alkaline phosphatase, DHFR, CAT), etc. The eGFPs are a class of proteins that has various substitutions (e.g., Thr, Ala, Gly) of the serine at position 65 (Ser65). The blue fluorescent proteins (13FP) have a mutation at position 66 (Tyr to His mutation) which alters its emission and excitation properties. This Y66H mutation in BFP causes the spectra to be blue-shifted compared to the wtGFP. Cyan fluorescent proteins (CFP) have a Y66W (Tyr to Trp) mutation with excitation and emission spectra wavelengths between those of BFP and eGFP. Sapphire is a mutant with the excitation peak at 495 nM suppressed while still having the excitation peak at 395 and the emission peak at 511 nM. Yellow FP (YFP) mutants have an aromatic amino acid (e.g. Phe, Tyr, Trp) at position 203 and have red-shifted emission and excitation spectra.

B. Loop Sequence

The cis-repressive sequences described above may be positioned upstream of an endogenous or synthetic RBS of choice, without changing or replacing any of the sequences between the 3' end of the cis-repressive sequence and the 5' end of the ORF. In such a case the sequence of the cis-repressive sequence is selected to achieve the desired degree of complementarity in the hairpin stem, while the loop consists of whatever sequence is present between the 3' end of the cis-repressive sequence and the 5' end of the sequence with which it pairs to form the stem. In general, therefore, the length of the loop depends on the positioning of the cis-repressive sequence with respect to downstream complementary sequences. In certain preferred embodiments of the invention the length of the loop is between 3 and 15 nucleotides inclusive, between 4 and 10 nucleotides inclusive, between 4 and 8 nucleotides inclusive, or between 5 and 7 nucleotides, inclusive, e.g., 5, 6, or 7 nucleotides.

In addition, in order to achieve derepression in the presence of the cognate taRNA, in certain preferred embodiments of the invention the loop comprises a YUNR (pyrimidine-Uracil-Nucleotide-puRine) sequence, where Y stands for a pyrimidine (e.g., U or C in RNA, T or C in DNA), U stands for uracil, N stands for any nucleotide, and R stands for a purine (e.g., A or G). For example, a suitable YUNR sequence is UUGG. The YUNR sequence has been shown to be important for intermolecular RNA complex formation in the naturally occurring R1 system (34). While not wishing to be bound by any theory, it is likely that this sequence facilitates a linear-loop intermolecular interaction with a cognate taRNA that includes a nucleotide sequence complementary to the YUNR motif. The YUNR sequence may be located anywhere within the loop.

C. Cis-Repressive RNA Elements

The cis-repressive sequence and loop sequence described above may be combined to form a single RNA element which, together with additional sequences, can be positioned upstream of any ORF (e.g., either inserted into or replacing part of the 5' UTR) in order to repress translation. Such composite RNA elements are referred to herein as cis-repressive RNA (crRNA). In addition to the cis-repressive sequence and loop, a crRNA element comprises a sequence substantially complementary to the cis-repressive sequence. In implementations for prokaryotic systems, this sequence typically comprises an RBS. The crRNA thus comprises a first stem-forming portion (the cis-repressive sequence) and a second stem-forming portion, wherein the two stem-forming portions are complementary or, preferably, substantially complementary, and wherein the two stem-forming portions are connected by a non-stem-forming portion that forms a loop connecting the 3' end of the first stem-forming portion and the 5' end of the second stem-forming portion. The loop sequence preferably includes a YUNR motif. Preferred lengths of the two stem-forming portions, and preferred degrees of complementarity between the stem-forming portions are as described above for the case in which the cis-repressive sequence form a stem with sequences between the 3' end of the cis-repressive sequence and the 5' end of the ORF. Here the crRNA element provides the loop and some or all of the sequences between the 3' end of the cis-repressive sequence and the 5' end of the ORF.

The crRNA may further include a start codon, e.g., AUG. The AUG may be positioned downstream of (i.e., in a 3' direction from) the 3' end of the second stem-forming portion as shown in FIG. 3A. There may, but need not be, one or more nucleotides between the 3' end of the second complementary portion and the AUG. In other embodiments of the invention the AUG forms part of the second stem-forming portion and thus participates in formation of the stem.

In general, preferred crRNA sequences include a spacer region between the 3' end of the RBS and the start codon. In prokaryotes, presence of such a spacer contributes to a high level of translation (62). For example, as shown in FIGS. 2 and 3, the sequence AAGGUACC is present between the 3' end of the RBS and the AUG. It is noted that this sequence contains a restriction site, to facilitate cloning, although this is not required. Other restriction sites could also be used. In certain embodiments of the invention the spacer has the sequence GTTTTTACC. It has been shown that the sequence AGGAGGGTTTTTACCAUG (SEQ ID NO:2) (in which the RBS and start codon are underlined) can support a high level of translation in both prokaryotic and eukaryotic systems (61).

The crRNA may, but need not, include a single-stranded portion upstream of (i.e., in the 5' direction from) the first stem-forming portion. In crR10, for example, the single-stranded portion has the sequence GAAUUC. However, in general this portion may have any sequence, including the sequence of part or all of the 5' UTR of a gene. In general, this sequence may have any length and may represent any portion of an mRNA transcript located upstream of the RBS that is sequestered by the crRNA.

It will be appreciated that if the template for transcription of a crRNA is present within a plasmid or is integrated into the cellular genome, some or all of the crRNA elements may be provided by the plasmid or by the endogenous DNA. For example, DNA that provides a template for transcription of the first stem-forming portion and the loop may be inserted into genomic DNA upstream of an endogenous RBS. In this case some or all of the second complementary portion and the AUG will be provided by the genomic DNA.

An exemplary structure of a crRNA of the invention (crR12) is depicted in FIG. 3B. The crRNA comprises first and second substantially complementary stem-forming portions that hybridize to form a double stranded stem and an intervening non-stem-forming portion that forms a single-stranded loop joining the 3' end of the first stem-forming portion to the 5' end of the second stem-forming portion. The first stem-forming portion comprises a cis-repressive sequence, such as those described above. The stem includes 3 dispersed bulges, one of which occurs in the portion of the stem that includes the RBS. The crRNA element further includes an AUG and a short single-stranded region upstream of the AUG between the AUG and one end of the stem. In addition, the crRNA element includes a single-stranded portion at its 5' end before the beginning of the stem.

The invention therefore provides a nucleic acid molecule comprising (i) a first stem-forming portion comprising a cis-repressive sequence; (ii) a second stem-forming portion, wherein the two stem-forming portions are complementary or, preferably, substantially complementary, and (iii) a non-stem-forming portion that forms a loop connecting the 3' end of the first stem-forming portion and the 5' end of the second stem-forming portion. The loop sequence preferably includes a YUNR motif. In certain preferred embodiments of the invention a stem formed by the two stem-forming portions is between approximately 12 and 26 nucleotides in length, e.g., approximately 19 nucleotides in length. In certain preferred embodiments of the invention the complementarity of the stem-forming portions is between 75% and 95%, e.g., approximately 85%. In certain preferred embodiments of the invention the stem comprises at least 2 dispersed areas of non-complementarity, e.g., 3 areas of non-complementarity, which may be bulges, mismatches, or inner loops. In certain embodiments of the invention the second stem-forming portion comprises an RBS. In certain embodiments of the invention the second stem-forming portion comprises a Kozak consensus sequence.

It is noted that in certain embodiments of the invention the crRNA forms only a single loop in its translation-repressing configuration, unlike various naturally occurring regulatory systems in which multiple loops are formed. In addition, in certain embodiments of the invention the crRNA represses translation in the absence of a ligand.

V. Design of Trans-Activating RNA Elements

As mentioned above, in certain preferred embodiments of the invention the cis-repressive sequences and crRNA elements operate in conjunction with additional RNA elements, referred to as trans-activating RNA elements (taRNAs) that derepress translation that is repressed by the cognate cis-repressive sequence or crRNA element. As shown in FIGS. 1 and 3C, prior to interaction with the cognate cis-repressive sequence or crRNA element, the taRNA comprises first and second stem-forming portions and a non-stem-forming portion, wherein the non-stem-forming portion connects the 3' end of the first stem-forming portion and the 5' end of the second stem-forming portion to form a loop, and wherein a portion of the taRNA is complementary or, preferably, substantially complementary, to a portion of a cognate cis-repressive sequence or cognate crRNA. Preferably the first stem-forming portion comprises a portion that is complementary or substantially complementary to an RBS.

In preferred embodiments of the invention the 5' portion of the taRNA (i.e., the portion 5' of the most 5' nucleotide in the first stem-forming portion) comprises a sequence that is complementary to the sequence in the loop of a cognate crRNA. In particular, if the crRNA loop comprises a YUNR sequence, then preferably the taRNA 5' region comprises a YNAR sequence. The length of the 5' portion of the taRNA may vary. However, in certain embodiments of the invention the length of this portion is less than 100 nucleotides, less than 50 nucleotides, less than 25 nucleotides, or less than 10 nucleotides. In certain embodiments of the invention the length of the 5' portion of the taRNA is between 5 and 10 nucleotides. While not wishing to be bound by any theory, it is possible that a longer 5' portion may interfere with formation or stability of the crRNA:taRNA duplex or may impede access by the ribosome to the region upstream of the ORF, e.g., the RBS (see below for discussion of this duplex).

In preferred embodiments of the invention the first and second stem-forming portions of the taRNA form a stem that is between 6 and 100 nucleotides in length, preferably between 10 and 50 nucleotides in length, e.g., between 10 and 40, between 15 and 30 nucleotides in length, etc. For example, FIG. 3A shows a taRNA structure (taR12) in which the stem is 26 nucleotides in length. Preferably if the stem is greater than approximately 20 nucleotides in length it includes one or more mismatches, bulges, or inner loops. For example, taR12 (see FIG. 3A) includes a two nucleotide inner loop and a bulge. In general, the degree of complementarity between the two stem-forming portions may be, e.g., between 75% and 95%, approximately 85%, etc. While not wishing to be bound by any theory, it is likely that including areas of non-complementarity reduces degradation of the RNA as discussed elsewhere herein. In addition, partial instability may be important to facilitate the linear-loop interaction between the taRNA and a cognate crRNA.

When present within a system (e.g., inside a cell) in which translation of an ORF is repressed by a cognate cis-repressive sequence, e.g., a cognate crRNA, the taRNA causes derepression, allowing translation to occur. As shown in FIG. 3C, while not wishing to be bound by any theory, it is believed that the taRNA interacts with an RNA comprising a cognate cis-repressive sequence (preferably a cognate crRNA) to form a linear-loop complex. The linear-loop complex then undergoes further conformational change so that a duplex structure forms between a portion of the taRNA and a complementary or, preferably, substantially complementary portion of the cis-repressive sequence or crRNA. The conformational change disrupts the stem-loop in which the cis-repressive sequence participated, thereby making the region upstream of the ORF (e.g., the region comprising an RBS or, in eukaryotes, a region comprising a Kozak consensus sequence) accessible to the ribosome. In the case of a prokaryotic system, the ribosome can now gain entry to the RBS and translation can proceed. A stem-loop structure remains in the original taRNA. In preferred embodiments of the invention in eukaryotic systems, this stem is small enough that it does not prevent a scanning ribosome from initiating translation of the downstream ORF. For example, in certain embodiments of the invention the stem that exists in the taRNA after interaction is 50 nucleotides or less, 40 nucleotides or less, 30 nucleotides or less, 20 nucleotides or less, or 10 nucleotides or less.

Figure 3H:
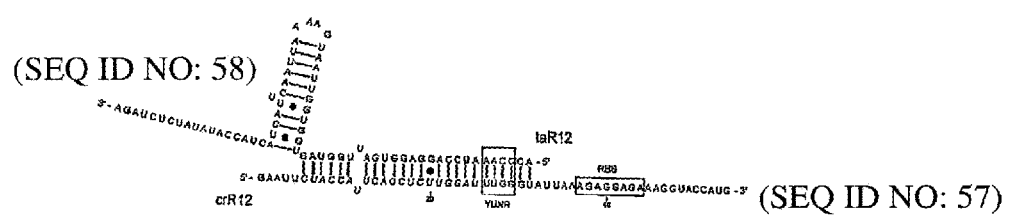
FIG. 3H (trans-activation results) shows a schematic representation of sequence specific taR12-crR12 stable duplex. The 5' linear sequence of taRNA targets its complementary YUNR motif sequence (boxed, light grey) on crRNA. In the presence of taR12, the cis sequence (italicized) is destabilized and forms a stable taR12-crR12 duplex (shown). The resulting duplex exposes the RBS (boxed, black) and allows translation to occur. (start codon (AUG) in bold, allowed G-U mispairings marked by black dots)
Figures 4A, 4B, 4C, 4D, 4E:
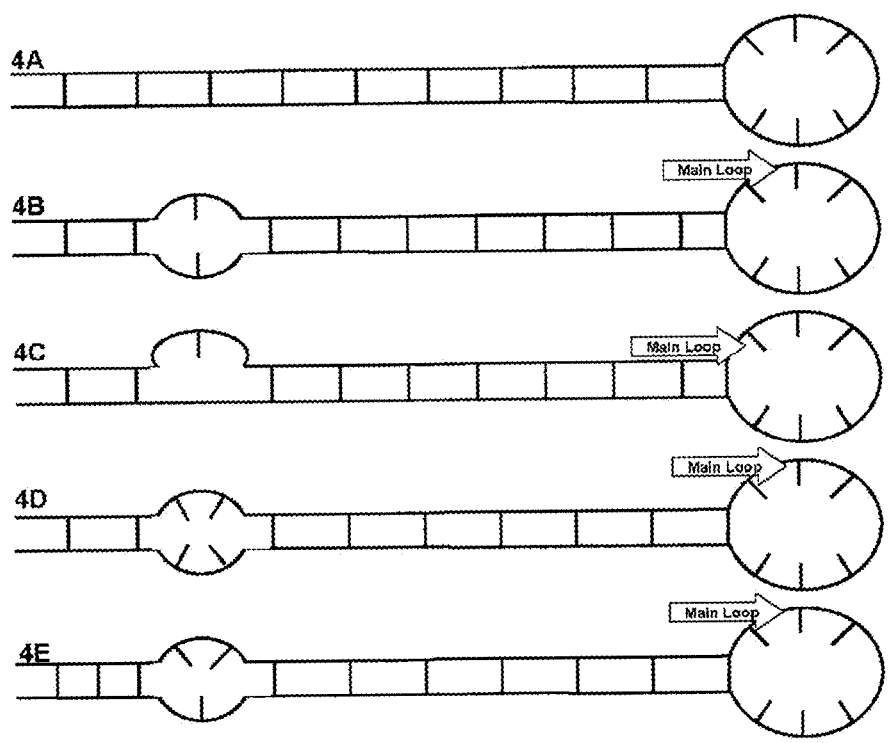
FIG. 4 shows a variety of stem-loop (hairpin) structures. Lines extending from one horizontal strand to another indicate base pairs. Lines that do not extend from one strand to the other indicate unpaired nucleotides.

FIG. 3H shows the structure formed by cognate RNA molecules crR12 and taR12 in further detail, indicating base pairing interactions. As shown therein, a duplex forms between a portion of the taRNA and a portion of the crRNA that includes some, or preferably all, of the cis-repressive sequence. Formation of this structure exposes the sequence 5' of the start codon (including the RBS), thus derepressing (activating) translation. In certain embodiments of the invention the duplex formed between portions of the taRNA and crRNA is between 4 and 100 nucleotides in length, or between 6 and 80, inclusive. In certain embodiments of the invention the duplex formed between portions of the taRNA and crRNA is between 10 and 50 nucleotides in length, inclusive. In certain embodiments of the invention the duplex formed between portions of the taRNA and crRNA is between 20 and 30 nucleotides in length, inclusive. In cases where the duplex is more than approximately 20 nucleotides in length, preferably it includes one or more areas of non-complementarity, e.g., in order to reduce degradation by RNAse molecules present within a cell. For example, the duplex in FIG. 3H is 26 nucleotides in length and includes two dispersed mismatches. It will be appreciated that the taRNA can operate in conjunction with a cis-repressive sequence that represses translation as described above, wherein the cis-repressive sequence is not necessarily within a crRNA element.

It will be appreciated that in accordance with the invention any particular taRNA will operate to derepress translation only when translation is repressed by a suitable cognate crRNA, as opposed to when translation is repressed by a noncognate crRNA. The inventors showed that translation that was repressed by crR10 was activated in the presence of taR10 (the cognate taRNA for crR10) by approximately 5-fold relative to the level of translation in the absense of taR10. Even more strikingly, translation that was repressed by crR12 was activated in the presence of taR12 (the cognate taRNA for crR12) by 10-fold relative to the level of translation in the absense of taR12. When background autofluorescence was subtracted as described above for crRNA calculations, translation that was repressed by crR10 was activated in the presence of taR10 by 8-fold relative to the level in the absence of taR10, and translation that was repressed by crR12 was activated in the presence of taR12 by 19-fold relative to the level of translation in the absence of taR12. Noncognate taRNAs had no effect on translation. Thus in preferred embodiments of the invention translation repressed by a cis-repressive sequence or crRNA is activated by at least 5-fold by the cognate taRNA. In certain embodiments of the invention translation repressed by a cis-repressive sequence or crRNA is activated by at least 10-fold by the cognate taRNA. In certain embodiments of the invention translation repressed by a cis-repressive sequence or crRNA is activated by at least 19-fold by the cognate taRNA.

In order to demonstrate the specificity of the crRNA:taRNA interaction, the inventors measured the equilibrium association constants ($K_A$) between various crRNA:taRNA pairs. As shown in Table 2, the measured $K_A$ values for non-cognate pairs were approximately an order of magnitude or more lower than the values for cognate pairs. Thus in certain preferred embodiments of the invention the equilibrium association constant between cognate crRNA:taRNA pairs is at least $0.5 \times 10^7$ kcal/mol. In other embodiments of the invention the equilibrium association constant is between $0.5 \times 10^7$ and $3.0 \times 10^7$ kcal/mol, inclusive. In other embodiments of the invention the equilibrium association constant is between $0.5 \times 10^7$ and $2.0 \times 10^7$ kcal/mol, inclusive. In other embodiments of the invention the equilibrium association constant is between $0.8 \times 10^7$ and $1.5 \times 10^7$ kcal/mol. In other embodiments of the invention the equilibrium association constant is approximately $1.0 \times 10^7$, $1.1 \times 10^7$, or $1.2 \times 10^7$ kcal/mol.

TABLE 2

Specificity of taRNA-crRNA Interactions. $K_A$: Equilibrium association constant (Mol$^{-1}$) measured by in vitro experiments. ΔFL1 represents the fold change in fluorescence (arbitrary fluorescence units) in the presence of taRNA (+arabinose/−arabinose).

| | crR7 | | crR10 | | crR12 | |
|---|---|---|---|---|---|---|
| | $K_A$ | Δ FL1 | $K_A$ | Δ FL1 | $K_A$ | Δ FL1 |
| taR7 | $3.2 \times 10^7$ | 1× | $0.008 \times 10^7$ | 1× | $0.097 \times 10^7$ | 1× |
| taR10 | $0.10 \times 10^7$ | 1× | $1.1 \times 10^7$ | 5× | $0.13 \times 10^7$ | 1× |
| taR12 | $0.066 \times 10^7$ | 1× | $0.013 \times 10^7$ | 1× | $1.12 \times 10^7$ | 10× |

In certain preferred embodiments of the invention the crRNA and taRNA sequences each have only a single predicted secondary structure rather than multiple predicted secondary structures. A number of computer programs are available to predict secondary structure (e.g., Mfold™, RNAfold™, etc.) One of ordinary skill in the art will be able to select and apply a suitable program for RNA structure prediction when designing crRNA and taRNA molecules in accordance with the principles described herein.

VI. DNA Templates, Constructs, Plasmids, Cells, and Kits

Although the invention was described above primarily in reference to RNA, the nucleic acid molecules of the invention can be RNA or DNA. In general, RNA and DNA molecules can be produced using in vitro systems, within cells, or by chemical synthesis using methods well known in the art. It will be appreciated that insertion of cis-repressive sequences, crRNA elements, etc., upstream of an open reading frame will typically be accomplished by modifying a DNA template for transcription of the ORF. The invention therefore provides DNA templates for transcription of a crRNA or taRNA. The invention also provides DNA constructs and plasmids comprising such DNA templates. In certain embodiments of the invention the template for transcription of a crRNA is operably associated with a promoter. In particular, the invention provides a DNA construct comprising (i) a template for transcription of a crRNA; and (ii) a promoter located upstream of the template. In certain embodiments of the invention a construct or plasmid of the invention includes a restriction site downstream of the 3' end of the portion of the construct that serves as a template for the crRNA, to allow insertion of an ORF of choice. The construct may include part or all of a polylinker or multiple cloning site downstream of the portion that serves as a template for the crRNA. The construct may also include an ORF downstream of the crRNA portion. The invention provides a DNA construct comprising (i) a template for transcription of a taRNA; and (ii) a promoter located upstream of the template. The invention further provides a DNA construct comprising: (i) a template for transcription of a crRNA; (ii) a promoter located upstream of the template for transcription of the crRNA; (iii) a template for transcription of a taRNA; and (iv) a promoter located upstream of the template for transcription of the taRNA. The promoters may be the same or different.

The DNA constructs may be incorporated into plasmids, e.g., plasmids capable of replicating in bacteria. In certain embodiments of the invention the plasmid is a high copy number plasmid (e.g., a pUC-based or pBR322-based plasmid) while in other embodiments of the invention the plasmid is a low copy number plasmid (36). The plasmid may include any of a variety of origins of replication, which may provide different copy numbers. For example, any of the following may be used (copy numbers are listed in parenthesis): ColE1 (50-70 (high)), p15A (20-30 (medium)), pSC101 (10-12 (low)), pSC101* (<4 (lowest)). It may be desirable to use plasmids with different copy numbers for transcription of mRNA to be post-transcriptionally regulated and/or for transcription of taRNA elements to achieve an additional level of control over gene expression. In addition, in certain embodiments of the invention a tunable copy number plasmid is employed (72). FIGS. 5A and 5B show plasmids that provide templates for transcription of a crRNA and a taRNA molecule respectively. FIG. 5C shows a plasmid that provides templates for transcription of both a crRNA and a taRNA molecule.

The invention further provides viruses and cells comprising the nucleic acid molecules, DNA constructs, and plasmids described above. In various embodiments of the invention the cell is a prokaryotic cell. In various embodiments of the invention the cell is a eukaryotic cell (e.g., a fungal cell, mammalian cell, insect cell, plant cell, etc.). The nucleic acid molecules or DNA constructs may be integrated into a viral genome using recombinant DNA technology, and infectious virus particles comprising the nucleic acid molecules and/or templates for their transcription can be produced. The nucleic acid molecules, DNA constructs, plasmids, or viruses may be introduced into cells using any of a variety of methods well known in the art, e.g., electroporation, calcium-phosphate mediated transfection, viral infection, etc. (See, e.g., 47). As discussed further below, the DNA constructs can be integrated into the genome of a cell. In general, the cells of the invention may be present in culture or in an organism. If present within a human being, the cells are not part of the human being, thereby avoiding any interpretation of the claims of the invention that may be construed as claiming a human being or portion thereof.

The invention further provides transgenic plants and non-human transgenic animals comprising the nucleic acid molecules, DNA constructs, and/or plasmids of the invention. Methods for generating such transgenic organisms are well known in the art.

The invention further provides a variety of kits for implementation of the riboregulator system. For example, the invention provides a kit comprising two plasmids, wherein the first plasmid comprises (i) a template for transcription of a cis-repressive RNA element; and (ii) a promoter located upstream of the template for transcription of the cis-repressive RNA element, and wherein the second plasmid comprises (i) a template for transcription of a cognate trans-activating RNA element; and (ii) a promoter located upstream of the template for transcription of the trans-activating RNA element. The promoters may be the same or, preferably, different. One or more of the promoters may be inducible. The plasmids may have the same or different copy numbers. The invention further provides a kit comprising a single plasmid that comprises a template for transcription of a cis-repressive RNA element and a promoter located upstream of the template for transcription of the cis-repressive RNA element and further comprises a template for transcription of a cognate trans-activating RNA element and a promoter located upstream of the template for transcription of the cognate trans-activating RNA element In certain embodiments of the invention the plasmids comprise one or more restriction sites downstream of the template for transcription of the cis-repressive RNA element for insertion of an open reading frame of choice. The kits may further include one or more of the following components: (i) one or more inducers; (ii) host cells (e.g, prokaryotic or eukaryotic host cells); (iii) one or more buffers; (iv) an enzyme, e.g., a restriction enzyme; (v) DNA isolation and/or purification reagents; (vi) a control plasmid lacking a crRNA or taRNA sequence; (vii) a control plasmid containing a crRNA or taRNA sequence or both; (viii) sequencing primers; (ix) instructions for use. The control plasmids may comprise a reporter sequence.

The invention further provides oligonucleotides comprising a crRNA sequence and oligonucleotides comprising a taRNA sequence. In addition, the invention provides sets of two or more oligonucleotides. A first set of oligonucleotides includes two or more oligonucleotides whose sequences together comprise a crRNA sequence. The invention also provides a second set of oligonucleotides whose sequences together comprise a taRNA sequence. For ease of cloning, it may be preferable to employ two oligonucleotides each of which includes a single stem-forming portion, in different cloning steps, rather than a single oligonucleotide comprising two stem-forming portions, in order to avoid formation of a stem within the oligonucleotide, which may hinder cloning (see Example 1). The oligonucleotides may be provided in kits with any of the additional components mentioned above. The oligonucleotides may include restriction sites at one or both ends.

VII. Components for Riboregulator Systems

The sections above described an implementation using two different promoter pairs to drive transcription of the crRNA and taRNA and employed a single consensus ribosome binding site. This section describes a number of variations suitable for use in various embodiments of the invention. However, the invention is not limited to these particular embodiments.

A. Ribosome Binding Site

The riboregulators described above employed a consensus prokaryotic RBS. However, in various embodiments of the invention any of a variety of alternative sequences may be used as the RBS. The sequences of a large number of bacterial ribosome binding sites have been determined, and the important features of these sequences are known (see 53, 54, 55 and references therein, which are incorporated by reference herein). Preferred RBS sequences for high level translation contain a G-rich region at positions −6 to −11 with respect to the AUG and typically contain an A at position −3. Exemplary RBS sequences for use in the present invention include, but are not limited to, AGAGGAGA (or subsequences of this sequence, e.g., subsequences at least 6 nucleotides in length, such as AGGAGG. Shorter sequences are also acceptable, e.g., AGGA, AGGGAG, GAGGAG, etc. Numerous synthetic ribosome binding sites have been created, and their translation initiation activity has been tested (53). In various embodiments of the invention any naturally occurring RBS may be used in the crRNA and taRNA constructs. Any of the RBS sequences provided in (53), or, shorter versions thereof (e.g., the first 6 nucleotides, the first 8 nucleotides, or the first 10 nucleotides) may also be used. The activity of any candidate sequence to function as an RBS may be tested using any suitable method. For example, expression may be measured as described in Example 1, or as described in reference 53, e.g., by measuring the activity of a reporter protein encoded by an mRNA that contains the candidate RBS appropriately positioned upstream of the AUG. Preferably an RBS sequence for use in the invention supports translation at a level of at least 10% of the level at which the consensus RBS supports translation (e.g., as measured by the activity of a reporter protein). For example, if the candidate RBS is inserted into the control plasmid described in Example 1 in place of the consensus RBS, the measured fluorescence will be at least 10% of that measured using the consensus RBS. In certain embodiments of the invention an RBS that supports translation at a level of at least 1%, 5%, 10%, 20%, 30%, 40%, 50%, 60%, 70%, 80%, 90%, or more relative to the level at which the consensus RBS supports translation is used. In certain embodiments of the invention an RBS that supports translation at higher levels than the consensus RBS is used. If an alternative RBS is selected, the cis-repressive sequence and taRNA sequence are modified to be complementary to the alternative RBS.

B. Promoters

A large number of different promoters that operate in prokaryotic cells are known and can be used to drive transcription of mRNAs comprising crRNA elements and/or transcription of taRNA elements in various embodiments of the invention. As described herein, inducible promoters such as the PL(tetO), pBAD, and PL(lacO) promoters are used. Other synthetic promoters that may be used include PAllacO-1 and Plac/ara-1. Phage promoters such as SP6, T3, or T7 can also be used. Other suitable promoters include, without limitation, any of the responsive or constitutive promoters listed in Table 3. In general, the level of transcription driven by a "responsive promoter" varies depending on, or in response to, environmental conditions or stimuli, or changes in such conditions or stimuli.

TABLE 3

Responsive and Constitutive Prokaryotic Promoters

| | Compound/Condition Sensed |
|---|---|
| Responsive Promoters | |
| $P_{ANR}$ | Anaerobicity |
| $P_{cspA}$ | Cold Shock |
| $P_{E\sigma32}$ | Heat Shock |
| $P_{ibp}$ | Cytoplasmic Stress |
| $P_{oxyR}$ | Oxidative Stress |
| $P_{lexA}$ | SOS (DNA damage) |
| $P_{recA}$ | SOS (DNA damage) |
| $P_{phoB}$ | Phosphate Starvation |
| $P_{ada}$ | DNA Alkylation |
| $P_{dmpR}$ | Aromatic Compounds |
| $P_u$ | Toluene-based Compounds |
| $P_{bphA1}$ | Polychlorinated biphenyls (PCBs) |
| $P_{merTPAD}$ | Mercury |
| $P_{pcoE}$ | Copper |
| $P_{pbrA}$ | Lead |
| $P_{cad}$ | Cadmium |
| $P_{his}$ | Histidine |
| $P_{scrY}$ | Sucrose |
| $P_{alkB}$ | Middle-chain Alkanes |
| $P_{luxI}$ | N-Acyl homoserine lactones |
| $P_{flgMN}$, $P_{flgAMN}$ | Flagellation |
| $P_{flhD}$ | Flagellation, Motility and Chemotaxis |
| $P_{uhpABCT}$ | Sugar Phosphate Uptake |
| Constitutive Promoters | |
| $P_{spc}$ | Ribosomal Protein Operon |
| PL | From Phage Lambda |
| $P_1$ | RrnB Ribosomal RNA operon |
| $P_2$ | RrnB Ribosomal RNA operon |
| $P_{lpp}$ | Promoter for major outer membrane lipid protein gene |

Any of a wide variety of promoters can be used in eukaryotic cells (e.g., fungal, insect, plant, or mammalian cells) to drive transcription of the mRNA containing the cis-repressive RNA element and the trans-activating RNA element. Suitable promoters include, without limitation, constitutive promoters (e.g., actin, tubulin), inducible promoters, GAL promoters, viral LTR (long terminal repeat) promoters, CMV promoter (cytomegalovirus), RSV promoter (Rous sarcoma virus), SV40 promoter, cauliflower mosaic virus promoter (CaMV), Vlambdal promoter, EF1 alpha promoters, cell cycle regulated promoters (e.g, cyclin A, B, C, D, E, etc). Suitable inducible promoters include steroid responsive promoters, metal-inducible promoters (e.g., metallothionine promoter), the tet system (67, 71) etc. Non-limiting examples of tissue-specific promoters appropriate for use in mammalian cells include lymphoid-specific promoters (see, for example, Calame et al., *Adv. Immunol.* 43:235, 1988) such as promoters of T cell receptors (see, e.g., Winoto et al., *EMBO J.* 8:729, 1989) and immunoglobulins (see, for example, Banerji et al., *Cell* 33:729, 1983; Queen et al., *Cell* 33:741, 1983), and neuron-specific promoters (e.g., the neurofilament promoter; Byrne et al., *Proc. Natl. Acad. Sci. USA* 86:5473, 1989). Developmentally-regulated promoters may also be used, including, for example, the murine hox promoters (Kessel et al., *Science* 249:374, 1990) and the α-fetoprotein promoter (Campes et al., *Genes Dev.* 3:537, 1989). One of ordinary skill in the art will be able to select appropriate promoters depending, e.g., upon the particular cell type in which the cis and trans elements of the invention are to be employed.

VIII. In Vitro Selection of Additional crRNA:taRNA Cognate Pairs

It will be appreciated that using the guidelines described herein one of ordinary skill in the art will be able to readily design and generate additional cis-repressive sequences, crRNA elements, and cognate taRNA elements, including elements that exhibit a a variety of different levels of repression and derepression. The invention provides a variety of different methods for so doing. For example, one of ordinary skill in the art will appreciate that by changing one nucleotide in a first stem-forming portion and making a compensatory change in the second stem-forming portion (so that the resulting nucleotides still form either a complementary or non-complementary pair as in the additional structure), the structure and thermodynamic properties of the resulting structure remain largely the same. Thus by beginning with known crRNA:taRNA cognate pairs, one can generate a family of related cognate pairs by systematically altering pairs of nucleotides. In addition, making small changes, e.g., engineering an additional 1 nucleotide bulge, increasing the length of the stem-forming portion by one or two nucleotides, etc., will result in crRNA:taRNA pairs with similar properties to the parent pair. In making such changes it will generally be desirable to retain features such as the presence of dispersed areas of non-complementarity, the approximate overall percent complementarity, the approximate equilibrium association constant of the pairs, etc. Thus the invention specifically encompasses variants of crR10, crR12, taR10, and taR12 that differ from these molecules by 10 or fewer nucleotides, i.e., molecules that can be derived from crR10, crR12, taR10, or taR12 by making 12 or fewer (e.g., 1, 2, 3, 4, 5, 6, 7, 8, 9, 10, 11, or 12) additions, substitutions, or deletions of a nucleotide. The ability of any crRNA:taRNA pair to repress or activate translation, respectively, may be readily tested, e.g., as described in Example 1.

A further aspect of the invention is a method for generating large numbers of additional riboregulator pairs using an in vitro selection process. This method (which may be referred to as "directed evolution") can result in generation of a very large number of specific riboregulator pairs. According to one embodiment of the inventive method one begins with the sequences of a riboregulator pair that has been shown to function to repress and derepress translation (e.g., the crR10:taR10 or crR12:taR12 pair). An initial pool of randomized molecules is generated based on these sequences (e.g. as described in 22, 23, 68, 69) in which the nucleotides that participate in the crRNA:taRNA interaction are targeted for randomization (e.g, the 26 nucleotides that form a stem when crR10 and taR10 or crR12 and taR12 interact). Randomization is typically performed using a PCR step, e.g., employing error-prone PCR (78, 79). Thus the starting templates for the in vitro selection process are typically DNA constructs that comprise templates for the initial crRNA:taRNA pair. In general, any of a variety of other methods may be used to achieve randomization including, but not limited to, DNA shuffling (80, 81), cassette mutagenesis (82), degenerate oligonucleotide directed mutagenesis (83, 84), sticky feet mutagenesis (85), and random mutagenesis by whole plasmid amplification (86). If desired, multiple rounds of randomization can be performed.

Following randomization, the crRNA and taRNA randomized sequences are amplified (e.g., using PCR) to incorporate a promoter for in vitro transcription (e.g., a T7 or SP6 promoter) at the 5' end. An in vitro transcription reaction is then performed using the products, in order to synthesize separate pools of crRNA and taRNA transcripts for use in subsequent selection steps.

Portions of the crRNA transcript pool are dispersed into individual vessels, e.g., multiwell plates. Portions of the taRNA transcript pool are also added to the vessels so that each vessel contains a plurality of different crRNA transcripts and a plurality of different taRNA transcripts. The taRNAs may be added at elevated concentrations relative to that which would typically be achieved within cells, e.g., concentrations optimized for cognate pair binding vs binding of noncognate pairs (see Example 3). Pairing between cognate crRNA and taRNA elements is allowed to occur. A labeled reverse transcription primer probe (e.g. a Cy5 labeled probe as described in Example 3) is added, and RT-PCR is performed. The RT-PCR products are then run on a gel. RT-PCR generates two main populations of detectable RNA species: (i) the crRNA molecule alone and (ii) the crRNA:taRNA complex. Pairs that show both RNA species are selected.

Standard sequencing reactions are performed for each selected pair. The selected crRNA and taRNA sequences are then analyzed using any available algorithm for prediction of secondary structure (e.g., MFOLD, RNAFOLD). If desired, structures may be examined to determine whether they meet certain of the guidelines for effective crRNA:taRNA elements described above. Selected crRNA and taRNA elements are cloned into appropriate vectors (e.g., those presented in FIG. 5) in place of the crRNA and taRNA elements. Gene expression experiments are then performed to determine whether the crRNA elements effectively repress translation of a downstream ORF and whether repression is relieved by the cognate taRNA. It will be appreciated that a number of variations on the above can be made. For example, alternative methods for assessing the interaction between candidate crRNA:taRNA pairs can be used (see Example 3, which mentions alternate methods for measuring association constants). In addition, it will be appreciated that it is not necessary to randomize both the crRNA and taRNA sequences. For example, it may be desirable to use a single crRNA sequence and to randomize only the taRNA sequence, in order to generate a set of taRNA molecules that display a range of abilities to activate translation that is repressed by the crRNA molecule. Conversely, it may be desirable to use a single taRNA sequence and to randomize only the crRNA sequence in order to generate a set of crRNA molecules that can be derepressed to different extents by the same taRNA molecule.

IX. Increasing Riboregulator Flexibility

A. Use of Responsive Promoters

A variety of approaches may be employed to enhance the flexibility of the riboregulator systems of the present invention. For example, by placing transcription of the taRNA element under control of a responsive promoter, such as an endogenous cellular promoter that is responsive to an environmental or developmental stimulus (e.g., the presence of a small molecule, metabolite, nutrient, hormone, cell density signal, etc.), activation of translation by the taRNA in turn becomes responsive to that stimulus. By incorporating a single crRNA element into an mRNA upstream of the open reading frame and by driving transcription of the cognate taRNA element from a plurality of different promoters, each responsive to a different environmental or developmental stimulus, translation of the mRNA is in turn made responsive to each of these stimuli. This type of control is referred to as "many to one" control since many stimuli affect translation of one mRNA. Conversely, a single crRNA element may be positioned upstream of the ORF in a plurality of different mRNAs. Transcription of the cognate taRNA causes activation of translation of the plurality of mRNAs. This type of control is referred to as "one to many" control.

By combining these two approaches, "many to many" control can be achieved using only a single cognate crRNA: taRNA pair. For example, a single crRNA element may be positioned upstream of the ORF in a plurality of different mRNAs, and transcription of the cognate taRNA may be placed under control of a plurality of different promoters, each responsive to an environmental or developmental stimulus. Occurrence of any of the stimuli activates transcription of the taRNA, which then activates translation of all of the ORFs that contain the crRNA element upstream of the ORF. Thus any of a variety of inputs can result in a single, coordinated output involving translation of multiple different ORFs. Yet further flexibility can be achieved by using a plurality of different cognate crRNA:taRNA pairs. Thus it is possible to extensively modify existing genetic networks, to integrate new components into such networks, or to create entirely artificial genetic networks of considerable complexity using the riboregulator systems described herein.

Figure 5:
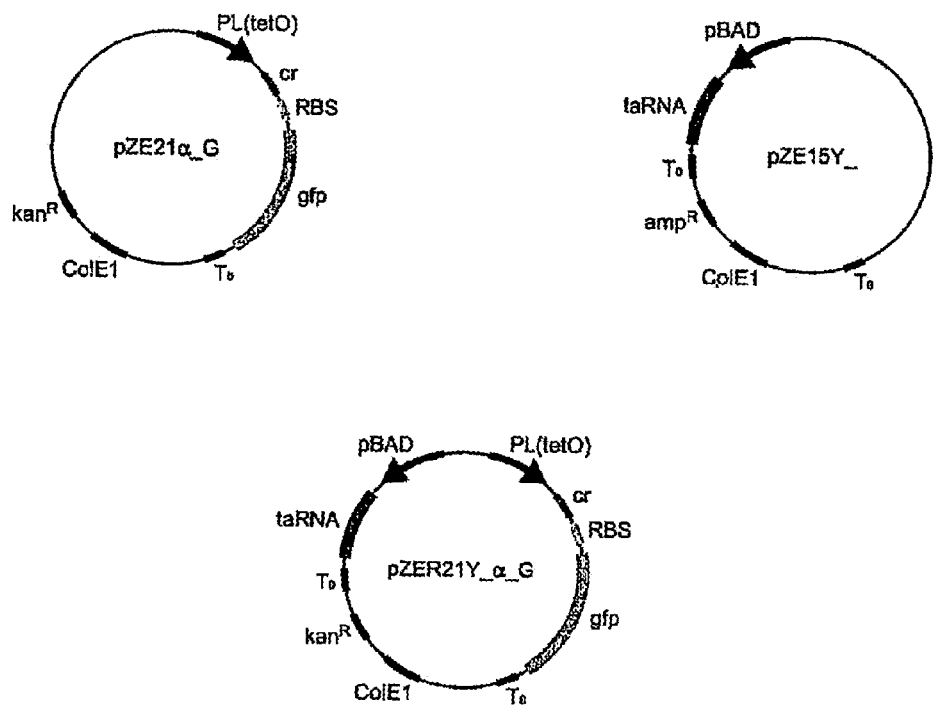
FIG. 5 shows the main set of plasmids used in the artificial riboregulator system. Cis-repressive RNA plasmids, pZE21alpha_G (i.e., pZE21alphaLG, see Table 4), contain PL(tetO) producing the cr sequence, loop, RBS and gfpmut3b gene. Trans-activating RNA plasmids, pZE15Y_ (i.e., pZE15YL), contain the pBAD promoter expressing taRNA. In plasmids containing Riboregulator System I, pZE21alpha_G and pZE15Y_ were combined to form pZER21Y_alpha_G. All plasmids contained the ColE1 origin of replication and gene coding for either ampicillin or kanamycin resistance. In Riboregulator System II, the PL(tetO) and pBAD promoters were replaced with the PL(lacO) and PL(tetO) promoters, respectively. See Table 4 for complete list of plasmids.

B. Translational Control Using Single Plasmid, Multiple Plasmid, or Chromosomally Integrated CrRNA and TaRNA Elements As mentioned above, the invention provides plasmids comprising templates for transcription of crRNA and taRNA elements. In general, crRNA and taRNA elements may be introduced into a cell on separate plasmids, or a single plasmid containing one or more crRNA and/or taRNA elements can be introduced into a cell. Thus a plasmid may contain one or more crRNA elements, one or more taRNA elements (which may be cognate to the same crRNA element or to different crRNA elements), or both crRNA and taRNA elements. Generally each crRNA and/or taRNA element is operably linked to a promoter. The same promoter may drive transcription of multiple elements, or different promoters may be used for different elements. In general, it will be desirable to employ different promoters for the crRNA and taRNA elements of a cognate pair. The crRNA elements may be positioned upstream of a site for convenient insertion of an open reading frame, e.g., a restriction site or polylinker. The plasmid may further comprise one or more open reading frames positioned downstream from a crRNA element, preferably in frame with the start codon. FIG. 5 presents representative examples of plasmids provided by the invention. It is to be understood that the gfp sequence may be replaced by any open reading frame of choice or such open reading frame can be added to create a larger open reading frame encoding a fusion protein. The plasmids may also include sequences encoding tags, e.g, His tag, FLAG tag, HA tag, Myc tag, etc., to enable purification of a protein encoded by a reading frame in frame with the tag sequences.

In addition to providing the crRNA and taRNA elements on plasmids, a DNA construct that provides a template for transcription of one or more crRNA and/or taRNA elements (and, optionally, an open reading frame downstream of a crRNA element) may be integrated into the genome of a cell. In general, such constructs may be integrated at random locations. Alternatively, the constructs may be integrated at specific locations, e.g., at regions of homology to the construct. For example, if the construct comprises a promoter and/or ORF that is homologous to endogenous cellular DNA, the construct may be inserted so as to replace the endogenous DNA. Methods for inserting DNA sequences into the genome of prokaryotic cells and for targeting such DNA sequences for insertion at specific locations are well known in the art (73, 74). Methods for inserting DNA sequences into the genome of eukaryotic cells are also well known in the art. Standard transfection or viral infection methods may be used to achieve random integration. Alternately, homologous recombination may be used to integrate DNA sequences into the genome of eukaryotic cells and/or to generate transgenic non-human mammals in which an endogenous DNA sequence is replaced by the DNA construct (75-77).

C. Ligand-Responsive Aptamer Domains

A number of naturally occurring mRNA molecules have been shown to bind to small molecules such as thiamine, coenzyme B12, flavin mononucleotide, etc., causing allosteric rearrangement of the mRNA, which results in modulation of gene expression. Such RNAs exist in both prokaryotic and eukaryotic cells (10, 11, 16, 70). The inventors have recognized that by incorporating specific ligand-binding domains into the crRNA and taRNA elements of the invention, these elements can be made responsive to the presence or absence of the ligand. Therefore, in certain embodiments of the invention the crRNA or taRNA comprises a domain that responds to an endogenous or exogenous signal. Riboregulators that include such a domain are referred to as responsive riboregulators. Signals to which responsive riboregulators respond include, for example, (i) small molecules; (ii) metabolites; (iii) nutrients; (iv) metal ions; (v) cell density signals.

As discussed above, in vitro selection has been used to isolate nucleic acid sequences (aptamers) that bind small molecules with a high degree of affinity and specificity (64, 68, and 69 and references therein). Binding of the small molecule ligand can alter the structure of the aptamer, and this alteration may be used to control translation. For example, insertion of an RNA aptamer that specifically bind to aminoglycosides into the 5' UTR of an RNA allowed its translation to be repressible by ligand addition (64). By incorporating a ligand-specific aptamer into the taRNA elements of the invention, their ability to activate translation can be made responsive to presence of the ligand.

In accordance with these embodiments of the invention an RNA aptamer that binds to a particular molecule of interest is selected using established in vitro selection techniques as described above. The aptamer is incorporated into the taRNA. Binding of the ligand induces a conformational change in the taRNA that allows or enhances the interaction between the crRNA and the taRNA, thereby activating translation. In these embodiments of the invention the taRNA may be present constitutively within a cell but is inactive in the absence of the ligand. Ligand-specific aptamers can also be incorporated into the crRNA elements of the invention and/or used in conjunction with cis-repressive sequences to allow increased control over gene expression.

D. Exogenous Delivery

The description above referred primarily to applications of the riboregulator elements that involved their transcription within cells. However, according to certain embodiments of the invention either the crRNA element with a downstream ORF, the taRNA element, or both, is synthesized in vitro and delivered to a cell. In most cases the crRNA element is transcribed within a cell and the taRNA element is delivered exogenously. For such applications it may be desirable to synthesize a riboregulator element, e.g., a taRNA element using either DNA or a combination of DNA and RNA. It may also be desirable to employ various nucleotide analogs in order, for example, to increase the stability and/or nuclease resistance of the molecule. In addition, such modifications and analogs may be used to alter the base-pairing properties of the molecule as desired.

According to certain embodiments of the invention various nucleotide modifications and/or analogs are used. Numerous nucleotide analogs and nucleotide modifications are known in the art, and their effect on properties such as hybridization and nuclease resistance has been explored. (In general, nucleotide analogs and modified nucleotides will be referred to herein as "nucleotide analogs".) For example, various modifications to the base, sugar and internucleoside linkage have been introduced into oligonucleotides at selected positions, and the resultant effect relative to the unmodified oligonucleotide compared. A number of modifications have been shown to alter one or more aspects of the oligonucleotide such as its ability to hybridize to a complementary nucleic acid, its stability, etc. For example, useful 2'-modifications include halo, alkoxy and allyloxy groups. U.S. Pat. Nos. 6,403,779; 6,399,754; 6,225,460; 6,127,533; 6,031,086; 6,005,087; 5,977,089, and references therein disclose a wide variety of nucleotide analogs and modifications that may be of use in the practice of the present invention. See also Crooke, S. (ed.) "Antisense Drug Technology: Principles, Strategies, and Applications" ($1^{st}$ ed), Marcel Dekker; ISBN: 0824705661; 1st edition (2001) and references therein. As will be appreciated by one of ordinary skill in the art, analogs and modifications may be tested using, e.g., the assays described herein or other appropriate assays, in order to select those that effectively regulate translation. Additional modifications such as addition of polyethylene glycol (PEG), e.g., to increase stability, can be used.

A variety of methods can be used to introduce riboregulator elements into cells, particularly into eukaryotic cells. Numerous agents that facilitate uptake of oligonucleotides and of DNA constructs by cells are known in the art and include various lipids, e.g., cationic lipids such as Oligofectamine™, polymers, e.g., cationic polymers, etc. In general, any of the reagents used for RNA or DNA delivery in culture or in vivo (e.g., materials for use in gene therapy) may be used.

E. Additional Cis Element(s)

Figures 9A, 9B, 9C, 9D:
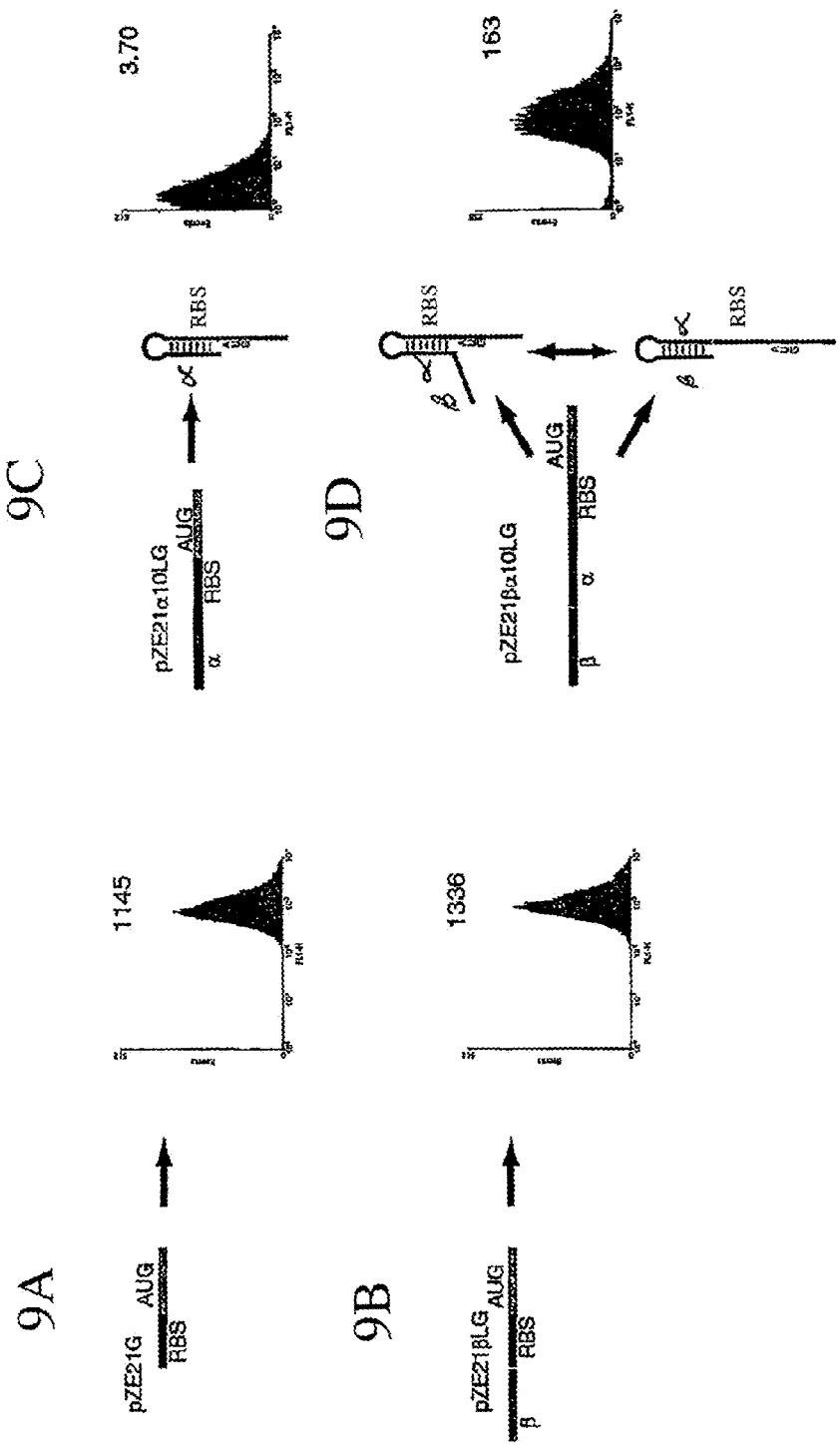
FIGS. 9A-9D shows GFP expression results using an additional cis element. RBS is ribosome binding site, α refers to a first cis-repressive element, β is the additional element. α is complementary to both RBS and β and can bind to either sequence.

By adding one or more additional cis-repressive sequences to the cis-repressive RNA elements described above, it is possible to obtain more finely grained control over expression. In particular, it is possible to obtain an intermediate expression level using two different cis elements both of which interact with the same cognate taRNA, or with different taRNAs. For example, as shown in FIG. 9, an additional sequence (labeled β) can be added upstream of a cis-repressive sequence (labeled α). The additional sequence is complementary or substantially complementary to the cis-repressive sequence. In FIG. 9, the cis-repressive sequence contains a portion that is complementary or substantially complementary to the RBS. This sequence will generally not form a stem with sequences between its 3' end and the beginning of the ORF. Thus in FIGS. 9A and 9B, translation is not repressed, while in FIG. 9C, in the presence of the cis-repressive sequence, translation is repressed. When the additional sequence is added, it can form a stem-loop structure with the cis-repressive sequence, thereby preventing the cis-repressive sequence from sequestering the RBS, as shown in the lower portion of FIG. 9D. Thus two alternate structures are possible. In one structure (upper portion of FIG. 9D), the cis-repressive sequence forms a stem that sequesters the RBS, while in the alternate structure the cis-repressive sequence forms a stem with the additional sequence, allowing the ribosome to access the RBS. While not wishing to be bound by any theory, it is likely that at any point in time individual mRNAs will assume one structure or the other, and a single mRNA may switch back and forth between the two structures. Thus it is evident that in a population of mRNAs or for any individual mRNA, translation will be possible during a fraction of the time. Thus an intermediate level of translation occurs, as shown in FIG. 9D. This general principle can be extended, e.g., by incorporating additional sequences into the repressive RNA elements of the invention, to allow the formation of a range of different stem-loop structures, which may exhibit greater or less stability than a stem-loop formed between the cis-repressive sequence and sequences between the 3' end of the cis-repressive sequence and the 5' end of the ORF (or the 5' portion of the ORF). Alternatively, multiple trans-acting RNAs, each of which can be unique, can be targeted for the corresponding cis elements.

X. Additional Features and Applications of the Riboregulators

As described herein, the inventors have created post-transcriptional control elements that circumvent the need for specific promoters, genes, or regulators, and can be utilized as control modules in genetic circuits to investigate additional layers of gene regulation. Given their scalability and specificity of interaction, the number of elements and their range of functions can be greatly expanded by in vitro selection techniques as described above (22-24), creating a large collection of interactive riboregulators. Such an assembly could generate in vivo cascades of highly specific riboregulator or riboswitch networks, which may respond faster, conserve more energy (43), and be more complex than networks based solely on DNA-protein components. Linking these switches with endogenous riboregulators and switches (10-16) and cell-cell signaling molecules, would further broaden their utility. Such, post-transcriptional control systems will also be a valuable tool in resolving the complexity of large-scale gene networks, since current studies rely on evaluating global patterns of gene expression or constructing synthetic networks, which have been limited to well-characterized transcription factors. For example, the use of riboregulators could selectively perturb networks of unknown structure and reveal functional properties of genetic networks.

The work described herein, which details positive and negative post-transcriptional control, elucidates the action of cis and trans acting regulatory RNAs. While not wishing to be bound by any theory, the inventors find that conformational changes in RNA structures and stable duplex formation not only depend on the initial recognition complex, but also on the ability of trans activators to bind to nucleotides in the partially destabilized stem structure. In the system described herein, the specificity of intermolecular RNA interaction arises from unique sequences in the crRNA stem and not the consensus sequence of the recognition loop. Studies of artificial riboregulators and switches of this sort can be a valuable method of characterizing potential modes of action of sRNAs, which have been implicated as regulators of transcription, translation, and modulators of developmental switches. In addition, this work may further motivate ongoing sequence- and structure-based efforts to identify novel sRNAs, particularly trans activators, in both prokaryotes and eukaryotes. Ultimately, the versatility of artificial riboregulators and switches may also yield additional insights into RNA-based cellular processes and RNA's evolutionary role in biology (1, 2).

The riboregulators of the invention find use in a wide variety of contexts and possess features that distinguish them from other available systems for control of gene expression. In general, the riboregulators are useful for any of the wide variety of applications for which inducible and repressible promoter systems are used. The riboregulators may provide a faster response than could be achieved by placing a gene under control of an inducible promoter. Unlike regulation that involves activating or repressing transcription of a full-length mRNA, the present invention requires transcription (or exogenous administration) of a short RNA segment (the taRNA), which then relieves translational repression of a pre-existing mRNA. In addition, the riboregulator system does not require replacement of the endogenous promoter, thus physiologic levels of transcription and transcriptional responses to environmental and developmental stimuli can be maintained. This is typically impossible with currently available inducible promoter systems. Furthermore, the riboregulators of the invention may be used in conjunction with transcriptional control elements (e.g., regulatable promoters), to achieve a greater dynamic range (i.e., a greater range of expression levels) than could otherwise be achieved. In addition, the riboregulator system can be used to control expression of a single transcription unit within an operon.

By providing the same crRNA element upstream of a plurality of different open reading frames, these reading frames may be coordinately regulated in response to a single stimulus. For example, a single crRNA element may be positioned upstream of a set of open reading frames. By providing the cognate taRNA (e.g., by inducing its transcription or exogenously), translation of the set of open reading frames will be coordinately activated. For example, a particular crRNA sequence may be positioned upstream of a plurality of open reading frames coding for proteins that are involved in a single biological process (e.g., a developmental process, a response to an environmental stress, etc.). Expression of the entire set of proteins may be activated by a single taRNA. Thus the taRNA may act as a master control switch. The taRNA may be delivered exogenously, or its transcription may be induced. Alternately, a template for transcription of the taRNA may be inserted downstream of a plurality of different promoters, e.g., promoters that respond to environmental or developmental stimuli, so that these stimuli will cause transcription of the taRNA and activation of translation. In yet another variation, a responsive taRNA may be used. In this case, presence of the appropriate activating ligand or environmental condition activates the taRNA, which then binds to the cognate crRNA present upstream of the open reading frames, thereby derepressing translation.

The riboregulators may function as switches, e.g., on-off switches or may provide a graded response. They may operate within genetic networks (either synthetic or natural genetic networks) and/or provide a link between synthetic and natural genetic networks. They may be used to introduce perturbations into networks of unknown structure in order to reveal natural network connectivity. This allows the identification of key components of such networks, which may provide suitable therapeutic targets for treatment of diseases and conditions in which such networks malfunction. With the increasingly rapid acquisition of genetic information and powerful new experimental techniques the ability to construct, analyze, and interpret qualitative and quantitative models is becoming more and more important (45). The ability to analyze and perturb natural genetic networks and to create such networks using tools such as the riboregulators of the present invention is important for the engineering of artificial gene regulatory networks (see 63 for a review of the engineering of gene regulatory networks).

A particular use of the riboregulator systems is to determine the effect on global gene expression levels or on the expression levels of a particular gene or plurality of genes in response to changes in the expression of a gene of interest. For example, expression of a gene of interest (i.e., translation of an mRNA transcribed from the gene), can be repressed using an appropriate crRNA element, and expression levels of other genes can be measured. Translation can then be activated by a cognate taRNA, and expression levels of the gene(s) can be measured again. By comparing expression levels before and after activation of translation, the effect of the gene of interest on expression levels of other genes can be determined. In general, the expression level of such genes can be measured at either the mRNA or protein level by a variety of methods including, but not limited to, microarray analysis, Northern blot, RT-PCR, Western blot, immunoassay, etc., or by competitive PCR coupled with matrix-assisted laser desorption/ionization-time-of-flight (MALDI/TOF) mass spectometry as described herein.

There is an increasing interest in creating circuits and performing computations using biological components (66). The riboregulators of the present invention can operate in such circuits as digital switches, analogous to the role played by transistors in electronic circuits. The state of translational repression established by the crRNA elements corresponds to the LOW state while the activated state established by the taRNA element corresponds to the HIGH state. By using a responsive taRNA element, repeated ON/OFF switching can be achieved. The ON or OFF state may also be used for information storage.

The riboregulators of the invention are useful for control of bioprocesses. A large number of useful substances are most efficiently produced by microorganisms such as bacteria or fungi. This includes some pharmaceutical products, food additives and supplements, bulk chemicals such as ethanol, and enzymes. In addition, an increasing number of useful products including a variety of pharmaceutical agents (e.g., antibodies, enzymes) are produced by harvesting them from mammalian cells or culture medium. Efficient bioprocess operation frequently involves attempts to control the metabolism of the cells involved in the process. For example, it may be desirable to maintain the cells in a particular physiological state and then rapidly switch them to a different state, e.g., to prevent the accumulation of undesired products or to achieve maximum rate of production of the desired product. The riboregulators may be used to alter endogenous metabolic processes to improve yield or rate of production. For example, a particular crRNA sequence may be positioned upstream of a plurality of open reading frames coding for enzymes that are involved in a single biosynthetic pathway. Expression of the entire set of enzymes may be activated by a single taRNA. The taRNA may be delivered exogenously, or its transcription may be induced. Alternately, a responsive taRNA may be used. In this case, presence of the appropriate activating ligand or environmental condition activates the taRNA, which then binds to the cognate crRNA present upstream of the open reading frames, thereby derepressing translation.

The riboregulators may be employed in conjunction with gene knockouts. For example, a gene can be knocked out in prokaryotic cells or in eukaryotic cells in tissue culture or in eukaryotic organisms (e.g., fungi, mice, using standard methods, and more recently pigs, sheep, bovines, etc. using methods known in the art). The gene can then be reintroduced with its endogenous promoter and a crRNA element upstream of the coding sequence. This will re-establish a responsive endogenous promoter-gene pair that is repressed. Physiologic transcription levels can be maintained and post-transcriptional expression can be modulated using a cognate taRNA, which can be provided exogenously or by inducing its transcription. Alternately, a responsive taRNA can be used, in which case translation can be activated by providing the appropriate ligand or environmental condition.

The riboregulators also find use for the control of plasmid copy number. In addition, the riboregulators can be used in conjunction with in vitro translation systems.

EXAMPLES

Example 1

Synthesis and Activity of Cis-Repressive RNA Elements

This example describes the design of a variety of cis-repressive RNA elements (crRNAs) and creation of DNA constructs that provide templates for their synthesis. The example further presents measurements demonstrating the ability of these RNA elements to repress translation of downstream coding sequences. Example 2 describes corresponding trans-activating nucleic acid elements (taRNAs) and their ability to activate gene expression by relieving the translational repression caused by the crRNAs.

Materials and Methods

Plasmid construction, cell strains, reagents: Basic molecular biology techniques were implemented as described in cloning manuals (47). Two riboswitch systems were constructed, in which each system utilized two separate promoters to drive the expression of the cis-repressive RNAs (crRNA) and trans-activating RNAs. In the first riboswitch, the PL(tetO) promoter drives expression of crRNA, and the pBAD promoter drives expression of taRNA. In the second system, PL(lacO) drives the expression of crRNA and PL(tetO) drives expression of taRNA. For each system, three main sets of plasmids were constructed (FIG. 5): (i) crRNA plasmids, (ii) taRNA plasmids, and (iii) riboregulator plasmids. All plasmids (Table 4) contained the pBR322 ColE1 origin of replication and genes coding for either ampicillin or kanamycin resistance. Oligonucleotide primers were purchased from Amitof Biotech and Integrated DNA Technologies. All genes and promoters were PCR amplified using the PTC-200 PCR machine (MJ Research) with PfuTurbo DNA Polymerase (Stratagene). DNA sequences were obtained as follows: gfpmut36 gene from pJBA113 (48), PL(lacO) promoter from pZE12-luc (36), PL(tetO) promoter and ribosome binding site (RBS) sequence from pZE21 (36), and the arabinose operon (pBAD) from pBADHisA (Invitrogen). cis and trans sequences were introduced through oligonucleotide design.

Two PCR reactions were performed to construct the stem-loop cis sequences on the crRNA plasmids (Table 5). In the first PCR reaction, a forward primer for PL(tetO) [or PL(lacO)] was used with a reverse primer for PL(tetO) [PL(lacO)], which contains the cis-repressive sequence and a 5'-labelled phosphate end. In the second PCR reaction, a forward primer for the RBS site, containing the cr loop sequence, was used with a gfp reverse primer. The PCR products were annealed together via blunt-end ligation and cloned into the pZE21G (Table 4) vector using unique restriction enzyme sites. The taRNA sequences (Table 6) were constructed by annealing two single-stranded, reverse complementary oligonucleotides in a DNA hybridization reaction. The double-stranded products (approximately 80-100 bp), containing restriction sites, were subsequently cloned into an ampicillin-resistant plasmid downstream of the pBAD [or PL(tetO)] promoter.

All plasmids were constructed using restriction endonucleases and T4 DNA Ligase from New England Biolabs. Plasmids were introduced into the E. coli XL-10 strain (Stratagene; Tet$^r$ Δ(mcrA)183 Δ(mcrCB-hsdSMR-mrr)173 endA1 supE44 thi-1 recA1 gyrA96 relA1 lac Hte [F proAB lacI$^q$ZDM15 Tn10 (Tet$^r$) Amy Cam$^r$) using standard heat-shock, TSS, transformation protocols (47). The E. coli XL-10 strain, DH5α-pro strain (Clontech), 2.300 strain (Genetic Stock Center no. 5002, λ-, lac122, rpsL135, and thi-1), and wildtype K-12 strain were used for all experiments. All cells were grown in selective media: LB (DIFCO) and either 30 μg/ml kanamycin or 100 μg/ml ampicillin (Sigma). Plasmid isolation was performed using PerfectPrep Plasmid Isolation Kits (Eppendorf). Subcloning was confirmed by restriction analysis. Plasmid modifications were verified by sequencing using the PE Biosystem ABI Prism 377 sequencer.

Gene Expression Analysis

For all experiments, cells were grown overnight in the appropriate conditions, diluted 1:1000, and re-grown prior to collecting RNA samples and measuring GFP expression by flow cytometry. All RNA and GFP measurements were determined during logarithmic growth at $OD_{600}$ 0.4-0.6, measured by a SPECTRAFluor Plus (Tecan). A positive control, pZE21G, was constructed such that the promoter drives the expression of gfpmut3b without the repressive cis element Cis experiments were conducted under two conditions: no anhydrotetracycline (aTc) and 30 ng/ml aTc. An insufficient concentration of TetR protein was present in XL-10 cells to saturate the tetO operator sites. Therefore, in control experiments (FIG. 2B), we observed intermediate levels of GFP expression, which corresponds to intermediate transcription rates. DH5α-pro cells contained higher cellular levels of TetR, and thus demonstrated a lower expression state at no aTc induction Cis/trans experiments were conducted under four conditions: (i) no aTc, no arabinose, (ii) no aTc, 0.25% arabinose, (iii) 30 ng/ml aTc, no arabinose, and (iv) 30 ng/ml aTc, 0.25% arabinose. In these experiments, aTc controls the transcription of crRNA and arabinose controls the expression of taRNA. We measured the expression of the riboregulator systems in two additional strains, lacking TetR protein production: 2.300 strain and wildtype K-12 strain. In these strains, we grew cultures containing riboregulator systems in the absence and presence of arabinose and obtained results consistent with those obtained using the other strains (XL10 and DH5αpro).

GFP Quantitation by Flow Cytometry

All expression data were collected using a Becton Dickinson FACSCalibur flow cytometer with a 488 nm argon laser and a 515-545 nm emission filter (FL1) at low flow rate. Before analysis, cells were pelleted and resuspended in filtered PBS (Life Technologies, pH=7.2) immediately following each time point. Calibrite Beads (Becton Dickinson) were used to calibrate the flow cytometer. Each fluorescent measurement of gene expression was obtained from populations of >100,000 cells. Flow data were converted to ASCII format using MFI software (E. Martz, University of Massachusetts, Amherst). Matlab (Mathworks, Inc., Massachusetts) software was used to filter (in a narrow forward scatter range) and analyze a homogenous population of cells in each sample.

Quantification of Cellular RNA Concentrations:rcPCR Gene Expression Analysis

Real competitive PCR (rcPCR) was carried out in essentially the same way as previously reported (38). The assay designs for 16S rRNA, taRNA and crRNA are described in Table 7. The steps of rcPCR are described briefly below.

Step 1: Reverse transcription. Total RNA samples were obtained from cultures in logarithmic growth. Cultures were immediately placed in RNAprotect (Qiagen), and RNA was isolated using RNeasy Mini Kit (Qiagen). RNA samples were subjected to a DNase I (DNA-free, Ambion) digestion and diluted 10 times before reverse transcription. Each reverse transcription reaction contains 1 mL diluted RNA, 1 mL ImProm-II 5 buffer, 1 mL $MgCl_2$ (25 mM), 0.3 mL dNTP mix (10 mM each), 0.3 mL ImProm-II reverse transciptase (Promega), 0.5 mL random primer (0.5 mg/mL) and 0.9 mL RNAse free water. Only RNA was added first and heated at 70° C. for 5 min and put on ice immediately. The remaining reagents were added and reverse transcription was carried out by incubating at 25° C. for 5 min, followed by 42° C. for 1 hour and finally 70° C. for 15 min to inactivate the reverse transcriptase. All temperature controlled reactions (reverse transcription, PCR amplification and base extension) were carried out in a GeneAmp 9700 thermocycler (ABI).

Step 2: PCR amplification. Reverse transcription products were diluted 10 times before PCR Each PCR reaction contains 1 mL diluted cDNA, 0.5 mL 10 HotStar Taq PCR buffer, 0.2 mL $MgCl_2$ (25 mM), 0.04 mL dNTP mix (25 mM each), 0.02 mL HotStar Taq Polymerase (50 U/mL, Qiagen), 0.01 mL competitor DNA, 1 mL forward and reverse primer (1 mM each) and 2.23 mL $ddH_2O$. The PCR condition was: 95° C. for 15 min for hot start, followed by denaturing at 94° C. for 20 sec, annealing at 56° C. for 30 sec and extension at 72° C. for 1 min for 45 cycles, with final incubation at 72° C. for 3 min.

Step 3: Base extension. PCR products were treated with shrimp alkaline phosphatase (SEQUENOM) for 20 min at 37° C. first to remove excess dNTPs. A mixture of 0.17 mL hME buffer (SEQUENOM), 0.3 mL shrimp alkaline phosphatase (SEQUENOM) and 1.53 mL $ddH_2O$ was added to each PCR reaction. The reaction solutions (now 7 mL each) were incubated at 37° C. for 20 min to remove excess dNTPs, followed by 85° C. for 5 min to inactive the phosphatase. For each base extension reaction, 0.2 mL of selected ddNTP/dNTP mix (SEQUENOM), 0.108 mL of selected extension primer, 0.018 mL of ThermoSequenase (32 U/mL, SEQUENOM) and 1.674 mL $ddH_2O$ were added.

The base extension condition was as follows: 94° C. for 2 min, followed by 40 cycles of 94° C. for 5 sec, 52° C. for 5 sec and 72° C. for 5 sec.

Step 4: Liquid dispensing and MALDI-TOF MS. The final base extension products were treated with SpectroCLEAN (SEQUENOM) resin to remove salts in the reaction buffer. This step was carried out with a Multimek (Beckman) 96 channel auto-pipette. Sixteen μL resin/water solution was added into each base extension reaction, making the total volume 25 μL. After centrifugation (2,500 rpm, 3 min) in a Sorvall Legend RT centrifuge, approximately 10 nL of reaction solution was dispensed onto a 384 format SpectroCHIP (SEQUENOM) pre-spotted with a matrix of 3-hydroxypicolinic acid (3-HPA) by using a MassARRAY nanodispenser (SEQUENOM). A modified Bruker Biflex MALDI-TOF mass spectrometer was used for data acquisitions from the SpectroCHIP. Mass spectrometric data were automatically imported into the SpectroTYPER (SEQUENOM) database for automatic analysis such as noise normalization and peak area analysis. The allelic frequency of 16SrRNa, crRNa, and taRNA were exported to Excel (Microsoft Office) and analyzed. The reported concentrations of crRNA and taRNA in Table 1 are expressed as a percentage of 16SrRNA concentration within each sample.

Table 5 lists cis-repressive RNA sequences in the crRNA constructs, loop containing the YUNR (TTGG) recognition motif, and ribosome binding site (RBS) used herein.

Results

Several features of endogenous riboregulators (17, 33, 34) were used to guide the construction of this artificial post-transcriptional regulatory system. With regard to the crRNA component, three main features were prominent in the design. First, the DNA template for the crRNA is designed according to the following considerations. The cis repressive sequence, which consists of a 19 base pair (bp) reverse complementary sequence to the RBS, is strategically placed directly downstream of (i.e., in the 3' direction from) the promoter and upstream of (i.e., in the 5' direction from) the RBS sequence, so that in the mRNA transcript the cis-repressive sequence is located in the 5' UTR. Importantly, the introduced cis sequence does not alter the coding frame of the targeted gene and does not affect native transcription. Second, a short nucleotide sequence, placed between the cis-repressive sequence and the RBS, permits formation of a hairpin stem-loop structure in which the cis-repressive RNA and the RBS form the stem, and the short intervening nucleotide sequence forms the loop. Third, a YUNR (pyrimidine-Uracil-Nucleotide-puRine) consensus sequence, which has been shown to be an important target for intermolecular RNA complexes in the native RI system (34), is included in the loop region in the constructs described here, and it is generally preferred that the crRNA includes this sequence in the loop region. While not wishing to be bound by any theory, it is believed that this motif directs taRNA-crRNA binding through a linear-loop intermolecular interaction, as shown schematically in FIG. 3C. The taRNA stem contains the nucleotide sequence that is complementary to the cis-repressive sequence. In preferred taRNA elements this sequence, which possesses high sequence similarity to the RBS, is sequestered in the taRNA stem structure to prevent aberrant titration of ribosomes and eliminate any possible pleiotropic effect. Because the intermolecular RNA interactions rely on specific RNA structures, we utilized the Mfold web server (35) using default parameters to generate predicted RNA secondary structures. These predicted RNA secondary structures guided the sequence and assembly of all RNA sequences. In particular, sequences that yielded more than one predicted secondary structure were eliminated.

To assess in vivo repressive ability of the 5'-UTR cis element, four crRNA variants (crRL, crR7, crR10, and crRB) were constructed on episomal plasmids that propagate in *Escherichia coli* (*E. coli*) cells. Four crRNA variants (FIG. 2A), with varying degrees of stem sequence complementarity to the RBS, were constructed for two main reasons: First, to determine the extent of sequence complementarity required for sufficient post-transcriptional repression and second, to investigate if changes in stem sequences, which introduce partial complementarity and result in alternate RNA secondary structures [i.e., RNA duplex (crRL), inner loops (crR7, crRB) and bulges (crR10)], destabilize the stem loop to help generate an open complex when targeted for activation by trans-activating RNA (taRNA) (see Example 2).

We chose the constitutive PL(tetO) promoter (36), a modified version of the native Phage λ PL promoter containing two TetR operator sites, to drive the expression of each crRNA transcript in which transcription can be modulated by the TetR protein and its chemical inducer anhydrotetracycline (aTc). A 25 nucleotide (nt) DNA sequence was cloned 27 nt downstream of the PL(tetO) promoter, such that this cis-repressive sequence is present on the 5' UTR of the mRNA (crRNA). The cis sequence included two sections: a 19 nt stem sequence, complementary or substantially complementary to the RBS, and a 6 nt loop region. A synthetic ribosome binding site from the pZ plasmid system (36) and the gfpmut3b gene (37) were cloned directly downstream of the cis sequence. Single-cell fluorescence measurements of the Green Fluorescent Protein (GFP) were used to monitor the expression state of this post-transcriptional system by flow cytometry. A control plasmid that lacks the cis element and contains an arbitrary sequence upstream of the RBS was also constructed (FIG. 2).

Figure 2B:
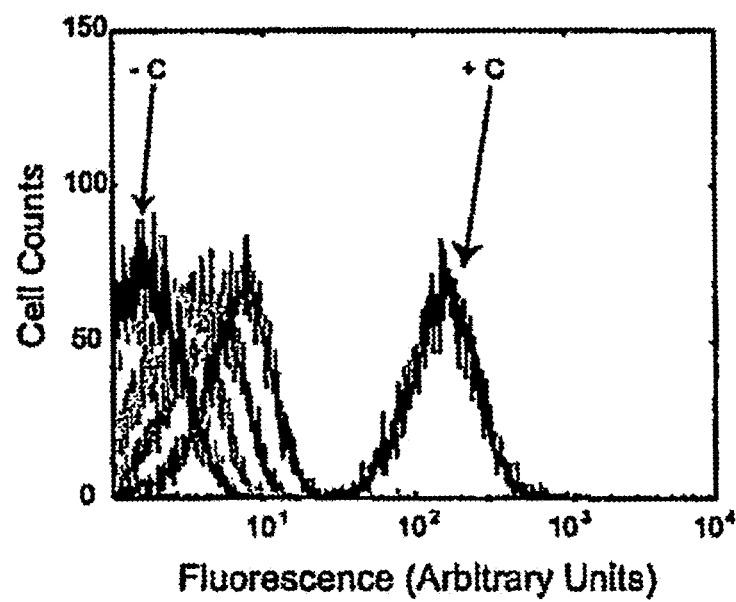
FIGS. 2B and 2C show cis-repression results of crRNA variants (in ascending gray scale): crRL (lightest), crR7, crR10, crRB, and control (darkest, labeled +C). Flow-cytometric results of cRNA variants driving the expression of gfpmut3b at intermediate (FIG. 2B) and high (FIG. 2C) transcription rates are shown. Histograms represent GFP expression of cultures containing each construct in FIG. 2A. crRL (lightest), crR7, crR10, crRB, and control (darkest, labeled +C). Negative control curve (–C) corresponds to fluorescence measurement cells containing plasmids that lack GFP (autofluorescence measurement).
Figure 2C:
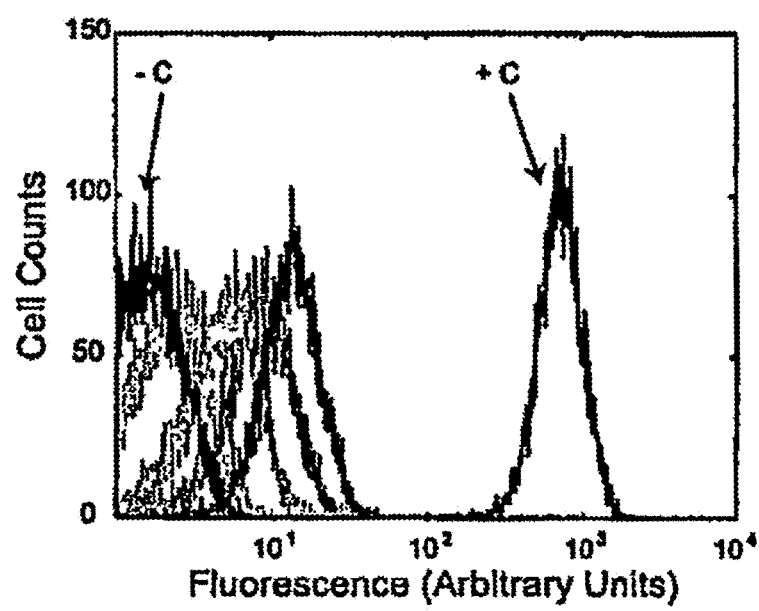

Flow-cytometric measurements from single cells containing control plasmids and constitutive expression of TetR protein show an elevated GFP state at intermediate (no aTc) and high (30 ng/ml aTc) transcription rates (FIGS. 2B,C). Cells possessing plasmids with the upstream cis-repressive elements (crRNAs) were grown under the same conditions. Moderate GFP leakage was detected in cultures containing the crRB variant, which contains reduced cis sequence complementarity to the RBS. Due to the elevated levels of expression, together with a variable secondary structure predicted to lose its recognition site in the stem-loop (FIG. 2A), the crRB variant was not used in subsequent investigation. At intermediate transcription rates (FIG. 2B), crRL cultures show repressed levels of GFP expression indistinguishable from autofluorescence cellular measurements (determined by measuring fluorescence of cells containing plasmids that lack GFP). The crR7 and crR10 cultures, which demonstrate slightly elevated levels of GFP expression, also show dramatic silencing of gene expression. At high transcription (FIG. 2C), we also observe low GFP expression values for all variants indicating that the cis-repressive 5'-UTR element renders striking suppression of post-transcriptional expression. Our results also indicate that the degree of repression is not entirely correlated with predicted $\Delta G_{Mfold}$ values (Table 1) and base-pairing in the stem region [crR7 vs. crR10, crR12 (see below)]. Thus, placement of the mismatches and the resulting structures (i.e., inner loops proximate to the stem-loop and bulges) impact the stability of the hairpin stem-loop and the degree of repression. Furthermore, the observed repression of >96% (intermediate transcription) and >97% (high transcription) (98% when background autofluorescence is subtracted) provides improved silencing when compared to alternative antisense and trans ribozyme systems that target specific open reading frames or RBS sequences (31, 32).

In order to confirm that the observed silencing is due to the presence of translational repression by the cis sequence, we measured cellular mRNA concentrations. Total cell RNA was isolated from cultures containing each crRNA variant and the control plasmid, permitting quantitative measurements of mRNA levels by competitive PCR coupled with matrix-assisted laser desorption/ionization-time-of-flight (MALDI-TOF) mass spectrometry (38). Table 1 lists the measured mRNA concentrations, which are normalized by endogenous levels of 16S rRNA in each sample. We consistently observe a four-fold increase in mRNA concentration upon shifting from intermediate to high transcription rates (+aTc/-aTc). The RNA concentration results also demonstrate that the crRNA variants are present at 40% of the mRNA levels measured from the control cultures. Possible causes of RNA loss include premature transcription termination downstream of the hairpin stem-loop structure or targeted degradation by RNases that cleave double-stranded RNAs (40, 41). Despite the moderate loss of cellular mRNA concentrations, crRNA levels at high transcription (+aTc) are greater than intermediate (-aTc) mRNA control levels indicating that sufficient levels of mRNA are available for ribosomal recognition and can serve as templates for protein synthesis. Together with the GFP data, these results demonstrate that the hairpin stem-loop, which preferentially forms due to the placement of the upstream cis sequence, prevents ribosome binding at the RBS and interferes with post-transcriptional gene expression.

TABLE 4

List of Plasmids

| Plasmid | Description | Parent Plasmid(s) |
| --- | --- | --- |
| pZE21G | ColE1-vector, kanamycin resistance, PL(tetO) producing g/pmut3b | pZE21 (3), pJBA113 (3) |
| pZE21αLG | crRL sequence inserted downstream of PL(tetO) | pZE21G |
| pZE21αBG | crRB sequence inserted downstream of PL(tetO) | pZE21G |
| pZE21α7G | crR7 sequence inserted downstream of PL(tetO) | pZE21G |
| pZE21α10G | crR10 sequence inserted downstream of PL(tetO) | pZE21G |
| pZE21α12G | crR12 sequence inserted downstream of PL(tetO) | pZE21G |
| pZE21α22G | crR22 (short er element) | pZE21G |
| pZE22α12G | crR12 sequence inserted downstream of PL(lacO) | pZE12-luc (3), pZE21α12G |
| pZE15 | ColE1-vector, ampicillin resistance, pBAD promoter | pZE12-luc (3), pBADHis-A[1] |
| pZE15YL | pBAD producing taRL | pZE15 |
| pZE15YB | pBAD producing taRB | pZE15 |
| pZE15YL7 | pBAD producing taR7 | pZE15 |

TABLE 4-continued

List of Plasmids

| Plasmid | Description | Parent Plasmid(s) |
|---|---|---|
| pZE15YL10 | pBAD producing taR10 | pZE15 |
| pZE15YL12 | pBAD producing taR12 | pZE15 |
| pZE15Y12st | taR12 with 5' stabilizer element (7, 8) | pZE15Y12 |
| pZE15Y22 | pBAD producing taR22 | pZE15 |
| pZE11Y12 | PL(tetO) producing taR12 | pZE15Y12, pZE21G |
| pZER21YLαLG | taRL-crRL Riboswitch | pZE15YL, pZE21αLG |
| pZER21Y7αLG | taR7-crRL Riboswitch | pZE15Y7, pZE21αLG |
| pZER21Y10αLG | taR10-crRL Riboswitch | pZE15Y10, pZE21αLG |
| pZER21Y12αLG | taR12-crRL Riboswitch | pZE15Y12, pZE21αLG |
| pZER21YLα7G | taRL-crR7 Riboswitch | pZE15YL, pZE21α7G |
| pZER21Y7α7G | taR7-crR7 Riboswitch | pZE15Y7, pZE21α7G |
| pZER21Y10α7G | taR10-crR7 Riboswitch | pZE15Y10, pZE21α7G |
| pZER21Y12α7G | taR12-crR7 Riboswitch | pZE15YL12, pZE21α7G |
| pZER21YLα10G | taRL-crR10 Riboswitch | pZE15YL, pZE21α10G |
| pZER21Y7α10G | taR7-crR10 Riboswitch | pZE15Y7, pZE21α10G |
| pZER21Y10α10G | taR10-crR10 Riboswitch | pZE15Y10, pZE21α10G |
| pZER21Y12α10G | taR12-crR10 Riboswitch | pZE15Y12, pZE21α10G |
| pZER21YLα12G | taRL-crR12 Riboswitch | pZE15YL, pZE21α12G |
| pZER21Y7α12G | taR7-crR12 Riboswitch | pZE15Y7, pZE21α12G |
| pZER21Y10α12G | taR10-crR12 Riboswitch | pZE15Y10, pZE21α12G |
| pZER21Y12α12G | taR12-crR12 Riboswitch | pZE15Y12, pZE21α12G |
| pZER21YBαBG | taRB-crRB Riboswitch | pZE15YB, pZE21αBG |
| pZER21Y12stα12G | taR12-crR12 Riboswitch + 5' stabilizer element | pZE15Y12st, pZE21α12G |
| pZER21Y22α22G | taR22-crR22 Riboswitch | pZE15Y22, pZE21α22G |
| pZER21Y12Aα12G | taR12A-crR12 Riboswitch, 96% taR-crR duplex | pZER21Y12α12G |
| pZER21Y12Bα12G | taR12B-crR12 Riboswitch, 96% taR-crR duplex | pZER21Y12α12G |
| pZER21Y12Cα12G | taR12C-crR12 Riboswitch, 100% taR-crR duplex | pZER21Y12α12G |
| pZER21U1Y12α12G | taR12-crR12: 3' stem of taR12 binds to 5' UTR of crR12 | pZER21Y12α12G |
| pZER21U2Y12α12G | taR12-crR12: 3' stem of taR12 binds to 5' UTR of crR12 | pZER21Y12α12G |
| pZER21U3Y12α12G | taR12-crR12: 3' stem of taR12 binds to 5' UTR of crR12 | pZER21Y12α12G |
| pZER22Y12-1α12G | taR12-crR12 Riboswitch II; +1 transcription of taR12 | pZE11Y12, pZE22α12G |
| pZER22Y12-3α12G | taR12-crR12 Riboswitch II; +3 transcription of taR12 | pZE11Y12, pZE22α12G |
| pZER22Y12-5α12G | taR12-crR12 Riboswitch II; +5 transcription of taR12 | pZE11Y12, pZE22α12G |
| pZER22Y12-19α12G | taR12-crR12 Riboswitch II; +19 transcription of taR12 | pZE11Y12, pZE22α12G |
| pZER22Y12-21α12G | taR12-crR12 Riboswitch II; +21 transcription of taR12 | pZE11Y12, pZE22α12G |
| pZER22Y12-23α12G | taR12-crR12 Riboswitch II; +23 transcription of taR12 | pZE11Y12, pZE22α12G |

TABLE 5

Sequences of Cis-repressive RNA Sequences, Loop, RBS, and crRNA Constructs. All sequences are shown 5' to 3' and represented in the form of their corresponding DNA sequences as used in the cloning steps.

| | | Sequence ID NO: |
|---|---|---|
| Cis-Repressive Sequence | | |
| C | GGACGCACTGACCGAATTC | SEQ ID NO: 3 |
| crRL | CTACCTTTCTCCTCTTTAAT | SEQ ID NO: 4 |
| crRB | TTCTCTAGTCCTCCTTAT | SEQ ID NO: 5 |
| crR7 | CTACCTTTCTCCTCTAGGA | SEQ ID NO: 6 |
| crR10 | CTACCTATCTGCTCTTGAA | SEQ ID NO: 7 |
| crR12 | CTACCATTCACCTCTTGGA | SEQ ID NO: 8 |
| crR22 | CTACCATTCACCTGGA | SEQ ID NO: 9 |
| Loop | TTTGGGT | |
| RBS | ATTAAAGAGGAGAAA | SEQ ID NO: 10 |
| Sequence of Cis-Repressive RNA Constructs | | |
| C | GGACGCACTGACCGAATTCATTAAAGAGGAGAAAGGTACCATG | SEQ ID NO: 11 |
| crRL | CTACCTTTCTCCTCTTTAATTTTGGGTATTAAAGAGGAGAAAGGTACCATG | SEQ ID NO: 12 |
| crRB | CTCTAGTCCTCCTTATTTTGGGTATTAAGAGGAGAAAGGTACCATG | SEQ ID NO: 13 |
| crR7 | CTACCTTTCTCCTCTAGGATTTGGGTATTAAAGAGGAGAAAGGTACCATG | SEQ ID NO: 14 |
| crR10 | CTACCTATCTGCTCTTGAATTTGGGTATTAAAGAGGAGAAAGGTACCATG | SEQ ID NO: 15 |
| crR12 | CTACCATTCACCTCTTGGATTTGGGTATTAAAGAGGAGAAAGGTACCATG | SEQ ID NO: 16 |
| crR22 | CTACCATTCACCTCTTGGATTTGGGTATTAAAGAGGAGAAAGGTACCATG | SEQ ID NO: 17 |

Example 2

Synthesis and Activity of Trans-Activating RNA Elements

This example describes the creation of DNA constructs that provide templates for synthesis of a variety of different trans-activating RNA elements that operate in conjunction with corresponding cis-repressive RNA elements described in Example 1. The example further presents measurements demonstrating the ability of these RNA elements to activate translation of coding sequences whose translation was previously repressed by the corresponding cis-repressive RNA.

Materials and Methods

See example 1.

Results

Small, trans-activating RNAs (taRNAs), designed to cause the crRNAs described in Example 1 to undergo structural transformation to expose the RBS and initiate translation, were produced. The taRNA sequences were selected so as to direct loop (crRNA)-linear (taRNA) RNA pairing. The mode of RNA-RNA interaction was designed based on several characterized natural RNA systems (17, 34), e.g., the hok/sok postsegregational killing system of plasmid R1 (34). While not wishing to be bound by any theory, our artificial riboregulator system undergoes the following proposed mechanism: i) the 5'-linear region of the taRNA recognizes a YUNR consensus sequence (UUGG) (34) on the loop of crRNA, ii) pairing between complementary nucleotides occurs in the presence of an unstable loop-tail complex, and iii) an intermolecular RNA duplex structure forms (FIG. 3C). The resulting RNA duplex induces a structural change, which permits ribosomal recognition of the previously obstructed RBS followed by translation. Because the final RNA complex would otherwise include 26 consecutive base pairs, two bulges were intentionally introduced into its structure to provide immunity from RNase III cleavage of RNA duplexes (40, 41).

In order to assess the activation ability of each crRNA variant, unique taRNA structures were designed for each crRNA target ensuring that the final duplex structures all contain 24 base pair matches and two dispersed bulges. Table 6 presents sequences of the taRNA molecules that were generated. These taRNA molecules were produced in vivo from the arabinose operon (pBAD), such that their transcription rates could be modulated by the presence of arabinose sugar and AraC protein (endogenously present in the cell). Initially, three taRNA-crRNA cognate pairs (taRL-crRL, taR7-taR7, and taR10-taR10) were investigated to measure the resulting activation of GFP expression in the presence of the small trans-activating RNAs. Cultures containing the crRL and crR7 variants show no detectable increase in GFP expression at high arabinose induction of taRL and taR7, respectively. However, upon induction of taR10, cultures containing crR10 exhibit 5× increase in GFP expression (FIGS. 3D,F).

Based on the results obtained with the initial set of taRNA-crRNA pairs, we constructed another taRNA-crRNA pair: taR12 and crR12 (FIGS. 3A, B). The crR12 variant, similar in structure to crR10, also contains three dispersed bulges in its predicted secondary structure. In the absence of arabinose, cells containing crR12 show a low, near autofluorescence repressed state, and upon arabinose induction, we observe a 10× increase in GFP expression (FIGS. 3E, F). These results suggest that partial helix destabilization (e.g., presence of bulges) in crRNA seems to be important for the taRNA to mediate conversion between a closed and open complex to form an intermolecular RNA duplex, which enables protein translation. As compared to the endogenous DsrA-RpoS system, which exhibits 3× activation (17), our results demonstrate significantly improved level of activation.

In FIG. 3F, we present the dose-response curves in which each point represents the averaged response of a population to a particular level of induction with arabinose. Average response was obtained by measuring mean GFP fluorescence from a uniform population of cells using flow cytometry. Qualitatively similar dose-response curves were obtained for both riboregulator pairs: We observed no activation at low ($<10^{-4}$%) arabinose concentrations, followed by a rise in activation at intermediate ($10^{-4}$-$10^{-2}$%) arabinose concentrations, and finally a high state which plateaus at elevated levels ($>10^{-2}$%) of arabinose. These data show tunable activation of post-transcriptional expression through the controlled introduction of trans-activating RNA. Interestingly, the taR12:crR12 pair demonstrates a larger dynamic range than the taR10:crR10 riboswitch. One possible explanation for this result is the following: Scrutiny of the flow cytometric histograms depict greater cis repression and higher trans activation for the crR12 variant (FIG. 3E) than for the crR10 variant (FIG. 3D) resulting in greater separation between low and high states. More specifically, these observations may result from the stability of RNA secondary structures and the efficiency of intramolecular (crRNA) vs. intermolecular (taRNAcrRNA) RNA interactions, all of which may be important in the ultimate phenotypic response of this post-transcriptional system

TABLE 6

Sequences of Trans-activating RNA Constructs. 5'-st represents the 5' stabilizer element inserted in front of taR12. All sequences are shown 5' to 3' and represented in the form of their corresponding DNA sequences as used in the cloning steps.

| Construct/Sequence | | Sequence ID NO |
|---|---|---|
| taRL | ACACCCAAATTAAAGAGGAGAAAGGTA GTGGTGGTTAATGAAAATTAACTTACT ACTACCTTTTTCTTAGA | SEQ ID NO: 18 |
| taRB | ACGCCCAATAAGGAGGATAGAGTGGTG GTTAATGAAAATTAACTTACTACTTAG TTTTAGA | SEQ ID NO: 19 |
| taR7 | ACACCCAAATCCTAGGGAGAATGGTAG TGGTGGTTAATGAAAATTAACTTACTA CTACTTTTTCATAGA | SEQ ID NO: 20 |
| taR10 | ACACCCAAATTATGAGCAGATTGGTAG TGGTGGTTAATGAAAATTAACTTACTA CTACTTTCTTAGA | SEQ ID NO: 21 |
| taR12 | ACCCAAATCCAGGAGGTGATTGGTAGT GGTGGTTAATGAAAATTAACTTACTAC TACCATATATCTCTAGA | SEQ ID NO: 22 |
| taR12A | ACCCAAATCCAGGAGGTGAATGGTAGT GGTGGTTAATGAAAATTAACTTACTAC TACCATATATCTCTAGA | SEQ ID NO: 23 |
| taR12B | ACCCAAATCCAAGAGGTGATTGGTAGT GGTGGTTAATGAAAATTAACTTACTAC TACCATATATCTCTAGA | SEQ ID NO: 24 |
| taR12C | ACCCAAATCCAAAGAGGTGAATGGTAA GTGGGTGGTTAATGAAAATTAACTTAC TACTACCATATATTCTCTAAGA | SEQ ID NO: 25 |
| taRU112 | ACCCAAATCCAGGAGGTGATTGGTAGT GGTGGTTAATGAAAATTAACTTACTAA AATCGGACATCTCTAGA | SEQ ID NO: 26 |
| taRU212 | ACCCAAATCCAGGAGGTGATTGGTAGT GGTGGTTAATGAAAATTAACTTTACTA CTTACGCGTCATATCTCTAGA | SEQ ID NO: 27 |

TABLE 6-continued

Sequences of Trans-activating RNA Constructs.
5'-st represents the 5' stabilizer element
inserted in front of taR12. All sequences are
shown 5' to 3' and represented in the form of
their corresponding DNA sequences as used in
the cloning steps.

| Construct/Sequence | | Sequence ID NO |
|---|---|---|
| taRU312 | ACCCAAATCCAGGAGGTGATTGGTAGT GGTGGTTAATGAAAATTAACTTACTAC GATCAGTGATCTCTAGA | SEQ ID NO: 28 |
| taR22 | ACCCAAATCCAGGTGTATGGTAGTGGT GGTTAATGAAAATTAACTTACTACCAT TCACCTCGATCTAGA | SEQ ID NO: 29 |
| 5'-st | GGGUCCGCUAUGAGGUAAAGUGUCAUA GCGGGCCC | SEQ ID NO: 30 |

Example 3

Specificity of Cis-Repressive and Trans-Activating RNA Pairs

Materials and Methods

Equilibrium constant measurements: The equilibrium constants for complexes between the cis-repressive and trans-activating RNAs can be measured in several different ways. Classic methods include electrophoretic mobility shift assays in polyacrylamide gels containing divalent cations (49). Here, we use an approach based on the property of reverse transcriptase, which stalls and terminates on stable RNA duplexes. When hybridized to crRNA, taRNA creates an obstacle for the reverse transcriptase, yielding a truncated product. The amount of truncated transcripts versus full length transcripts is assayed by polyacrylamide gel electrophoresis. From these data one can calculate equilibrium association and dissociation constants. This method is advantageous over classic methods because it uses fluorescence rather than radioactive probes and does not involve RNA cross-linking agents.

Step 1: In vitro RNA transcription. The RNA samples were synthesized using the MAXIscript T7 In Vitro Transcription Kit (Ambion). Prior to transcription, the genes of interest were PCR amplified from the respective plasmids. Forward primers contained the T7 promoter sequence at the 5' overhang end. The reverse primers were selected to obtain the desired length of the in vitro transcript (Table 7). Each of the in vitro transcription reactions contained 300-500 ng of PCR product, yielding approximately 3 μg of RNA (Ambion protocols). The template DNA was removed by DNAse I treatment (Ambion DNA-free). Products of in vitro transcription were purified by phenol extraction followed by ethanol precipitation (47). After removal of unincorporated ribonucleotides, the transcripts were transferred to Microtest™ 96-well UV-Vis transparent clear plates (BD Falcon) and quantified by UV absorbance (260 nm) using a SPECTRAFluor Plus (Tecan).

Step 2: Complex formation. For each of the riboregulator pairs, six samples with different molar ratios of taRNA-crRNA were prepared. The concentrations of taRNA in the six samples were: 1.0/μM, 0.50 μM, 0.25 μM, 0.13 μM, 0.06 μM, and 0.03 μM. The concentrations of crRNA were 0.20 μM and 0.01 μM for cognate (e.g., taR12-crR12) and non-cognate (e.g., taR10-crR12) pairs, respectively. Each of the samples contained 10 μM Tris (pH=7), 10 μM MgCl$_2$, 1 pM KCl, 1 U of RNAse inhibitor (Applied BioSystems), and 0.4 pM of Cy5-labeled reverse transcription primer (5'-Cy5-CTTCACCCTCTCCACTGAC-3') (SEQ ID NO: 31). The reverse transcription primer was designed to anneal the crRNA approximately 80 nucleotides downstream of the gfpmut3b start codon and contained the Cy-5 label at the 5' end. The samples were given 20 minutes to equilibrate at 37° C.

Step 3: Reverse transcription. Reverse transcription was carried out using the TaqMan Reverse Transcription Kit (Applied BioSystems). For each reverse transcription reaction, 5 μL of the complex obtained in the previous step and 2.5 μL of the RT reagents were combined. Each reaction contained 5.5 mM MgCl$_2$. The reaction conditions were as follows: 15 minutes at 37° C., followed by addition of 5 μL of stop solution (formamide:EDTA:bromphenol blue). Reaction products were eluted in denaturing 6% polyacrylamide gel (6M urea) and analyzed using ALF sequencing system (Amersham Biosciences). The dideoxy sequencing reaction of the crR7 clone was used as a reference DNA ladder.

Table 7 presents details of the real-time competitive PCR assay design including a list of primers used to amplify RT-PCR products obtained from RNA cell preparations. A terminator mix using three different ddNTPs and one dNTP. For example, CGT mix for 16S RRNA is ddCTP/ddGTP/ddTTP/dATP. Table 8 presents a list of primers used for in vitro PCR amplification.

Results

To determine if the artificial riboswitch pairs demonstrate high specificity, we investigated all 16 combinations (L, 7, 10, and 12) of the taRNA-crRNA constructs. In FIG. 3G, we present results from separate cultures containing crR12 and four different taRNAs (taRL, 7, 10, 12). At no arabinose induction, we measure effective cis-repression at near autofluorescence levels of GFP expression and nearly undetectable concentrations of taRNAs, obtained by competitive PCR coupled with MALDI-TOP mass spectrometry (38). Upon arabinose induction, we detect a dramatic increase in RNA concentration of all taRNA variants, yet we only observe 10× activation at the protein level (GFP) in the taR12:crRI2 cognate pair (FIG. 3G). The same experiments were conducted with the crRL, 7, 10 variants, and at high taRNA levels, GFP activation is only observed for the taR10-crR10 cognate pair. Thus, these results indicate that taRNA-crRNA complexes, which interact and undergo structural rearrangements to expose the RBS, rely on highly specific cognate RNA pairings.

These constructs were subsequently used to prepare DNA templates by PCR for in vitro transcription of RNA fragments. The transcribed RNAs were produced from the T7 promoter, and all taRNA-crRNA pairs were investigated to assess the in vitro specificity of interactions.

Figure 6:
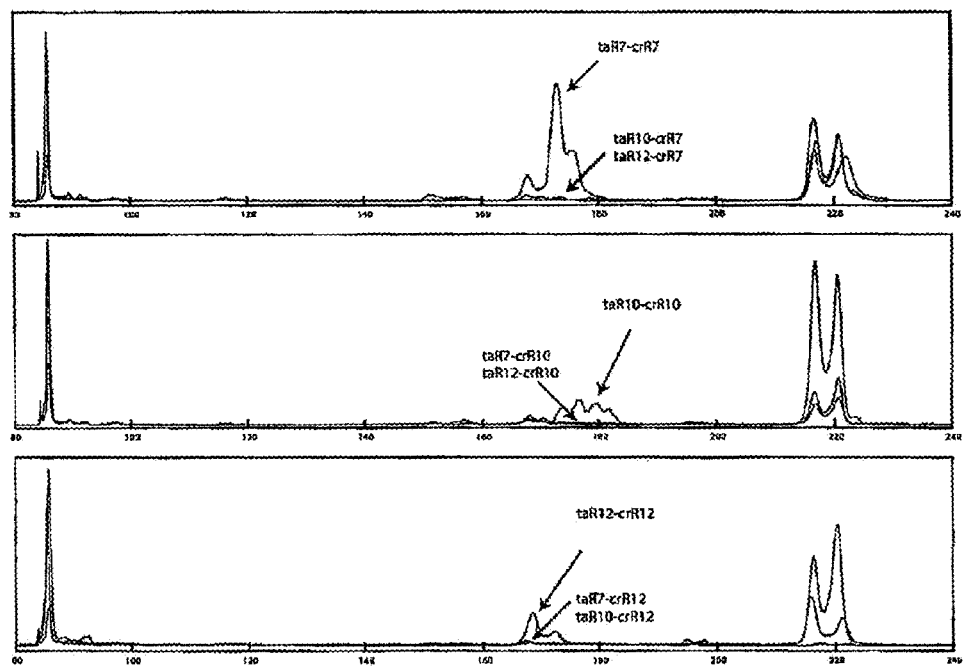
FIG. 6 shows reverse transcription profiles of complexes between crR7 (upper), crR10 (middle), crR12 (lower), and taR7, taR10, and taR12, as indicated with arrows. The peaks at 165-185 min and 210-230 min correspond to truncated transcripts and full length transcripts, respectively. All taRNA-crRNA pairings are denoted by arrows.

We first conducted preliminary experiments using fixed concentrations of cis-repressive and trans-activating RNAs. The x-axis in FIG. 6 corresponds to elution time and can be mapped to nucleotide sequences of cis-repressive RNAs using dideoxy sequencing protocols (39). We found that the time intervals 165-185 min and 210-230 min correspond to truncated transcripts and full length transcripts, respectively. It is remarkable that the cognate pairs (i.e., taR7-crR7, taR10-crR10, and taR12crR12) have substantial peaks corresponding to taRNA-crRNA complex, while the non-cognate pairs show almost no interaction. Therefore, we expect that: (i) the equilibrium association constants of the cognate pairs have much higher values those of the non-cognate pairs and (ii) in order to determine the equilibrium constants for non-cognate pairs, one must use an excess of taRNA to obtain a detectable amount of the taRNA-crRNA complex.

Figure 7:
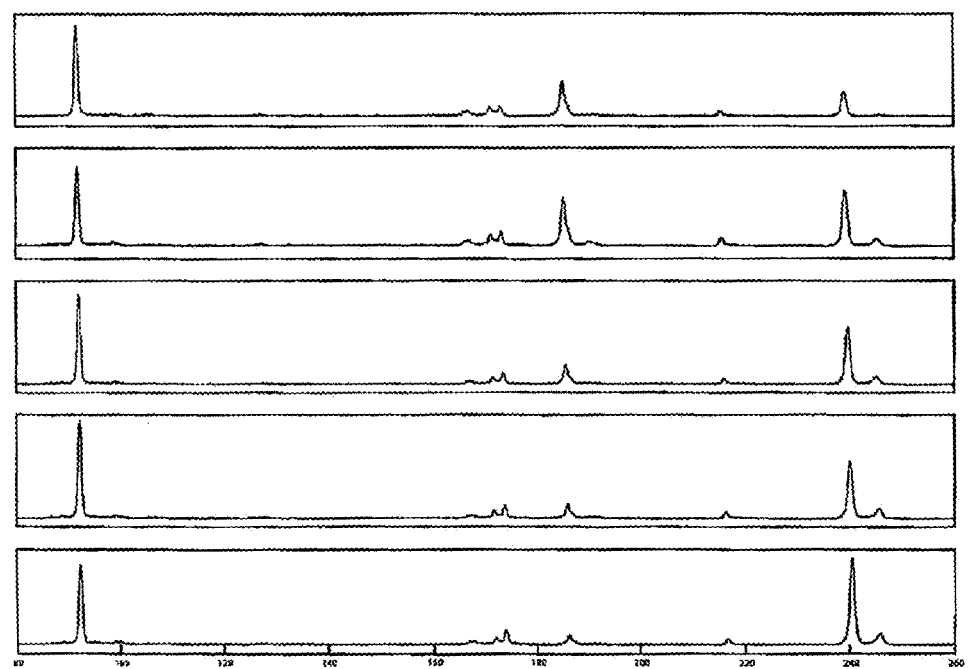
FIG. 7 shows reverse transcription profiles of the taR7-crR12 pair. The concentration of crR12 is kept constant (0.01 μM; the concentration of taR7 decreases over lanes 1-6. Lanes represent (from top to bottom) 1.0 μM, 0.5 μM, 0.25 μM, 0.13 μM, 0.06 μM, and 0.03 μM, respectively. The peaks are: 92 min—RT primer; 170-180 min—termination on cis-repressive secondary structure; 180-190 min—termination on the crRNA-taRNA complex; 210-220 min—termination on secondary structure (minor); 240 min—full length reverse transcript.

Determination of equilibrium association constants for complexes between taRNA and crRNA was performed as described above. Reverse transcription profiles were obtained for each of nine taRNA-crRNA pairs at six different concentrations of taRNA FIG. 7 is an example profile, specifically for the taR7-crR12 pair. The peaks are: 92 minutes (primer); 170-180 minutes (due to termination on cis repressive secondary structure); 180-190 minutes (termination on the taRNA-crRNA complex); 210-220 minutes (minor termination on additional secondary structure); 240-250 minutes (full length reverse transcript of crRNA). Each curve was integrated between 180 and 200 minutes and between 210 and 250 minutes using Fragment Manager (Pharmacia Biotech). The ratio of the integrals are equal to the ratio of equilibrium concentrations of the taRNA-crRNA complex and free crRNA, respectively.

Figure 8:
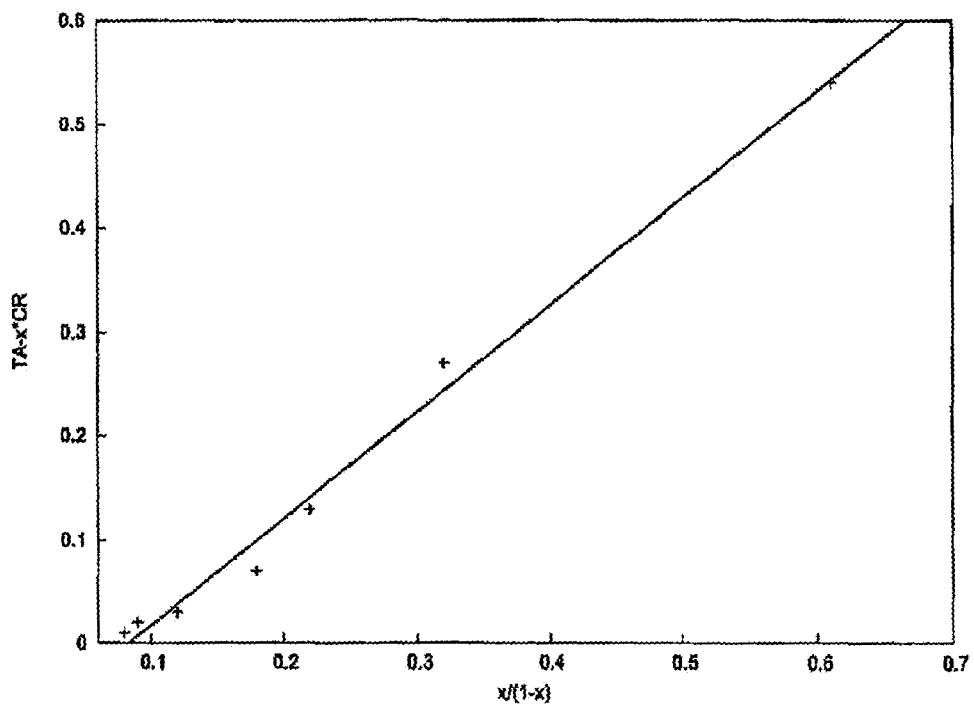
FIG. 8 shows determination of equilibrium association and dissociation constants for the taR7-crR12 pair. Here, CR and TA denote the initial concentrations of crR12 and taR7, respectively; $x=S_c/(S_c+S_f)$, where $S_c$ and $S_f$ are the peak areas of the complex and the full length transcript. The equation of the linear regression line is TA−x·CR=1.03·x/(1−x)−0.008; $K_D$ is 1.03 μM, $K_A$ is $9.7 \times 10^5$ M$^{-1}$.

From these data, the equilibrium dissociation constant was calculated as in reference 50, namely, the equilibrium dissociation constant KD for the reaction cr+ta<--->cr·ta is $K_D=[cr][ta]/[cr \cdot ta]$, where square brackets denote equilibrium concentrations. If CR and TA correspond to the initial concentrations of crRNA and taRNA, respectively, then, $CR=[cr]+[cr \cdot ta]$ and $TA=[ta]+[cr \cdot ta]$. Alternatively, [cr·ta]/CR is equal to $x=S_c/(S_c+S_f)$, where $S_c$ and $S_f$ are the peak areas of the complex and the full length transcript, respectively. Therefore, $x \cdot K_D=(1-x)(TA-x \cdot CR)$. Thus, $K_D$ is equal to the slope of the linear regression of TA−x·CR versus x/(1−x). In FIG. 8 we show an example calculation for the crR12-taR7 pair. Here $K_D$ is 1.03 μM, and $K_A$, which is the inverse of $K_D$, is $9.7 \cdot 10^5 M^{-1}$.

We were able to measure the equilibrium association constants for the 7, 10, and 12 pairs. The association constants (Table 2) of cognate pairs (i.e., ta7-cr7, ta10-cr10, and ta12-cr12) demonstrate greater than 10× higher values than non-cognate pairs (i.e., ta10-cr7, ta12-cr10, etc.). These data are consistent with the measurements of fold change of fluorescence, in which the target pairs show a remarkable increase in gene expression. Interestingly, the taR12-crR12 pair had the biggest fold change of fluorescence, although the association constants of all cognate pairs were of the same order of magnitude. The discrepancy we observe may be caused by differing conditions of RNA-RNA interaction between in vitro and in vivo studies. In addition, other factors, such as concentration of small ions or presence of proteins in the cell, may influence these interactions. In principle, the in vitro studies show that the taRNA-crRNA interaction for the non-cognate pairs is not thermodynamically favorable when compared to the cognate pairs.

TABLE 7

Real-competitive PCR Assay Design.

| Assay: 16SrRNA | PCR Primer 1: | 5'-ACGTTGGATGGGAGACTGCCAGTGATAAAC (SEQ ID NO: 32) |
|---|---|---|
| | PCR Primer 2: | 5'-ACGTTGGATGTGTAGCCCTGGTCGTAAGG (SEQ ID NO: 33) |
| | Extension Primer: | 5'-GAGGAAGGTGGGGGATGACGT (SEQ ID NO: 34) |
| | Terminator Mix: | CGT |
| | Competitor Seq: | 5'-TGTAGCCCTGGTCGTAAGGGCCATGATG-ACTTCACGTCATCCCCACCTTCCTCCAG-TTATCACTGGCAGTCTCC (SEQ ID NO: 35) |
| Assay: crRNA | PCR Primer 1: | 5'-ACGTTGGATGGGAGAGGGTGAAGGTGATGC (SEQ ID NO: 36) |
| | PCR Primer 2: | 5'-ACGTTGGAAGAGGTAGTTTTCCAGTAGTGC (SEQ ID NO: 37) |
| | Extension Primer: | 5'-CATACGGAAAACTTACCCTT (SEQ ID NO: 38) |
| | Terminator Mix: | ACT |
| | Competitor Seq: | 5'-TGTAGCCCTGGTCGTAAGGGCCATGATGAC-TTCACGTCATCCCCACCTTCCTCCAGTTTAT-CACTGGCAGTCTCC (SEQ ID NO: 39) |
| Assay: taRNA | PCR Primer 1: | 5'-ACGTTGGATGTTTCTCCATAGTCGACACCC (SEQ ID NO: 40) |
| | PCR Primer 2: | 5'-ACGTTGGATGCTGCCGCCAGGCATCTAGAG (SEQ ID NO: 41) |
| | Extension Primer: | 5'-GAAAATTAACTTACTACTACC (SEQ ID NO: 42) |
| | Terminator Mix: | CGT |
| | Competitor Seq: | Plasmid construct taR 12 (for taR L, 10) or Plasmid construct taRL (for taR 12) |

TABLE 8

Primers for In Vitro PCR Amplification.
T7 = 5'-TAATACGACTCACTATAGG-3' (SEQ ID NO: 43).
The same set of primers could be used for all crRNA variants because they all contained the same 5' and 3' ends. Due to variable 5' sequences on the taRNA constructs, unique primers were designed for each PCR amplification. The same reverse primer was used in taRNA PCR reactions.

| Construct | PCR Primer (forward) |
|---|---|
| crR7, 10, 12 | 5'-ATTACTCGAG-T7-TCAGCAGGACGCACTGACC (SEQ ID NO: 44) |
| taR7 | 5'-ATTACTCGAG-T7-ACCCAAATCCTAGCGGAG (SEQ ID NO: 45) |
| taR10 | 5'-ATTACTCGAG-T7-ACCCAAATTCATGAGCAGATTG (SEQ ID NO: 46) |
| taR12 | 5'-ATTACTCGAG-T7-ACCCAAATCCAGGAGGTG (SEQ ID NO: 47) |
| Construct | PCR Primer (reverse) |
| crR7, 10, 12 | 5'-GTCCAAGCTTTTATTTGTATAGTTCATCCA (SEQ ID NO: 48) |
| taR7 | |
| taR10 | 5'-ACCACCGCGCTACTG (SEQ ID NO: 49) |
| taR12 | |

Example 4

Alternate Promoter Systems Demonstrate Modular Nature of System

One advantageous feature of the present invention is its modular nature, in that it does not require use of specific promoters and does not target specific coding sequences. To demonstrate the modular nature of the system, the pBAD and PL(tetO) promoters were replaced with the PL(tetO) and PL(lacO) promoeres (36), respectively. In this scheme, PL(lacO) drives the expression of crR12 whereas PL(tetO) produces taR12. Similar to the system described in the examples above, we observe near autofluorescence levels of repression from crR12 GFP expression. Through the use of different promoters, we also demonstrate that the riboregulators functions independent of specific promoters and thus can be utilized with any promoter of choice.

In the new riboregulator system, we chose to transcribe taR12 from the following six different positions relative to the transcription start site (36) of PL(tetO): +1, +3, +5, +19, +21, and +23. No detectable activation was observed in the +1, +19, +21, and +23 variants; however, the +3 and +5 variants demonstrated 9× and 13×GFP activation, respectively. No detectable activation was observed in the +1, +19, +21, and +23 variants; however, the +3 and +5 variants demonstrated 9× and 13×GFP activation, respectively. These data reveal an important mechanistic feature of this system: the taRNA, which targets the consensus loop of the crRNA, sensitively depends on an accessible 5' linear complementary sequence in the crRNA. While not wishing to be bound by any theory, it is possible that an elongated (+19, +21, +23), or truncated (+1), 5' end on the taRNA interferes with taRNA-crRNA interaction, preventing stable intermolecular duplex formation We note also that the +1 variant lacks the YUNR motif, further suggesting the importance of this sequence element.

Example 5

Variant Trans-Activating RNA Elements Reveal Important Structural Features

We designed several experiments to determine the effect of alternations in the taR12 and/or crR12 sequences on the 10× activation observed in the taR12-crR12 riboregulator pair. In an attempt to construct a hairpin stem-loop that is more susceptible to open complex formation upon taR12 induction, we first decreased the number of base-pairs, maintaining three dispersed bulges, in the cis stem sequence of crR12. While cells containing these variants exhibited similar levels of activation to the original constructs, the dynamic range was significantly reduced due to less stable stem loops resulting in elevated low states. In an effort to increase the cellular concentration of the trans-activating RNA, we introduced a previously described (32, 42) stabilizer element at the 5' end of taR12. Cultures containing the 5'-stabilized taR12 transcripts at high concentrations show no activated state above the repressed state established by crR12, suggesting that this stabilizer element may interfere with taR12 recognition of its loop target on crR12. This result, which is consistent with the results obtained using taRNAs transcribed from sites at positions +19, +21, +23 from the transcription start site (see Example 4) suggests that it is preferable to avoid an overly long unpaired sequence at the 5' end of the taRNA in order to preserve trans-activation.

Next, we pursued two approaches to generate a more stable taR12-crR12 duplex. First, we created three additional taR12 variants with greater than 95% and 100% sequence complementarity to the crRNA. Second, we constructed three more taR12 variants such that the 3' end of the taR12 stem, which is exposed in duplex formation, binds to the 5' UTR directly upstream of the cis sequence. Both sets of variants showed no detectable increase in the 10× level of activation. Table 6 lists the taRNA variants that were produced.

The foregoing description is to be understood as being representative only and is not intended to be limiting. Variations on the designs of cis/trans riboregulators described herein, and alternative methods for making and using them will be apparent to one of skill in the art and are intended to be included within the accompanying claims.

REFERENCES

1. R. F. Gesteland, T. R. Cech, J. F. Atkins, *The RNA World, Second Edition* (Cold Spring Harbor Laboratory Press, New York, 1999).
2. G. F. Joyce, *Nature* 418, 214 (2002).
3. K. Kruger, et al., *Cell* 31, 147 (1982).
4. C. Guerrier-Takada, K. Gardiner, T. Marsh, N. Pace, S. Altman, *Cell* 35, 849 (1983).
5. J. A. Doudna, T. R. Cech, *Nature* 418, 222 (2002).
6. S. R. Eddy, *Nat. Rev. Genet.* 2, 919 (2001).
7. P. Stougaard, S. Molin, K. Nordstrom, *Proc. Natl. Acad. Sci. USA* 78, 6008 (1981).
8. E. G. H. Wagner, R. W. Simons, *Annu. Rev. Microbiol.* 48, 713 (1994).
9. R. C. Lee, R. L. Feinbaum, V. Ambros, *Cell* 75, 843 (1993).
10. W. Winkler, A. Nahvi, R. R. Breaker, *Nature* 419, 952 (2002).
11. A. Nahvi, et al., *Chem. Biol.* 9, 1043 (2002).
12. J. Johansson, et al., *Cell* 110, 551 (2002).
13. A. Mironov, et al., *Cell* 111, 747 (2002).
14. W. Winkler, S. Cohen-Chalamish, R. R. Breaker, *Proc. Natl. Acad. Sci. U.S.A.* 99, 15908 (2002).
15. M. T. Morita, et al., *Genes Dev.* 13, 655 (2002).
16. M. Mandal, B. Boese, J. E. Barrick, W. C. Winkler, R. R. Breaker, *Cell* 113, 577 (2003).
17. R. A. Lease, M. Belfort, *Proc. Natl. Acad. Sci. U.S.A.* 97, 9919 (2000).
18. D. P. Bartel, J. W. Szostak, *Science* 261, 1411 (1993).
19. M. N. Stojanovic, D. Stefanovic, *Nat. Biotechnol.* 21, 1069 (2003).
20. D. S. Wilson, J. W. Szostak, *Annu. Rev. Biochem.* 68, 611 (1999).
21. E. Winfree, F. Liu, L. A. Wenzler, N. C. Seeman, *Nature* 394, 539 (1998).
22. A. D. Ellington, J. W. Szostak, *Nature* 346, 818 (1990).
23. C. Tuerk, L. Gold, *Science* 249, 505 (1990).
24. G. F. Joyce, *Gene* 82, 83 (1989).
25. R. R. Breaker, *Chem. Rev.* 97, 371 (1997).
26. A. L. Cheung, C. Wolz, M. R. Y M R, A. S. Bayer, *J. Bacteriol.* 177, 3220 (1995).
27. M. Hensel, et al., *Science* 269, 400 (1995).
28. B. J. Akerley, et al., *Proc. Natl. Acad. Sci. U.S.A.* 95, 8927 (1998).
29. F. Arigoni, et al., *Nat. Biotechnol.* 16, 851 (1998).
30. Y. Ji, et al., *Science* 293, 2266 (2001).
31. E. G. H. Wagner, K. Flardh, *Trends in Genetics* 18, 223 (2002).

32. H. M. Engdahl, M. Lindell, E. G. H. Wagner, *Antisense Nucleic A.* 11, 29 (2001).
33. E. Morfeldt, D. Taylor, A. von Gabain, S. Arvidson, *EMBO J* 14, 4569 (1995).
34. T. Franch, M. Petersen, E. G. H. Wagner, J. P. Jacobsen, K. Gerdes, *J. Mol. Biol.* 294, 1115 (1999).
35. M. Zuker, *Nucleic Acids Res.* 31, 3406 (2003).
36. R. Lutz, H. Bujard, *Nucleic Acids Res.* 25, 1203 (1997).
37. B. P. Cormack, R. C. Valdivia, S. Falkow, *Gene* 173, 33 (1996).
38. C. Ding, C. R. Cantor, *Proc. Natl. Acad. Sci. U.S.A.* 100, 3059 (2003).
39. Sanger et. al. *Proc. Natl. Acad. Sci. U.S.A.* 74, 5463 (1977).
40. T. A. H. Hjalt, E. G. H. Wagner, *Nucleic Acids Res.* 23, 571 (1995).
41. D. Court, *Control of Messenger RNA Stability* (Academic Press, 1993), pp. 71-116.
42. B. J. Emory S A, Bouvet P, *Genes Dev.* 6, 135 (1992).
43. S. Altuvia, E. G. H. Wagner, *Proc. Natl. Acad. Sci. U.S.A.* 97, 9824 (2000).
44. J. Hasty, D. McMillen, J. J. Collins, *Nature* 420, 224 (2002).
45. C. C. Guet, M. B. Elowitz, W. Hsing, S. Leibler, *Science* 296, 1466 (2002).
46. M. Z. D. T. D. H. Mathews, J. Sabina, *J. Mol. Biol.* 288, 911 (1999).
47. J. Sambrook, E. F. Fritsch, T. Maniatis, *Molecular Cloning: A Laboratory Manual, Second Edition* (Cold Spring Harbor Laboratory Press, Plainview, N.Y., 1989).
48. J. B. Andersen et al., *Appl. Environ. Microbiol.* 64, 2240 (1998).
49. A. M. Pyle, J. A. McSwiggen, T. R. Cech, *Proc. Natl. Acad. Sci. USA.*, 87, 8187 (1990).
50. F. A. Cotton, G. Wilkinson, *Advanced Inorganic Chemistry, Fourth Edition* (Wiley, New York, 1980), p 99.
51. S. A. Emory, P. Bouvet, J. G. Belasco, *Genes Dev,* 6, 135 (1992).
52. Martinez-Salas, *Current Opinion in Biotechnology.* 10:458-464 (1999).
53. Barrick, D., et al., *Nuc. Acids. Res.* 22(7):1287-1295 (1994).
54. Rudd. K. E. and Schneider, T. D., in *A Short Course in Bacterial Genetics: A Laboratory Manual and Handbook for Escherichia coli and related bacteria.* (Miller, J. Ed.) Cold Spring Harbor Laboratory Press, Cold Spring Harbor, N.Y., pp. 17.19-17.45.
55. Ringquist, S., et al., *Molec. Microbiol.*, 6:1219-1229 (1992).
56. Pestova, T. V., et al., *Proc. Natl. Acad. Sci.* 98(13): 7029-7036 (2001).
57. Hellen, C. U. T., *Genes Dev.*, 15(13):1593-1612 (2001).
58. Kozak, M. *J. Mol. Biol.* 196: 947-950 (1987)
59. Kozak, M. *J. Cell Biol.* 108: 229-241 (1989).
60. Kozak, M., *J. Mol. Biol.*, 235: 95-110 (1994).
61. Al-Qahtani, A. and Mensa-Wilnot, K., *Nucleic Acids Res.*, 24(6):1173-4 (1996).
62. Chen, H., et al., *Nucleic Acids Res.*, 22: 4953-4957 (1994).
63. Kaem M, Blake W J, Collins J J. *Annu Rev Biomed Eng.* 5:179-206 (2003).
64. Werstuck, G. and Green, M., *Science,* 282: 296-298 (1998).
65. Alberts, B., et al., *Molecular Biology of the Cell*, 3$^{rd}$ ed., Garland (1994).
66. Tabor, J J and Ellington, A D., *Nat. Biotechnol.*, 21(9): 1013-1015 (2003).
67. Blau, H. and Rossi, F. M. V., *Proc. Natl. Acad. Sci.*, 96: 797-799 (1999).
68. Landweber, L, *Trends in Ecology and Evolution,* 14(9): 353-358 (1999).
69. Herman, T. and Patel, D., *Science,* 287: 820-825 (2000).
70. Sudarson, N., et al., *RNA,* 9: 644-647 (2003).
71. Lewandoski, M., *Nat Rev Genet.*, 2(10):743-55 (2001).
72. Wild, J., et al., *Genome Res.*, 12:1434-1444 (2002).
73. Boyd, D., et al., *J. Bacteriol.*, 182: 842-847 (2000).
74. Davies, D., et al., *Science,* 289:77-85 (2000).
75. Capecchi, M. R., *Science* 244:1288-1292 (1989).
76. Nagy, A. (ed.), *Manipulating the Mouse Embryo,* 3$^{rd}$ ed., Cold Spring Harbor Laboratory Press, Cold Spring Harbor N.Y. (2002).
77. Joyner, A. (ed.), *Gene Targeting: A Practical Approach,* 2nd ed., Oxford University Press (2002).
78. Vartanian, J. P., et al., *Nuc. Acids Res.*, 24:2627-2631 (1996).
79. Zaccolo, M., et al., *J. Mol. Biol.*, 285:775-783 (1999).
80. Brautigan, C. A. and Steitz, T. A., *Curr. Opin. Struct. Biol.,* 8:54-63 (1998).
81. Li, Y., et al., *EMBO J.*, 17:7514-7525 (1998).
82. Bedford, E., et al., *Proc. Natl. Acad. Sci. USA,* 94:479-84 (1997).
83. Li, Y., et al., *Proc. Natl. Acad. Sci. USA,* 96:9491-9496 (1999).
84. Suzuki, M., et al., *Proc. Natl. Acad. Sci. USA,* 93: 9670-9675 (1996).
85. Jestin, J. L., et al., *Angew. Chem. Int. Ed.* 38:1124-1127 (1999).
86. Oberholzer, T., et al., *Chem. Biol.,* 2:677-82 (1995).

---

We claim:

1. A recombinant prokaryotic cell comprising, a first exogenous mRNA nucleic acid sequence and a second exogenous mRNA nucleic acid sequence encoding a trans-activating RNA, wherein:
   a. the first exogenous mRNA nucleic acid sequence comprises a ribosome binding site (RBS) upstream of a nucleic acid sequence encoding a gene to be expressed, and a cis-repressive nucleic acid sequence located 5' of the RBS,
      wherein the cis-repressive nucleic acid sequence comprises at least 4 nucleic acids that are complementary to, or substantially complementary to at least 4 nucleic acids in the RBS and can, upon complementary base pairing of the at least 4 nucleic acids of the cis-repressive nucleic acid sequence with the at least 4 nucleic acids in the RBS form a duplex that is part of a repressive stem-loop structure, wherein the loop of the stem-loop structure is between 4-10 nucleotides; and
   b. the second exogenous nucleic acid sequence comprises an inducible promoter operatively linked to a nucleic acid sequence encoding the trans-activating RNA, wherein the trans-activating RNA comprises (i) a 5' non-stem nucleic acid sequence, comprising at least 4 nucleotides that are complementary to, or substantially complementary to at least 4 nucleotides of the cis-responsive nucleic acid sequence, and (ii) a stem-loop structure comprising a RNA duplex and loop;
   wherein:
      when the trans-activating RNA is not present, the cis-repressive nucleic acid sequence and RBS form the repressive stem-loop structure, wherein the repressive stem-loop structure blocks access of a ribosome to the RBS thereby repressing the translation of the gene, and
      when the trans-activating RNA is present, the 5' non-stem nucleic acid sequence of the trans-activating RNA forms a duplex with at least 4 nucleotides of the cis-repressive nucleic acid sequence, wherein the duplex disrupts the repressive stem-loop structure to expose the RBS, thereby allowing translation of the gene.

2. The recombinant prokaryotic cell of claim 1, wherein when the trans-activating RNA is not present, the cis-responsive nucleic acid sequence and RBS form a repressive stem-loop structure that blocks access of the ribosome to the RBS and represses translation of the gene by at least 80% as compared to translation of the gene when a repressive stem-loop structure is not formed.

3. The recombinant prokaryotic cell of claim 1, wherein when the trans-activating RNA is not present, the cis-responsive nucleic acid sequence and RBS form a repressive stem-loop structure that blocks access of the ribosome to the RBS and represses translation of the gene by at least 90% as compared to translation of the gene when a repressive stem-loop structure is not formed ORF.

4. The recombinant prokaryotic cell of claim 1, wherein when the trans-activating RNA is not present, the cis-responsive nucleic acid sequence and RBS form a repressive stem-loop structure that blocks access of the ribosome to the RBS and represses translation of the gene by at least 98% as compared to translation of the gene when a repressive stem-loop structure is not formed.

5. The recombinant prokaryotic cell of claim 1, wherein when the trans-activating RNA is present, the trans-activating RNA and cis-responsive nucleic acid sequence form a duplex that disrupts the repressive stem-loop structure to expose the RBS to increase the translation of the gene by at least 5 fold relative to the level of translation when the trans-activating RNA is not present.

6. The recombinant prokaryotic cell of claim 1, wherein when the trans-activating RNA is present, the trans-activating RNA and cis-repressive nucleic acid sequence form a duplex that disrupts the repressive stem-loop structure to expose the RBS to increase the translation of the gene by at least 10 fold relative to the level of translation when the trans-activating RNA is not present.

7. The recombinant prokaryotic cell of claim 1, wherein when the trans-activating RNA is present, the trans-activating RNA and cis-repressive nucleic acid sequence form a duplex that disrupts the repressive stem-loop structure to expose the RBS to increase the translation of the gene by at least 19 fold relative to the level of translation when the trans-activating RNA is not present.

8. The recombinant prokaryotic cell of claim 1, wherein the trans-activating nucleic acid sequence comprises, in 5' to 3' direction:
   (i) a first non-stem forming portion, comprising at least 4 nucleotides that is complementary to, or substantially complementary to at least 4 nucleotides of the cis-repressive nucleic acid sequence,
   (ii) a first stem-forming portion;
   (iii) a second non-stem forming portion; and
   (iv) a second stem-forming portion, comprising a nucleic acid sequence complementary to, or substantially complementary to the first-stem forming portion, wherein the first and second stem-forming portion complementary base pair to form a stem-loop structure, wherein the loop comprises the second non-stem forming portion,
   wherein the first non-stem forming portion of the trans-activating nucleic acid sequence can form a duplex with at least 4 nucleotides of the cis-repressive nucleic acid sequence to disrupt the repressive stem-loop structure, thereby allowing translation of the gene.

9. The recombinant prokaryotic cell of claim 1, wherein the loop of the repressive stem-loop structure comprises a YUNR sequence.

10. The recombinant prokaryotic cell of claim 1, wherein the loop of the repressive stem-loop structure is 4, 5, 6, 7, 8, 9, 10, 11, or 12 nucleotides in length.

11. The recombinant prokaryotic cell of claim 1, wherein the duplex of the repressive stem-loop structure is between 4 and 100 nucleotides in length, inclusive.

12. The recombinant prokaryotic cell of claim 1, wherein the duplex of the repressive stem-loop structure is between 6 and 50 nucleotides in length, inclusive.

13. The recombinant prokaryotic cell of claim 1, wherein the duplex of the repressive stem-loop structure is between 12 and 30 nucleotides in length, inclusive.

14. The recombinant prokaryotic cell of claim 1, wherein the duplex of the repressive stem-loop structure is approximately 19 nucleotides in length.

15. The recombinant prokaryotic cell of claim 8, wherein the duplex of the repressive stem-loop structure comprises nucleic acid sequences that exhibit at least 66% complementarity.

16. The recombinant prokaryotic cell of claim 8, wherein the duplex of the repressive stem-loop structure comprises nucleic acid sequences that exhibit between 75 and 95% complementarity.

17. The recombinant prokaryotic cell of claim 8, wherein the duplex of the repressive stem-loop structure comprises nucleic acid sequences that exhibit approximately 85% complementarity.

18. The recombinant prokaryotic cell of claim 8, wherein the duplex of the repressive stem-loop structure comprises at least one area of non-complementarity.

19. The recombinant prokaryotic cell of claim 1, wherein the duplex of the repressive stem-loop structure includes at least one bulge.

20. The recombinant prokaryotic cell of claim 1, wherein the duplex of the repressive stem-loop structure includes at least two dispersed areas of non-complementarity.

21. The recombinant prokaryotic cell of claim 20, wherein the duplex of the repressive stem-loop structure includes at least two dispersed bulges.

22. The recombinant prokaryotic cell of claim 1, wherein the duplex of the repressive stem-loop structure includes at least three dispersed areas of non-complementarity.

23. The recombinant prokaryotic cell of claim 22, wherein the duplex of the repressive stem-loop structure includes at least three dispersed bulges.

24. The recombinant prokaryotic cell of claim 1, wherein the first exogenous mRNA nucleic acid sequence forms a single stable stem.

25. The recombinant prokaryotic cell of claim 1, wherein the first exogenous mRNA nucleic acid sequence comprises a 5' portion of the ORF.

26. The recombinant prokaryotic cell of claim 1, wherein the first exogenous mRNA nucleic acid sequence comprises a start codon.

27. The recombinant prokaryotic cell of claim 26, wherein the first exogenous nucleic acid sequence comprises a spacer comprising one or more nucleotides between the 3' end of the second stem-forming portion and the start codon.

28. The recombinant prokaryotic cell of claim 1, wherein the first exogenous mRNA nucleic acid sequence comprises one or more nucleotides at the 5' end that do not participate in the stem-loop structure.

29. The recombinant prokaryotic cell of claim 1, wherein the first exogenous mRNA nucleic acid sequence comprises between 5 and 50 nucleotides upstream of the 5' end of the first stem-forming portion.

30. The recombinant prokaryotic cell of claim 1, wherein the first exogenous mRNA nucleic acid sequence comprises a ligand binding domain.

31. The recombinant prokaryotic cell of claim 1, wherein the first exogenous nucleic acid sequence further comprises a nucleic acid sequence that is at least 4 nucleotides in length and is complementary or substantially complementary to at least 4 nucleic acids in the cis-repressive nucleic acid sequence, and can, upon complementary base pairing with the at least 4 nucleic acid in the cis-repressive nucleic acid sequence form a duplex that is part of an alternate repressive stem-loop structures.

32. The recombinant prokaryotic cell of claim 8, comprising a YNAR sequence positioned 5' to the 5' end of the first stem forming portion.

33. The recombinant prokaryotic cell of claim 8, wherein the length of the stem formed by the two stem-forming portions of the second nucleic acid sequence is between 6 and 50 nucleotides.

34. The recombinant prokaryotic cell of claim 8, wherein the length of the stem formed by the two stem-forming portions of the second nucleic acid sequence is between 12 and 30 nucleotides.

35. The recombinant prokaryotic cell of claim 8, wherein the two stem-forming portions of the second nucleic acid sequence exhibit at least 66% complementarity.

36. The recombinant prokaryotic cell of claim 8, wherein the two stem-forming portions of the second nucleic acid sequence exhibit between 75 and 95% complementarity.

37. The recombinant prokaryotic cell of claim 8, wherein the stem formed by the two stem-forming portions of the second nucleic acid sequence includes at least one area of non-complementarity.

38. The recombinant prokaryotic cell of claim 8, wherein the stem formed by the two stem-forming portions of the second nucleic acid sequence includes at least two dispersed areas of non-complementarity.

39. The recombinant prokaryotic cell of claim 1, wherein the second exogenous nucleic acid sequence comprises a nucleotide analog.

40. The recombinant prokaryotic cell of claim 1, wherein the second exogenous nucleic acid sequence comprises a ligand binding domain.

41. A recombinant prokaryotic cell comprising, a first exogenous mRNA nucleic acid sequence and second exogenous nucleic acid sequence encoding a trans-activating RNA, wherein the first exogenous mRNA nucleic acid sequence has the sequence of SEQ ID NO:56 and the second exogenous nucleic acid sequence has the sequence of SEQ ID NO:55.

42. A recombinant prokaryotic cell comprising, a first exogenous mRNA nucleic acid sequence and second exogenous nucleic acid sequence encoding a trans-activating RNA, wherein the first exogenous mRNA nucleic acid sequence has the sequence of SEQ ID NO:56 or a variant of SEQ ID NO:56 that differs from SEQ ID NO:56 by 12 nucleotides or less and includes at least 3 dispersed areas of non-complementarity and the second exogenous nucleic acid sequence has the sequence of SEQ ID NO:55 or a variant of SEQ ID NO:55 that differs from SEQ ID NO:55 by 12 nucleotides or less and includes at least 3 dispersed areas of non-complementarity.

43. The recombinant prokaryotic cell of claim 1, wherein the first nucleic acid sequence and the second nucleic acid sequence have an equilibrium association constant between $0.8 \times 10^7$ and $1.5 \times 10^7$ kcal/mol.

* * * * *